United States Patent
Kelley et al.

(10) Patent No.: US 6,252,048 B1
(45) Date of Patent: Jun. 26, 2001

(54) DNA SEQUENCES ENCODING FUSIONS OF DNA REPAIR PROTEINS AND USES THEREOF

(75) Inventors: Mark Kelley, Zionsville; David Williams, Indianapolis, both of IN (US)

(73) Assignee: Advanced Research and Technology Institute, Indianapolis, IN (US)

( * ) Notice: Subject to any disclaimer, the term of this patent is extended or adjusted under 35 U.S.C. 154(b) by 0 days.

(21) Appl. No.: 09/542,403

(22) Filed: Apr. 3, 2000

Related U.S. Application Data

(63) Continuation of application No. 08/957,302, filed on Oct. 24, 1997, now Pat. No. 6,046,036.
(60) Provisional application No. 60/029,308, filed on Oct. 25, 1996.

(51) Int. Cl.[7] .............................. C07K 14/00; C07K 5/00; C12N 15/00; C07H 21/04

(52) U.S. Cl. ........................ 530/358; 530/300; 530/350; 435/69.1; 435/69.7; 435/183; 536/23.1; 536/23.2; 536/23.4; 536/23.5

(58) Field of Search ............................. 435/6, 69.7, 69.1, 435/440, 183, 193, 320.1, 325, 367, 243, 252, 33; 536/23.1, 23.2, 23.5, 23.4, 24.3, 24.31, 24.33; 514/44; 530/300, 350, 358

(56) References Cited

PUBLICATIONS

Morgan, S.E. et al. The Journal of Biological Chemistry, vol. 26, Sep. 1993, pp. 19802–19809.*

Allay, et al., "Retroviral transduction and expression of the human alkyltransferase cDNA provides nitrosourea resistance to hematopoietic celle," *Blood*, 85(11):3342–3351, 1995.

Anderson and Freidberg, "The presence of nuclear and mitochondrial uracil–DNA glycosylase in extracts of human KB cells," *Nucleic Acids Res.*, 8(4):875–888, 1980.

Armel and Wallace, "Apurinic endonucleases from *Saccharomyces cerevisiae*," *Nucleic Acids Res*, 5(9):3347–56, 1978.

Armel and Wallace, "DNA repair in *Saccharomyces cerevisiae*: purification and characterization of apurinic endonucleases," *J. Bacteriol.*, 160(3):895–902, 1984.

Bailly, et al., "Mechanism of DNA strand nicking at apurinic/apyrimidinic sites by *Escherichia coli* [formamidopyrimidine]DNA glycosylate," *Biochemical J.*, 262:581–589, 1989.

Barrows and Magee, "Nonenzymatic methylation of DNA bt S–adenosylmethioine in vitro," *Carcinogenesis*, 3(3):349–351, 1982.

Barzilay et al., "Identification of critical active–site residues in the multifunctional human DNA repair enzyme HAP1," *Nat. Struct. Biol.*, 2(7):561–8, 1995.

Barzilay et al., "Site–directed mutagenesis of the human DNA repair enzyme HAP1: identification of residues important for AP endonuclease and RNase H activity," *Nucleic Acids Res.*, 23(9):1544–50, 1995.

Bjelland et al., "DNA glycosylase activites for thymine residues oxidized in the methyl group are functions of the AlkA enzyme in *Escherichia coli*," *J. Biol. Chem.*, 269(48):30489–30495, 1994.

(List continued on next page.)

*Primary Examiner*—John L. LeGuyader
*Assistant Examiner*—Mark L. Shibuya
(74) *Attorney, Agent, or Firm*—Fulbright & Jaworski

(57) ABSTRACT

Described are DNA-repair fusion proteins of multiple, complementary DNA repair proteins and having the activity of each protein, and related polynucleotides and vectors. The proteins, when expressed in cells, e.g., hematopoietic cells, increase the survival rate of the cells when contacted with chemotherapeutic agents. Also described are transgenic animal models wherein these proteins are expressed in essentially all cells of the animal. Such animal models are useful for instance in testing chemotherapeutic agents.

11 Claims, 18 Drawing Sheets

OTHER PUBLICATIONS

Bodine et al., "Long–term in vivo expression of a murine adenosine deaminase gene in Rhesus monkey hematopoietic cells of multiple lineages after retroviral mediated gene transfer into CD34$^{30}$ bone marrow cells," *Blood*, 82(7):1975–1980, 1993.

Boiteux and Laval, "Imidazole open ring 7–methylguanine: an inhibitor of DNA synthesis," *Biochem. Biophys. Res. Commun.*110(2):552–558, 1983.

Boiteux et al., "Homogeneous *Escherichia coli* FPG protein," *J. Biol. Chem.*, 265(7):3916–3922, 1990.

Bonura et al., "An enzyme activity from *Escherichia coli* that attacks single–stranded deoxyribopolymers and single–stranded deoxyribonucleic acid containing apyrimidinic sites," *Biochemistry*, 21(10):2548–56, 1982.

Brent and Remack, "Formation of covalent complexes between human O$^6$–alkylguanine–DNA alkyltransferase and BCNU–treated defined length synthetic oligodeoxynucleotides," *Nucl. Acid Res.*, 16(14):6779–6788, 1988.

Broun et al., "Long–term outcome of patients with relapsed and refractory germ cell tumors treated with high–dose chemotherapy and autologous bone marrow rescue," *Annals Intern. Med.*, 117(2):124–128, 1992.

Bucala et al., "Modification of DNA by reducing sugars: a possible mechanism for nucleic acid aging and age–related dysfunction in gene expression," *Proc. Natl. Acad. Sci. USA*, 81(1):105–9, 1984.

Cabrera et al., "mutM, a second mutator locus on *Escherichia coli* that generates G•C→T•A transversions," *J. Bacteriology*, 170:5405–5407, 1988.

Carter et al., "1,3–BIS(2–chloroethyl)–1–nitrosourea (BCNU) and other nitrosoureas in cancer treatment: a review," *Adv. Cancer Res.* 16:273–332, 1972.

Clarke et al., "Cloning of *Escherichia coli* genes encoding 3–methyladenine DNA glycosylases I and II," *Mol. Gen. Genet.*, 197(3):368–372, 1984.

Cunningham et al., "Endonuclease IV (nfo) mutant of *Escherichia coli*," *J. Bacteriol.*, 168(3):1120–1127, 1986.

Del Rosso et al., "Involvement of glycosaminoglycans in detachment of early myeloid precursors from bone–marrow stromal cells," *Biochim. Biophys. Acta*, 676:129–136, 1981.

Demple and Halbrook, "Inducible repair of oxidative DNA damage in *Escherichia coli*," *Nature*, 304(4):466–468, 1983.

Demple and Harrison, "Repair of oxidative damage to DNA: enzymology and biology," *Ann. Rev. Biochem.*, 63:915–48, 1994.

Demple and Linn, "5,6–saturated thymine lesions in DNA: production by ultravoilet light or hydrogen peroxide," *Nucleic Acids Res*, 10(12):3781–9, 1982.

Demple et al.,"*Escherichia coli* xth mutants are hypersensitive to hydrogen peroxide," *J. Bacteriol.*, 153(2):1079–1082, 1983.

Demple et al., "Exonuclease III and endonuclease IV remove 3' blocks from DNA synthesis primers in H$_2$O$_2$–damaged *Escherichia coli*," *Proc. Natl. Acad. Sci. USA*, 83:7731–7735, 1986.

Demple et al., "Cloning and expression of APE, the cDNA encoding the major human apurinic endonuclease: definition of a family of DNA repair enzymes," *Proc. Natl. Acad. Sci. USA*, 88:11450–11454, 1991.

Dianov and Lindahl, "Reconstitution of the DNA base excision–repair pathway," *Curr. Biol.*, 4(12):1069–1076, 1994.

DiCapua, Schnarr and Timmins, "The location of DNA in complexes of recA protein with double–stranded DNA. A neutron scattering study," *Biochemistry*, 28:3287–3292, 1989.

Doetsch and Cunningham, "The enzymology of apurinic/apyrimidinic endonucleases," *Mutat. Res.*, 236:173–201, 1990.

Doetsch et al., "Monomeric base damage products from adenine, guanine, and thymine induced by exposure of DNA to ultraviolet radiation," *Biochemistry*, 34:737–742, 1995.

Dolan et al., "Depletion of mammalian O$^6$–alkylguanine–DNA alkyltransferase activity by O$^6$–benzylguanine provides a means to evaluate the role of this protein in protection against carcinogenic and therapeutic alkylating agents," *Proc. Natl. Acad. Sci. USA*, 87:5368–5372, 1990.

Domena and Mosbaugh, "Purification of nuclear and mitochondrial uracil–DNA glycosylase from rat liver. Identification of two distinct subcellular forms," *Biochemistry*, 24(25):7320–8, 1985.

Domena et al., "Purfication and properties of mitochondrial uracil–DNA glycosylase from rat liver," *Biochemistry*, 27(18):6742–51, 1988.

Duncan and Weiss, "Specific mutator effects of ung (uracil–DNA glycosylase) mutations in *Escherichia coli*," *J. Bacteriol.*, 151(2):750–755, 1982.

Erickson et al., "DNA cross–linking and monoadduct repair in nitrosourea–treated human tumour cells," *Nature*, 288:727–29, 1980.

Evensen and Seeberg et al., "Adaptation to alkylation resistance involves the induction of a DNA glycosylase," *Nature*, 296:773–5, 1982.

Feig and Loeb, "Mechanisms of mutation by oxidative DNA damage: reduced fidelity of mammalian DNA polymerase β," *Biochemistry*, 32(16):4466–73, 1993.

Friedberg et al., *DNA Repair and Mutagenesis*, Washington, D.C., ASM Press, 1995.

Friedberg and Goldthwait, "Endonuclease II of *E. coli*, I. Isolation and purification," *Proc. Natl. Acad. Sci. USA*, 62(3):934–40, 1969.

Gajewski et al., "Modification of DNA bases in mammalian chromatin by radiation–generated free radicals," *Biochemistry*, 29:7876–82, 1990.

Gates and Linn, "Endonuclease from *Escherichia coli* that acts specifically upon duplex damaged by ultraviolet light, osmium tetroxide, acid, or x–rays," *J. Biol. Chem.*, 252(9):2802–7, 1977.

Gensler and Bernstein, "DNA damage as the primary cause of aging," *The Quarterly Review of Biology*, 56:279–303, 1981.

Gerson et al., "Comparison of O$^6$–alkylguanine–DNA alkyltransferase activity based on cellular DNA content in human, rat and mouse tissues," *Carcinogenesis*, 7(5):745–749, 1986.

Gerson et al., "O$^6$–alkylguanine–DNA alkyltransferase activity in human myeloid cells," *J. Clin. Invest.*, 76:2106–2114, 1985.

Gill et al., "Increased resistance to N,N', N"–triethylenethiophosphoramide (thiotepa) in cells expressing the *Escherichia coli* formamidopyrimidine–DNA glycosylase," *Cancer Res.*, 56:3721–3724, 1996.

Giloni et al., "Bleomycin–induced strand–scission of DNA," *J. Biol. Chem.*, 256(16):8608–15, 1981.

Gossard and Verly, "Properties of the main endouclease specific for apurinic sites of *Escherichia coli* (endonuclease VI)," *Eur. J. Biochem.*, 82(2):321–32, 1978.

Greenbaum et al., "Retrovirus–mediated gene transfer of rat glutathione S–transferase Yc confers alkylating drug resistance in NIH 3T3 mouse fibroblasts," *Cancer Res.*, 54:4442–47, 1994.

Halliwell and Aruoma, "DNA damage by oxygen derived species," *FEBS Lett.*, 281(1–2):9–19, 1991.

Hanania and Deisseroth, "Serial transplantation shows that early hematopoietic precursor cells are transduced by MDR–1 retroviral vector in a mouse gene therapy model," Canc. *Gene Ther.*, 1(1):21–25, 1994.

Hanenberg et al., "Colocalization of retrovirus and target cells on specific fibronectin fragments increases genetic transduction of mammalian cells," *Nature Medicine*, 2:876, 1996.

Harosh and Sperling, "Hypoxanthine–DNA glycosylase from *Escherichia coli,*" *J. Biol. Chem.*, 263(7):3328–34, 1988.

Harrison et al., "Human apurinic endonuclease gene (APE): structure and genomic mapping (chromosome 14q11.2–12)," *Hum. Mol. Genet.*, 1(9):677–680, 1992.

Harrison et al., "Transfection of the *Escherichia coli nth* gene into radiosensitive Chinese hamster cells: effects on sensitivity to radiation, hydrogen peroxide, and bleomycin sulfate," *Radiat Res* 132(1):30–39, 1992.

Haseltine, "Ultraviolet light repair and mutagenesis revisited," *Cell*, 33(1):13–17, 1983.

Haukanes et al., "Action of a mammalian AP–endonuclease on DNAs of define sequences," *Nucleic Acids Res*, 17(4):1493–1509, 1989.

Haukanes et al., "Mechanism of incision by an apurinic/apyrimidinic endonuclease present in human placenta," *Nucleic Acids Res.*, 17(14):5529–5535, 1989.

Hayatsu, "Bisulfite modification of nucleic acids and their constituents," *Prog. Nucl. Adds Res. Mol. Biol.*, 16:75–124, 1976.

Henner et al., "Enzyme action at 3' termini of ionizing radiation–induced DNA strand breaks," *J. Biol. Chem.*, 258(24):15198–205, 1983.

Henner et al., "Purification and amino–terminal amino acid sequence of an apurinic/apyrimidinic endonuclease from calf thymus," *Nucleic Acids Res*, 15(14):5529–5544, 1987.

Ho et al., "Site–directed mutagenesis by overlap extension using the polymerase chain reaction," *Gene*, 77:51–59, 1989.

Horton et al., "Strategic down–regulation of DNA polymerase β by antisense RNA sensitizes mammalian cells to specific DNA damaging agents," *Nucl. Acids Res.*, 23(19):3810–3815, 1995.

Hutchinson et al., "Characterization of a new simian virus 40 mutant, tsA3900, isolated from deletion mutant tsA1499," *J. Virol.*, 53(3):814–21, 1985.

Hutchinson, "Chemical changes induced in DNA by ionizing radiation," *Prog. Nucl. Acid. Res. Mol. Biol.*, 32:115–154, 1985.

Imlay and Linn, "DNA damage and oxygen radical toxicity," *Science*, 240:1302–1309, 1988.

Jelinek et al., "Long–term protection of hematopoiesis against the cytotoxic effects of multiple doses of nitrosourea by retrovirus–mediated expression of human $O^6$–alkylguanine–DNA–alkyltransferase," *Blood*, 87(5):1957–61, 1996.

Johnson and Demple, "Yeast DNA 3'–repair diesterase is the major cellular apurinic/apyrimidinic endonuclease: substrate specificity and kinetics," *J. Biol. Chem.*, 263(34):18017–18022, 1988.

Johnson and Demple, "Yeast DNA diesterase for 3'–fragments of deoxyribose: purification and physical properties of a repair enzyme for oxidative DNA damage," *J. Biol. Chem.*, 263(34):18009–16, 1988.

Kaina et al., "Contribution of $O^6$–alkylguanine and N–alkylpurinines to the formation of sister chromatid exchanges, chromosomal aberrations, and gene mutations: new insights gained from studies of genetically engineered mammalian cell lines," *Envir. and Mol. Mutag.*, 22:283–292, 1993.

Kamel–Reid and Dick, "Engraftment of immune–deficient mice with human hematopoietic stem cells," *Science*, 242:1706–09, 1988.

Kane and Linn, "Purification and characterization of an apurinic/apyrimidinic endonuclease from HeLa cells," *J. Biol. Chem.*, 256(7):3405–3414, 1981.

Karran and Lindahl, "Hypoxanthine in deoxyribonucleic acid: generation by heat–induced hydrolysis of adenine residues and release in free from by a deoxyribonucleic acid glycosylase from calf thymus," *Biochemistry*, 19(26):6005–11, 1980.

Karran et al., "Induction of a DNA glycosylase for N–methylated purines is part of the adaptive response to alkylating agents," *Nature*, 296:770–773, 1982.

Kirtikar et al., "Endonuclease II of *Escherichia coli*: DNA reacted with 7–bromomethyl–12–methylbenz[a]anthracene as a substrate," *Biochemistry*, 14(26):5548–53, 1975.

Kow and Wallace, "Mechanism of action of *Escherichia coli* endonuclease III," *Biochemistry*, 26(25):8200–6, 1987.

Kow and Wallace, "Exonuclease III recognizes urea residues in oxidized DNA," *Proc. Natl. Acad. Sci. USA*, 82:8354–8358, 1985.

Kow, "Mechanism of action of *Escherichia coli* exonuclease III," *Biochemistry*, 28(8):3280–3287, 1989.

Krokan and Wittwer, "Uracil DNA–glycosylase from HeLa cells: general properties, substrate specificity and effect of uracil analogs," *Nucleic Acids Res.*, 9(11):2599–613, 1981.

Lamar and Palmer, "Y–encoded, species–specific DNA in mice: evidence that the Y chromosome exisits in two polymorphic forms in inbred strains," *Cell*, 37:171–177, 1984.

Laval, "Role of DNA repair enzymes in the cellular resistance to oxidative stress," *Path. Biol.*44:14–24, 1996.

Lee and Cerami, "Elevated glucose 6–phosphate levels are associated with plasmid mutations in vivo," *Proc. Natl. Acad. Sci. USA*, 84:(23):8311–14, 1987.

Lindahl and Nyberg, "Rate of depurination of native deoxyribonucleic acid," *Biochem.*, 11(19):3610–3618, 1972.

Lindahl and Sedgwick, "Regulation and expression of the adaptive response to alkylating agents,"*Ann. Rev. Biochem.*, 57:133–57, 1988.

Lindahl, "An N–glycosidase from *Escherichia coli* that releases free uracil from DNA containing deaminated cytosine residues," *Proc. Natl. Acad. Sci. USA*, 71(9):3649–3653, 1974.

Loeb and Preston, "Mutagenesis by apurinic/apyrimidinic sites," *Ann. Rev. Genet.*, 20:201–30, 1986.

Lorenzi et al., "High glucose induces DNA damage in cultured human endothelial cells," *J. Clin. Invest.*, 77(1):322–25, 1986.

Loveless, "Possible relevance of O–6 alkylation of deoxyguanosine to the mutagenicity and carcinogenicity of nitrosamines and nitrosamides," *Nature*, 223(202):206–207, 1969.

Lowenhaupt et al., "*Drosophila melanogaster* strand transferase," *J. Biol. Chem.*, 264(34):20568–75, 1989.

Ludlum, "DNA alkylation by the haloethylnitrosoureas: nature of modifications produced and their enzymatic repair or removal," *Mutation Res.*, 233:117–126, 1990.

Magni et al., "Induction of cyclophosphamide–resistance by aldehyde–dehydrogenase gene transfer," *Blood*, 87(3):1097–1103, 1996.

Majumdar et al., "Xenogenic expression of human stem cell factor in transgenic mice mimics codominant c–kit mutations," *Blood*, 87(8):3203–3211, 1996.

Mann et al., "Construction of a retrovirus packaging mutant and its use to produce helper–free defective retrovirus," *Cell*, 33:153–159, 1983.

Maze et al., "Increased survival and multilineage hematopoietic protection from delayed and severe myelosuppressive effects of a nitrosourea with recombinant interleukin–11," *Cancer Res.*, 54:4947–51, 1994.

Maze et al., "Increasing DNA repair methyltransferase levels via bone marrow stem cell transduction rescues mice from the toxic effects of 1,3–bis(2–chloroethyl)–1–nitrosourea, a chemotherapeutic alkylating agent," *Proc. Nat'l. Acad. Sci. USA*, 93:206–210, 1996.

Mitani et al., "The repair of UV–irradiated plasmids trasfected into cultured fish cells," *Mutat. Res.*, 236:77–84, 1990.

Mitra et al., "Apoptosis in keratinocytes is not dependent on induction of differentiation," *Lab Invest*, 76(1):99–107, 1997.

Moritz et al., "Bone marrow extracellular matrix molecules improve gene transfer into human hematopoietic cells via retroviral vectors," *J. Clin. Invest.*, 93:1451–57, 1994.

Moritz et al., "Fibronectin improves transduction of reconstituting hematopoietic stem cells by retroviral vectors: evidence of direct viral binding to chymotryptic carboxy––terminal fragments," *Blood*, 88(3):855–862, 1996.

Moritz et al., "Retrovirus–mediated expression of a DNA repair protein in bone marrow protects hematopoietic cells from nitrosoursea–induced toxicity in vitro and in vivo," *Cancer Res.*, 55:2608–2614, 1995.

Moritz and Williams, "Somatic gene therapy," In: *Scientific Basis of Transfusion Medicine*, Anderson, Ed., Philadelphia, Churchill Linvingstone, Chapter 50, pp. 872–888, 1994.

Moritz et al., "Transfer of Drug Resistance Genes to Hematopoietic Precursors", *Encyclopedi of Cancer*, #:1765–1776, 1997.

Muller and Caradonna, "Isolation and characterization of a human cDNA encoding uracil–DNA glycosylase," *Biochim Biophys Acta*, 1088(2):197–207, 1991.

Myrnes et al., "Repair of $O^6$–methyl–guanine residues in DNA takes place by a similar mechanism in extracts from HeLa cells, human liver, and rat liver," *J. Cell. Biochem.*, 20(4):381–92, 1982.

Nakabeppu et al., "Structure and expression of the alkA gene of *Escherichia coli* involved in adaptive response to alkylating agents," *J. Biol. Chem.*, 259(22):13730–13736, 1984.

Olsen et al., "Molecular cloning of human uracil–DNA glycosylase, a highly conserved DNA repair enzyme," *EMBO J.*, 8(10):3121–25, 1989.

Ono et al., "Developmental expression of APEX nuclease, a multifunctional DNA repair enzyme, in mouse brains," *Devel. Brain Res.*, 86:1–6, 1995.

Pegg, "Mammalian $O^6$–alkylguanine–DNA alkyltransferase: regulation and importance in response to alkylating carcinogenic and therapeutic agents," *Cancer Res.*, 50:6119–6129, 1990.

Pegg et al., Structure, function, and inhibition of $O^6$–alkylguanine–DNA alkyltransferase, *Progress in Nucleic Acid Research and Molecular Biology* 51:167–223, 1995.

Petrini et al., "A wild–type DNA ligase I gene is expressed in Bloom's syndrome cells," *Proc. Natl. Acad. Sci. USA*, 88(17):7615–19, 1991.

Popoff et al., "Yeast structural gene (APNI) for the major aspurinic endonuclease: homology to *Escherichia coli* endonuclease IV," *Proc. Natl. Acad. Sci. USA*, 87:4193–4197, 1990.

Povirk and Houlgrave, "Effect of apurinic/apyrimidinic endonucleases and polyamines on DNA treated with bleomycin and neocarzinostatin: specific formation and cleavage of closely opposed lesions in complementary strands," *Biochem.*, 27:3850–3857, 1988.

Ramotar et al., "Cellular role of yeast Apn 1 apurinic endonuclease/3'–diesterase: repair of oxidative and alkylation DNA damage and control of spontaneous mutation," *Mol Cell Biol*, 11(9):4537–44, 1991.

Robins et al., "Cross–linking of DNA induced by chloroethylnitrosourea is prevented by $O^6$–methylguanine–DNA methyltransferase," *Nucl. Acids Res.*, 11(22):7743–7759, 1983.

Robson and Hickson, "Isolation of cDNA clones encoding a human apurinic/apyrimidinic endonuclease that corrects DNA repair and mutagenesis defects in *E. coli* xth (exonuclease III) mutants," *Nucl. Acids Res.*, 19(20):5519–5523, 1991.

Robson et al., "Isolation of cDNA clones encoding an enzyme from bovine cells that repairs oxidative DNA damage in vitro: homology with bacterial repair enzymes," *Nucl. Acids Res.*, 19(5):1087–1092, 1991.

Robson et al., "Structure of the human DNA repair gene HAP1 and its localization to chromosome 14q 11.2–12," *Nucl. Acids Res.*, 20(17):4417–4421, 1992.

Rogers and Weiss, "Exonuclease III from *E. coli*," *Methods Enzymol.*, 65(26):201–211, 1980.

Russell and Miller, "Foamy virus vectors," *J Virol.*, 70(1):217–222, 1996.

Saffhill et al., "Mechanisms of carcinogenesis induced by alkylating agents," *Biochim. Biophys.*, 823:111–145, 1985.

Sakumi and Sekiguchi, "Structures and functions of DNA glycosylases," *Mutation Res.*, 236:161–172, 1990.

Samson et al., "Suppression of human DNA alkylation–repair defects of *Escherichia coli* DNA–repair genes," *Proc. Natl. Acad. Sci. USA*, 83:5607–5610, 1986.

Sancar and Sancar, "DNA repair enzymes," *Ann. Rev. Biochem.*, 57:29–67, 1988.

Sander et al., "Drosophilia Rrp1 protein: An apurinic endonuclease with homologous recombination activities," *Proc. Natl. Acad. Sci. USA*, 88:6780–6784, 1991.

Sander et al., "Cloning and characterization of Rrp 1, the gene encoding Drosophila strand transferase: carboxy–terminal homology to DNA repair endo/exonucleases," *Nucl. Acids Res.*, 19(16):4523–4529, 1991.

Sander, "Angiomatous malformation of placental chronic stem vessels and pseudo–partial molar placentals: report of five cases," *Pediatr. Pathol.*, 13(5):621–633, 1993.

Saporito and Cunningham, "Nucleotide sequence of the nfo gene of *Escherichia coli* K–12," *J. Bacteriol.*, 170(11):5141–5145, 1988.

Saporito et al., "Nucleotide sequence of the xth gene of *Escherichia coli* K–12," *J. Bacteriol.*, 170(10):4542–4547, 1988.

Saul and Bonifaz, "Itraconazole in the treatment of superficial mycoses: an open trial of 40 cases," *Rev. Infect. Dis.*, 9(1):S100–S103, 1987.

Schuster, "The reaction of nitrous acid with deoxyribonucleic acid," *Biochem. Biophys. Res. Comm.*, 2(5):320–323, 1960.

Seal et al., "Purification and properties of the uracil DNA glycosylase from Bloom's syndrome," *Biochim. Biophys. Acta*, 1097:299–308, 1991.

Seki et al., "A mouse DNA repair enzyme (APEX nuclease) having exonuclease and aspurinic/apyrimidinic endonuclease activies: purification and characterization," *Biochim. Biophys. Acta*, 1079:57–64, 1991.

Seki et al., "cDNA and deduced amino acid sequence of a mouse DNA repair enzyme (APEX nuclease) with significant homology to *Escherichia coli* Exonuclease III," *J. Biol. Chem.*, 266(31):20797–20802, 1991.

Shaper et al., "Human Placental Apurinic/ Apyrimidinic Endonuclease," *J. Biol. Chem.*, 257(22):13455–13458, 1982.

Simonian and Coyle, "Oxidative stress in neurodegenerative diseases," *Ann. Rev. Pharmacol. Toxicol.*, 36:83–106, 1996.

Smith and Waterman, "Comparison of Biosequences," *Adv. Appl. Math.*, 2:482–489, 1981.

Smith et al., "Influence of doxorubicin dose intensity on response and outcome for patients with osteogenic sarcoma and Ewing's Sarcoma," *J. Natl. Canc. Instit.*, 83(20):1460–1470, 1991.

Spiering and Deutsch, "Drosophilia apurinic/ apyrimidinic DNA endonucleases," *J. Biol. Chem.*, 261(7):3222–3228, 1986.

Spiering and Deutsch, "Apurinic DNA endonucleases from *Drosophilia melanogaster* embryos," *Mol. Gen. Genet.*, 183:171–174, 1981.

Srour et al., "Persistence of human multilineage, self–renewing lymphohematopoietic stem cells in chimeric sheep," *Blood*, 82(11):3333–3342, 1993.

Téoule, "Radiation–induced DNA damage and its repair," *Int. J. Rad. Biol.*, 51(4):573–589, 1987.

Thomas et al., "Two DNA glycosylases in *Escherichia coli* which release primarily 3–methyladenine," *Biochem.*, 21:1162–1169, 1982.

Tomicic et al., "Expression of yeast but not human apurinic/ apyrimidinic endonuclease renders Chinese hamster cells more resistant to DNA damaging agents," *Mut. Res.*, 383:155–165, 1997.

Toorchen and Topel, "Mechanisms of chemical mutagenesis and carcinogenesis: effects on DNA replication of methylation at the $O^6$–guanine postion of dGTP," *Carcinogenesis*, 4(12):1591–1597, 1983.

Troelstra et al., "Localization of the nucleotide excision repair gene ERCC6 to human chromosome 10q11–q21," *Genomics*, 12:745–749, 1992.

Troelstra et al., "ERCC6, a member of a subfamily of putative helicases, is involved in Cockayne's Syndrome and preferential repair of active genes," *Cell*, 71:939–953, 1992.

Vollberg et al., "Monoclonal antibodies detect conformational abnormality of uracil DNA glycosylase in Bloom's syndrome cells," *Carcinogen.*, 8(11):1725–1729, 1987.

Vollberg et al., "Isolation and characterization of the human uracil DNA glycosylase gene," *Proc. Natl. Acad. Sci. USA*, 86:8693–8697, 1989.

von Sonntag et al., "The chemistry of free–radical–medicated DNA damage," *Basic Life Sci.*, 58:287–317, 1991.

Wang et al., "Retrovirus–mediated transfer of the human $O^6$–methylguanine–DNA methyltransferase gene into a murine hematopoietic stem cell line and resistance to the toxic effects of certain alkylating agents," *Biochem. Pharmacol.*, 51:1221–1228, 1996.

Wallace, "AP endonucleases and DNA glycosylases that recognize oxidative DNA damage," *Envir. Mol. Mut.*, 12:431–477, 1988.

Washington et al., "Tissue–specific variation in repair activity for 3–methyladenine in DNA in two stocks of mice," *Mut. Res.*, 207:165–169, 1988.

Weiss et al., "Improved replication of *Autographa californica* nuclear polyhedrosis virus in roller bottles: characterization of the progeny virus," *Intervirol.*, 15:213–222, 1981.

Weng and Sirover, "Developmental regulation of the base excision repair enzyme uracil DNA glycosylase in the rat," *Mut. Res., DNA Repair*, 293:133–141, 1993.

Wigler et al., "Transfer of purified herpes virus thymidine kinase gene to cultured mouse cells," *Cell*, 11:223–232, 1977.

Wigler et al., "Transformation of mammalian cells with an amplifiable dominant–acting gene," *Proc. Natl. Acad. Sci. USA*, 77(6):3567–3570, 1980.

Williams et al., "Protection of bone marrow transplant recipients from lethal doses of methotrexate by the generation of methotrexate–resistant bone marrow," *J. Exp. Med.*, 166:210–218, 1987.

Williams et al., "Introduction of new genetic material into pluripotent haematopoietic stem cells of the mouse," *Nature*, 310:476–480, 1984.

Willis and Lindahl, "DNA ligase I deficiency in Bloom's syndrome," *Nature*, 325:355–357, 1987.

Willson et al., "Modulation of $O^6$–alkylguanine alkyltransferase–directed DNA repair in metastatic colon cancers," *J. Clin. Oncol.*, 13(9):2301–2308, 1995.

Wilson et al., "Drosophila ribosomal protein S3 contains an activity that cleaves DNA at apurinic/ apyrimidinic sites," *J. Biol. Chem.*, 269(41):25359–25364, 1994.

Wilson et al., "Cloning of the Drosophila ribosomal protein S3: another multifunctional ribosomal protein with AP endonuclease DNA repair activity," *Nucl. Acids Res.*, 21(10):2516, 1993.

Wist et al., "Accumulation of small fragments of DNA in isolated HeLa cell nuclei due to transient incorporation of dUMP," *Biochim. Biophys. Acta*, 520:253–270, 1978.

Wittwer et al., "Purification and determination of the $NH_2$–terminal amino acid sequence of uracil–DNA glycosylase from human placenta," *Biochem.*, 28:780–784, 1989.

Wittwer and Krokan, "Uracil–DNA glycosylase in HeLa $S_3$ cells: interconvertibility of 50 and 20 kDa forms and similarity of the nuclear and mitochondrial form of the enzyme," *Biochim. Biophys. Acta*, 832:308–318, 1985.

Xanthoudakis and Curran, "Redox regulation of AP–1," In: *Biological Reactive Intermediates V*, Snyder et al., eds., Plenium Press, NY, pp. 69–75, 1996.

Xanthoudakis and Curran, "Indentification and characterization of Ref–1, a nuclear protein that facilitates AP–1 DNA–binding activity," *EMBO J.*, 11(2):653–665, 1992.

Xanthoudakis et al., "Redox activation of Fos–Jun DNA binding activity is mediated by a DNA repair enzyme," *EMBO J.*, 11(9):3323–3335, 1992.

Xanthoudakis et al., "The redox and DNA–repair activities of Ref–1 are encoded by nonoverlapping domains," *Proc. Natl. Acad. Sci. USA*, 91:23–27, 1994.

Xiao and Samson, "In vivo evidence for endogenous DNA alkylation damage as a source of spontaneous mutation in eukaryotic cells," *Proc. Natl. Acad. Sci. USA*, 90:2117–2121, 1993.

Yacoub et al., "A Drosophila ribosomal protein contains 8–oxoguanine and abasic site DNA repair activities," *EMBO J.*, 15(9):2306–2312, 1996.

Yamamoto and Fujiware, "Abnormal regulation of uracil–DNA glycosylase induction during cell cycle and cell passage in Bloom's syndrome fibroblasts," *Carcinogen.*, 7(2):305–310, 1986.

Zaharko et al., "Relative toxicity of methotrexate in several tissues of mice bearing Lewis Lung Carcinoma," *J. Pharmacol. Exp. Ther.*, 189(3):585–592, 1974.

Dumenco et al., "The Prevention of Thymic Lymphomas in Transgenic Mice by Human $O^6$–Alkylguanine–DNA Alkyltransferase," *Science*, 259:219–222, 1993.

PCT Search Report dated Jun. 17, 1998.

Liem et al., "Factors Influencing the Repair of the Mutagenic Lesion $O^6$–mrthylguanine in DNA by Human $O^6$–methylguanine–DNA Methyltransferase," *J. Mol. Biol.*, 231:950–959, 1993.

Matsuoka et al., "D–type Cyclin–binding Regions of Proliferating Cell Nuclear Antigen," *Journ. Bio. Chem.*, 269:11030–11036, 1994.

Marshall, E., "Gene therapy's growing pains," *Science*, 269:1050–1055, Aug. 25, 1995.

Mastrangelo et al., "Gene therapy for human cancer: as essayf or clinicians," *Seminars in Oncology*, 23(1):4–21, Feb. 1996.

Written Opinion, PCT/US97/19629, dated Sep. 11, 1998.

* cited by examiner

*Pathway with Glycosylase*
*(BER - A)*

*Pathway with Glycosylase /AP Lyase*
*(BER - B)*

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
       (A) LENGTH: 1575 base pairs
       (B) TYPE: nucleic acid
       (C) STRANDEDNESS: single
       (D) TOPOLOGY: linear (xi) SEQUENCE DESCRIPTION: SEQ ID NO: 1:

```
ATGGACAAGG ATTGTGAAAT GAAACGCACC ACACTGGACA GCCCTTTGGG GAAGCTGGAG        60

CTGTCTGGTT GTGAGCAGGG TCTGCACGAA ATAAAGCTCC TGGGCAAGGG GACGTCTGCA       120

GCTGATGCCG TGGAGGTCCC AGCCCCCGCT GCGGTTCTCG GAGGTCCGGA GCCCCTGATG       180

CAGTGCACAG CCTGGCTGAA TGCCTATTTC CACCAGCCCG AGGCTATCGA AGAGTTCCCC       240

GTGCCGGCTC TTCACCATCC CGTTTTCCAG CAAGAGTCGT TCACCAGACA GGTGTTATGG       300

AAGCTGCTGA AGGTTGTGAA ATTCGGAGAA GTGATTTCTT ACCAGCAATT AGCAGCCCTG       360

GCAGGCAACC CCAAAGCCGC GCGAGCAGTG GGAGGAGCAA TGAGAGGCAA TCCTGTCCCC       420

ATCCTCATCC CGTGCCACAG AGTGGTCTGC AGCAGCGGAG CCGTGGGCAA CTACTCCGGA       480

GGACTGGCCG TGAAGGAATG GCTTCTGGCC CATGAAGGCC ACCGGTTGGG GAAGCCAGGC       540

TTGGGAGGGA GCTCAGGTCT GGCAGGGGCC TGGCTCAAGG GAGCGGGAGC TACCTCGGGC       600

TCCCCGCCTG CTGGCCGAAA CCCGAAGCGT GGGAAAAAGG GAGCGGTGGC GGAAGACGGG       660

GATGAGCTCA GGACAGAGCC AGAGGCCAAG AAGAGTAAGA CGGCCGCAAA GAAAAATGAC       720

AAAGAGGCAG CAGGAGAGGG CCCAGCCCTG TATGAGGACC CCCAGATCA GAAAACCTCA        780

CCCAGTGGCA AACCTGCCAC ACTCAAGATC TGCTCTTGGA ATGTGGATGG GCTTCGAGCC       840

TGGATTAAGA AGAAAGGATT AGATTGGGTA AAGGAAGAAG CCCCAGATAT ACTGTGCCTT       900

CAAGAGACCA AATGTTCAGA GAACAAACTA CCAGCTGAAC TTCAGGAGCT GCCTGGACTC       960

TCTCATCAAT ACTGGTCAGC TCCTTCGGAC AAGGAAGGGT ACAGTGGCGT GGGCCTGCTT      1020

TCCCGCCAGT GCCCACTCAA AGTTTCTTAC GGCATAGGCG ATGAGGAGCA TGATCAGGAA      1080

GGCCGGGTGA TTGTGGCTGA ATTTGACTCG TTTGTGCTGG TAACAGCATA TGTACCTAAT      1140

GCAGGCCGAG GTCTGGTACG ACTGGAGTAC CGGCAGCGCT GGGATGAAGC CTTTCGCAAG      1200

TTCCTGAAGG GCCTGGCTTC CCGAAAGCCC CTTGTGCTGT GTGGAGACCT CAATGTGGCA      1260

CATGAAGAAA TTGACCTTCG CAACCCCAAG GGGAACAAAA AGAATGCTGG CTTCACGCCA      1320

CAAGAGCGCC AAGGCTTCGG GGAATTACTG CAGGCTGTGC CACTGGCTGA CAGCTTTAGG      1380

CACCTCTACC CCAACACACC CTATGCCTAC ACCTTTTGGA CTTATATGAT GAATGCTCGA      1440

TCCAAGAATG TTGGTTGGCG CCTTGATTAC TTTTTGTTGT CCCACTCTCT GTTACCTGCA      1500

TTGTGTGACA GCAAGATCCG TTCCAAGGCC CTCGGCAGTG ATCACTGTCC TATCACCCTA      1560

TACCTAGCAC TGTGA                                                      1575
```

(2) INFORMATION FOR SEQ ID NO: 2:

(i) SEQUENCE CHARACTERISTICS:
       (A) LENGTH: 524 amino acids
       (B) TYPE: amino acid
       (C) STRANDEDNESS:

(D) TOPOLOGY: linear (xi) SEQUENCE DESCRIPTION: SEQ ID NO: 2:

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
                20                  25                  30

Leu Leu Gly Lys Gly Thr Ser Ala Ala Asp Ala Val Glu Val Pro Ala
            35                  40                  45

Pro Ala Ala Val Leu Gly Gly Pro Glu Pro Leu Met Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
                100                 105                 110

Ser Tyr Gln Gln Leu Ala Ala Leu Ala Gly Asn Pro Lys Ala Ala Arg
                115                 120                 125

Ala Val Gly Gly Ala Met Arg Gly Asn Pro Val Pro Ile Leu Ile Pro
130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
                180                 185                 190

Lys Gly Ala Gly Ala Thr Ser Gly Ser Pro Pro Ala Gly Arg Asn Pro
                195                 200                 205

Lys Arg Gly Lys Lys Gly Ala Val Ala Glu Asp Gly Asp Glu Leu Arg
                210                 215                 220

Thr Glu Pro Glu Ala Lys Lys Ser Lys Thr Ala Ala Lys Lys Asn Asp
225                 230                 235                 240

Lys Glu Ala Ala Gly Glu Gly Pro Ala Leu Tyr Glu Asp Pro Pro Asp
                245                 250                 255

Gln Lys Thr Ser Pro Ser Gly Lys Pro Ala Thr Leu Lys Ile Cys Ser
                260                 265                 270

Trp Asn Val Asp Gly Leu Arg Ala Trp Ile Lys Lys Lys Gly Leu Asp
                275                 280                 285

Trp Val Lys Glu Glu Ala Pro Asp Ile Leu Cys Leu Gln Glu Thr Lys
                290                 295                 300

Cys Ser Glu Asn Lys Leu Pro Ala Glu Leu Gln Glu Leu Pro Gly Leu
305                 310                 315                 320

Ser His Gln Tyr Trp Ser Ala Pro Ser Asp Lys Glu Gly Tyr Ser Gly
                325                 330                 335

Val Gly Leu Leu Ser Arg Gln Cys Pro Leu Lys Val Ser Tyr Gly Ile
                340                 345                 350

Gly Asp Glu Glu His Asp Gln Glu Gly Arg Val Ile Val Ala Glu Phe
                355                 360                 365

Asp Ser Phe Val Leu Val Thr Ala Tyr Val Pro Asn Ala Gly Arg Gly
                370                 375                 380

Leu Val Arg Leu Glu Tyr Arg Gln Arg Trp Asp Glu Ala Phe Arg Lys
385                 390                 395                 400
```

```
Phe Leu Lys Gly Leu Ala Ser Arg Lys Pro Leu Val Leu Cys Gly Asp
                405                 410                 415
Leu Asn Val Ala His Glu Glu Ile Asp Leu Arg Asn Pro Lys Gly Asn
            420                 425                 430
Lys Lys Asn Ala Gly Phe Thr Pro Gln Glu Arg Gln Gly Phe Gly Glu
        435                 440                 445
Leu Leu Gln Ala Val Pro Leu Ala Asp Ser Phe Arg His Leu Tyr Pro
    450                 455                 460
Asn Thr Pro Tyr Ala Tyr Thr Phe Trp Thr Tyr Met Met Asn Ala Arg
465                 470                 475                 480
Ser Lys Asn Val Gly Trp Arg Leu Asp Tyr Phe Leu Leu Ser His Ser
                485                 490                 495
Leu Leu Pro Ala Leu Cys Asp Ser Lys Ile Arg Ser Lys Ala Leu Gly
                500                 505                 510
Ser Asp His Cys Pro Ile Thr Leu Tyr Leu Ala Leu
            515                 520
```

(2) INFORMATION FOR SEQ ID NO: 3:

(i) SEQUENCE CHARACTERISTICS:
        (A) LENGTH: 1395 base pairs
        (B) TYPE: nucleic acid
        (C) STRANDEDNESS: single
        (D) TOPOLOGY: linear (xi) SEQUENCE DESCRIPTION: SEQ ID NO: 3:

```
ATGGACAAGG ATTGTGAAAT GAAACGCACC ACACTGGACA GCCCTTTGGG GAAGCTGGAG      60
CTGTCTGGTT GTGAGCAGGG TCTGCACGAA ATAAAGCTCC TGGGCAAGGG GACGTCTGCA     120
GCTGATGCCG TGGAGGTCCC AGCCCCCGCT GCGGTTCTCG GAGGTCCGGA GCCCCTGATG     180
CAGTGCACAG CCTGGCTGAA TGCCTATTTC ACCAGCCCG AGGCTATCGA AGAGTTCCCC      240
GTGCCGGCTC TTCACCATCC CGTTTTCCAG CAAGAGTCGT TCACCAGACA GGTGTTATGG     300
AAGCTGCTGA AGGTTGTGAA ATTCGGAGAA GTGATTTCTT ACCAGCAATT AGCAGCCCTG     360
GCAGGCAACC CCAAAGCCGC GCGAGCAGTG GGAGGAGCAA TGAGAGGCAA TCCTGTCCCC     420
ATCCTCATCC CGTGCCACAG AGTGGTCTGC AGCAGCGGAG CCGTGGGCAA CTACTCCGGA     480
GGACTGGCCG TGAAGGAATG GCTTCTGGCC CATGAAGGCC ACCGGTTGGG GAAGCCAGGC     540
TTGGGAGGGA GCTCAGGTCT GGCAGGGGCC TGGCTCAAGG GAGCGGGAGC TACCTCGGGC     600
TCCCCGCCTG CTGGCCGAAA CCTCAAGATC TGCTCTTGGA ATGTGGATGG GCTTCGAGCC     660
TGGATTAAGA GAAAGGATT AGATTGGGTA AAGGAAGAAG CCCCAGATAT ACTGTGCCTT     720
CAAGAGACCA AATGTTCAGA GAACAAACTA CCAGCTGAAC TTCAGGAGCT GCCTGGACTC     780
TCTCATCAAT ACTGGTCAGC TCCTTCGGAC AAGGAAGGGT ACAGTGGCGT GGGCCTGCTT     840
TCCCGCCAGT GCCCACTCAA AGTTTCTTAC GGCATAGGCG ATGAGGAGCA TGATCAGGAA     900
GGCCGGGTGA TTGTGGCTGA ATTTGACTCG TTTGTGCTGG TAACAGCATA TGTACCTAAT     960
GCAGGCCGAG GTCTGGTACG ACTGGAGTAC CGGCAGCGCT GGGATGAAGC CTTTCGCAAG    1020
TTCCTGAAGG GCCTGGCTTC CCGAAAGCCC CTTGTGCTGT GTGGAGACCT CAATGTGGCA    1080
CATGAAGAAA TTGACCTTCG CAACCCCAAG GGGAACAAAA GAATGCTGG CTTCACGCCA     1140
CAAGAGCGCC AAGGCTTCGG GGAATTACTG CAGGCTGTGC CACTGGCTGA CAGCTTTAGG    1200
CACCTCTACC CCAACACACC CTATGCCTAC ACCTTTTGGA CTTATATGAT GAATGCTCGA    1260
TCCAAGAATG TTGGTTGGCG CCTTGATTAC TTTTTGTTGT CCCACTCTCT GTTACCTGCA    1320
```

TTGTGTGACA GCAAGATCCG TTCCAAGGCC CTCGGCAGTG ATCACTGTCC TATCACCCTA 1380

TACCTAGCAC TGTGA 1395

(2) INFORMATION FOR SEQ ID NO: 4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 4:

CCGCCTGCTG GCCGAAACCA TGATCAGGAA GGCCGG 36

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 5:

ATCGTCACCC CCGCTTTG 18

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 6:

GGCCTGTGTG TCCTGCTC 18

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

ATGTGTGCTA TAAACAAAGC T 21

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 8:

TGAAATGCTG TTCCGGGATG C 21

(2) INFORMATION FOR SEQ ID NO: 9:

(i) SEQUENCE CHARACTERISTICS:
        (A) LENGTH: 835 base pairs
        (B) TYPE: nucleic acid
        (C) STRANDEDNESS: single
        (D) TOPOLOGY: linear (xi) SEQUENCE DESCRIPTION: SEQ ID NO: 9:

```
GAATTCGGCA CGAGGCCCGC GCCCCTAGAA CGCTTTGCGT CCCGACGCCC GCAGGTCCTC        60

GCGGTGCGCA CCGTTTGCGA CTTGGTACTT GGAAAAATGG ACAAGGATTG TGAAATGAAA       120

CGCACCACAC TGGACAGCCC TTTGGGAAG CTGGAGCTGT CTGGTTGTGA GCAGGGTCTG        180

CACGAAATAA AGCTCCTGGG CAAGGGGACG TCTGCAGCTG ATGCCGTGGA GGTCCCAGCC       240

CCCGCTGCGG TTCTCGGAGG TCCGGAGCCC CTGATGCAGT GCACAGCCTG GCTGAATGCC       300

TATTTCCACC AGCCCGAGGC TATCGAAGAG TTCCCCGTGC CGGCTCTTCA CCATCCCGTT       360

TTCCAGCAAG AGTCGTTCAC CAGACAGGTG TTATGGAAGC TGCTGAAGGT TGTGAAATTC       420

GGAGAAGTGA TTTCTTACCA GCAATTAGCA GCCCTGGCAG GCAACCCCAA AGCCGCGCGA       480

GCAGTGGGAG GAGCAATGAG AGGCAATCCT GTCCCCATCC TCATCCCGTG CCACAGAGTG       540

GTCTGCAGCA GCGGAGCCGT GGGCAACTAC TCCGGAGGAC TGGCCGTGAA GGAATGGCTT       600

CTGGCCCATG AAGGCCACCG GTTGGGGAAG CCAGGCTTGG GAGGGAGCTC AGGTCTGGCA       660

GGGGCCTGGC TCAAGGGAGC GGGAGCTACC TCGGGCTCCC CGCCTGCTGG CCGAAACTGA       720

GTATGTGCAG TAGGATGGAT GTTTGAGCGA CACACACGTG TAACACTGCA TCGGATGCGG       780

GGCGTGGAGG CACCGCTGTA TTAAAGGAAG TGGCAGTGTC CCTCGTGCCG AATTC           835
```

(2) INFORMATION FOR SEQ ID NO: 10:

(i) SEQUENCE CHARACTERISTICS:
        (A) LENGTH: 207 amino acids
        (B) TYPE: amino acid
        (C) STRANDEDNESS:
        (D) TOPOLOGY: linear (xi) SEQUENCE DESCRIPTION: SEQ ID NO: 10:

```
Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Val Leu Gly Gly Pro Glu Pro Leu Met Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125

Ala Val Gly Gly Ala Met Arg Gly Asn Pro Val Pro Ile Leu Ile Pro
    130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Gly Leu Ala Gly Ala Trp Leu
            180                 185                 190

Lys Gly Ala Gly Ala Thr Ser Gly Ser Pro Pro Ala Gly Arg Asn
        195                 200                 205
```

(2) INFORMATION FOR SEQ ID NO: 11:

(i) SEQUENCE CHARACTERISTICS:
        (A) LENGTH: 1279 base pairs
        (B) TYPE: nucleic acid
        (C) STRANDEDNESS: single
        (D) TOPOLOGY: linear (xi) SEQUENCE DESCRIPTION: SEQ ID NO: 11:

```
GAATTCGGGG GTTGCTCTTT TGCTCATAAG AGGGGCTTCG CTGGCAGTCT GAACGGCAAG      60

CCGGTAAAAA TATTGCTTCG GTGGGTGACG CGGTACAGCT GCCCAAGGGG TTCGTAACGG     120

GAATGCCGAA GCGTGGGAAA AAGGGAGCGG TGGCGGAAGA CGGGGATGAG CTCAGGACAG     180

AGCCAGAGGC CAAGAAGAGT AAGACGGCCG CAAAGAAAAA TGACAAAGAG GCAGCAGGAG     240

AGGGCCCAGC CCTGTATGAG GACCCCCCAG ATCAGAAAAC CTCACCCAGT GCGAAACCTG     300

CCACACTCAA GATCTGCTCT TGGAATGTGG ATGGGCTTCG AGCCTGGATT AAGAAGAAAG     360

GATTAGATTG GGTAAAGGAA GAAGCCCCAG ATATACTGTG CCTTCAAGAG ACCAAATGTT     420

CAGAGAACAA ACTACCAGCT GAACTTCAGG AGCTGCCTGG ACTCTCTCAT CAATACTGGT     480

CAGCTCCTTC GGACAAGGAA GGGTACAGTG GCGTGGGCCT GCTTTCCCGC CAGTGCCCAC     540

TCAAAGTTTC TTACGGCATA GGCGATGAGG AGCATGATCA GGAAGGCCGG GTGATTGTGG     600

CTGAATTTGA CTCGTTTGTG CTGGTAACAG CATATGTACC TAATGCAGGC CGAGGTCTGG     660

TACGACTGGA GTACCGGCAG CGCTGGGATG AAGCCTTTCG CAAGTTCCTG AAGGGCTGG      720

CTTCCCGAAA GCCCCTTGTG CTGTGTGGAG ACCTCAATGT GGCACATGAA GAAATTGACC     780

TTCGCAACCC CAAGGGGAAC AAAAAGAATG CTGGCTTCAC GCCACAAGAG CGCCAAGGCT     840

TCGGGGAATT ACTGCAGGCT GTGCCACTGG CTGACAGCTT TAGGCACCTC TACCCCAACA     900

CACCCTATGC CTACACCTTT TGGACTTATA TGATGAATGC TCGATCCAAG AATGTTGGTT     960

GGCGCCTTGA TTACTTTTTG TTGTCCCACT CTCTGTTACC TGCATTGTGT GACAGCAAGA    1020

TCCGTTCCAA GGCCCTCGCG AGTGATCACT GTCCTATCAC CCTATACCTA GCACTGTGAC    1080

ACCACCCCTA AATCACTTTG AGCCTGGGAA ATAAGCCCCC TCAACTACCA TTCCTTCTTT    1140

AAACACTCTT CAGAGAAATC TGCATTCTAT TTCTCATGTA TAAAACGAGG AATCCTCCAA    1200

CCAGGCTCCT GTGATAGAGT TCTTTTAAGC CCAAGATTTT TTATTTGAGG GTTTTTTGTT    1260

TTTTAAAAAA CCCGAATTC                                                 1279
```

(2) INFORMATION FOR SEQ ID NO: 12:

(i) SEQUENCE CHARACTERISTICS:
        (A) LENGTH: 318 amino acids
        (B) TYPE: amino acid
        (C) STRANDEDNESS:
        (D) TOPOLOGY: linear (xi) SEQUENCE DESCRIPTION: SEQ ID NO: 12:

```
Met Pro Lys Arg Gly Lys Lys Gly Ala Val Ala Glu Asp Gly Asp Glu
 1               5                  10                  15

Leu Arg Thr Glu Pro Glu Ala Lys Lys Ser Lys Thr Ala Ala Lys Lys
                20                  25                  30

Asn Asp Lys Glu Ala Ala Gly Glu Gly Pro Ala Leu Tyr Glu Asp Pro
            35                  40                  45

Pro Asp Gln Lys Thr Ser Pro Ser Ala Lys Pro Ala Thr Leu Lys Ile
        50                  55                  60

Cys Ser Trp Asn Val Asp Gly Leu Arg Ala Trp Ile Lys Lys Lys Gly
```

```
                65                  70                  75                  80
Leu Asp Trp Val Lys Glu Glu Ala Pro Asp Ile Leu Cys Leu Gln Glu
                        85                  90                  95
Thr Lys Cys Ser Glu Asn Lys Leu Pro Ala Glu Leu Gln Glu Leu Pro
                100                 105                 110
Gly Leu Ser His Gln Tyr Trp Ser Ala Pro Ser Asp Lys Glu Gly Tyr
            115                 120                 125
Ser Gly Val Gly Leu Leu Ser Arg Gln Cys Pro Leu Lys Val Ser Tyr
        130                 135                 140
Gly Ile Gly Asp Glu Glu His Asp Gln Glu Gly Arg Val Ile Val Ala
145                 150                 155                 160
Glu Phe Asp Ser Phe Val Leu Val Thr Ala Tyr Val Pro Asn Ala Gly
                165                 170                 175
Arg Gly Leu Val Arg Leu Glu Tyr Arg Gln Arg Trp Asp Glu Ala Phe
            180                 185                 190
Arg Lys Phe Leu Lys Gly Leu Ala Ser Arg Lys Pro Leu Val Leu Cys
        195                 200                 205
Gly Asp Leu Asn Val Ala His Glu Glu Ile Asp Leu Arg Asn Pro Lys
    210                 215                 220
Gly Asn Lys Lys Asn Ala Gly Phe Thr Pro Gln Glu Arg Gln Gly Phe
225                 230                 235                 240
Gly Glu Leu Leu Gln Ala Val Pro Leu Ala Asp Ser Phe Arg His Leu
                245                 250                 255
Tyr Pro Asn Thr Pro Tyr Ala Tyr Thr Phe Trp Thr Tyr Met Met Asn
            260                 265                 270
Ala Arg Ser Lys Asn Val Gly Trp Arg Leu Asp Tyr Phe Leu Leu Ser
        275                 280                 285
His Ser Leu Leu Pro Ala Leu Cys Asp Ser Lys Ile Arg Ser Lys Ala
    290                 295                 300
Leu Ala Ser Asp His Cys Pro Ile Thr Leu Tyr Leu Ala Leu
305                 310                 315
```

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 13:

CCGGAATTCA TGGACAAGGA TTGT                                         24

(2) INFORMATION FOR SEQ ID NO: 14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 14:

CTTTTTCCCA CGCTTCGGGT TTCGGCCAGC AGGCGG                          36

(2) INFORMATION FOR SEQ ID NO: 15:

(i) SEQUENCE CHARACTERISTICS:
        (A) LENGTH: 36 base pairs
        (B) TYPE: nucleic acid

```
          (C) STRANDEDNESS: single
          (D) TOPOLOGY: linear (xi) SEQUENCE DESCRIPTION: SEQ ID NO: 15:

CCGCCTGCTG GCCGAAACCC GAAGCGTGGG AAAAAG                                        36

(2) INFORMATION FOR SEQ ID NO: 16:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO: 16:

GGCCGTCGAC ATCACAGTGC TAGG                                                     24
```

DNA SEQUENCES ENCODING FUSIONS OF DNA REPAIR PROTEINS AND USES THEREOF

This is a continuation of application Ser. No. 08/957,302 filed Oct. 24, 1997, now U.S. Pat. No. 6,046,036, which claims priority to U.S. Provisional Ser. No. 60/029,308, filed Oct. 25, 1996.

BACKGROUND OF THE INVENTION

The entire text of the above-referenced disclosure is specifically incorporated by reference herein without disclaimer.

1. Field of the Invention

The present invention relates generally to the field of molecular biology, and more particularly, DNA repair. In specific embodiments, the invention relates to DNA sequences encoding fusions of DNA repair proteins having complementary functions, and to the use of such DNA sequences to enhance the survival of cells when subjected to DNA-damaging agents such as chemotherapeutics.

2. Description of Related Art

The use of multiagent chemotherapy protocols has produced dramatic increases in the survival rates of many cancers. Pediatric cancers have been particularly amenable to treatments utilizing multiagent and multimodality approaches. In addition, dose intensification has been increasingly utilized in attempts to increase survival rates of both adult and pediatric cancers. DNA alkylating agents have been an important part of most dose-intensification protocols.

The positive impact of increased dose intensity of therapy on response rate and survival duration has been demonstrated in childhood Burkitt's lymphoma, metastatic breast cancer, neuroblastoma, testicular cancer and osteogenic and Ewing's sarcoma (Broun et al., 1992; Schwenn et al., 1991; Cheung and Heller, 1991; Smith et al., 1991) and most recently in childhood acute myelocytic leukemia (Woods et al., 1996). Invariably, and in spite of the increasing use of myeloid growth factor support, myelosuppression is a major impediment to further dose-intensification in humans. This is particularly true in patients with relapsed disease previously treated with intensive chemotherapy as initial therapy.

One approach to circumvent the dose-limiting myeloid toxicities of chemotherapy agents has been the use of recombinant vectors to introduce and express various genes important in chemotherapy resistance in bone marrow-derived cells (Moritz and Williams, 1996). The majority of work in this area has been focused on the use of recombinant retrovirus vectors. Gene transfer has been accomplished using several different DNA sequences, including dihydrofolate reductase (DHFR) or DHFR mutants encoding resistance to methotrexate (Williams et al., 1987; Miller et al., 1984; Li et al., 1994; Corey et al., 1990), p-glycoprotein multidrug resistance (MDR-1) gene encoding resistance to several alkylating agents (Hanania and Deisseroth, 1994), glutathione-dependent enzymes encoding resistance to alkylating agents and ionizing radiation (Greenbaum et al., 1994) and cytosolic aldehyde dehydrogenase encoding resistance to cyclophosphamide (Magni et al., 1996). More recently, work has been concentrated on retroviral vectors encoding the DNA repair protein 0-6-methylguanine-DNA methyltransferase (MGMT) as a mechanism to generate resistance to chloroethylnitrosourea (CENUs) and other alkylating agents (Moritz et al., 1993; Moritz et al., 1995; Maze et al., 1996).

Chloro-ethyl-nitrosoureas (CENUs) have been shown to be effective agents in treatment of several human cancers, particularly brain tumors. A major determinant of CENU-induced cytotoxicity is the alkylation of guanine at the $O^6$-position and the formation of interstrand DNA crosslinks. While alkylation at the $O^6$-position primarily induces G:C to A:T transition, interstrand DNA crosslinks are particularly cytotoxic because they disrupt DNA replication (Toorchen and Topel, 1983). CENU-induced DNA adducts, such as a chloroethyl group at the $O^6$-position, can initiate the subsequent formation of an interstrand crosslink by rearranging to produce an ethyl bridge between N1 of guanine and N3 of cytosine in the opposite strand (Ludlum, 1980). Repair of this lesion is distinct, since it involves direct reversal of the damaged adduct by the mammalian protein MGMT (Erickson et al., 1980; Robins et al., 1983; Samson et al., 1986; Brent and Remack, 1988).

MGMT transfers the chloroethyl group from guanine to an internal cysteine residue located within the acceptor site of the MGMT protein and thus repairs the modified base prior to the formation of the interstrand crosslink (Saffhill et al., 1985; Pegg et al., 1995). In most cases, the level of MGMT protein in mammalian cells correlates with CENU sensitivity (Erickson et al., 1980; Pegg et al., 1995; Lindahl et al., 1988). The amount of MGMT protein expressed in human and murine bone marrow cells is considerably lower than in other tissues and contributes to the inefficient repair of CENU-induced DNA damage in blood cells (Moritz et al., 1995; Gerson et al., 1985). Thus increased expression of MGMT via gene transfer provides a unique opportunity to effect drug resistance by increasing the expression of an endogenous protein.

Several laboratories have demonstrated that transduction of murine or human hematopoietic stem and/or progenitor cells, via a retroviral vector encoding the human MGMT cDNA, protects bone marrow cells from CENU-induced myelotoxicity (Moritz et al., 1995; Maze et al., 1996; Allay et al., 1995; Jelinek et al., 1996; Wang et al., 1996). In previous studies, a model of CENU-induced fatal bone marrow suppression was developed (Maze et al., 1994). Reconstitution of murine bone marrow with hematopoietic stem cells expressing vector-derived MGMT protected mice from 1,3, Bis (2-chloroethyl)-nitrosurea (BCNU)-induced bone marrow hypoplasia and peripheral blood pancytopenia (Moritz et al., 1995; Maze et al., 1996). Bone marrow cells harvested from these mice were more resistant to BCNU in vitro and demonstrated a higher level of MGMT DNA repair activity compared to BCNU-treated mock-infected control mice (Maze et al., 1996). In addition, a significant reduction in short-term CENU-related mortality was observed in BCNU-treated mice transplanted with MGMT-expressing hematopoietic stem cells (Maze et al., 1996).

In light of the foregoing discussion, it is clear that there is a limitation with current chemotherapies in that the ability to increase doses of chemotherapy used to treat cancer patients is inhibited by the cytotoxicity of the chemotherapeutic agents on various non-target organ systems including the bone marrow. If DNA repair genes that protect against the deleterious effects of chemotherapeutic agents with oxidative damaging capacity can be inserted into the patient's bone marrow cells, or other organ systems prone to damage by these agents (such as lung), these systems can be protected and possibly the dose of treatment increased to rid the system of the cancer. Furthermore, although this idea has been tested with the MGMT gene, this gene is only limited to repairing the $O^6$ guanine lesion that occurs from various chemotherapeutic agents, especially the chloronitrosoureas.

However, a large number of chemotherapeutic agents also cause damage at other nucleophilic sites in the DNA, such as $N^7$-guanine, $N^3$-adenine, etc. Furthermore, a number of these agents also are oxidative DNA damaging agents and can have deleterious effects on the patient via this pathway. In light of the foregoing, it is evident that there remains a need for improved methods for enhancing the protection of non-target cells when prone to or subjected to DNA-damaging agents, such as chemotherapeutic agents or in malignant conditions such as Fanconi's anemia. The present invention is addressed to these needs.

SUMMARY OF THE INVENTION

In order to address the deficiencies in the prior art, the present invention provides a DNA sequence encoding a fusion protein having two DNA repair proteins fused to one another. Advantageously, the resulting fusion protein when expressed in cells will enhance the survival of the cells greater than that provided by the expression of either protein alone. In accordance with the invention, the fusions can be achieved with or without the use of a peptide sequence linker.

Thus, there is provided a fusion protein having DNA repair activity comprising a first DNA repair protein fused to second DNA repair protein. In preferred embodiments, the first repair protein is a direct reversal repair pathway enzyme and the second repair protein is a base excision repair enzyme. In certain embodiments, the second repair protein is from the base excision repair-A pathway. In certain other embodiments, the second repair protein is from the base excision repair-B pathway.

In more particular embodiments, the second repair protein may be selected from the group consisting of MPG, HAAG, APE, APN-1, β-polymerase, and DNA ligase. In yet other embodiments, the second repair protein may be selected from the group consisting of fpg, dS3, OGG1, EndoIII, EndoIV, exoIII, NTG-1, NTG-2, SCR-1, and SCR-2.

In another preferred embodiment, the first repair protein is selected from the group consisting of hAPE, APN-1, NTG-1, NTG-2, SCR-1, SCR-2, exoIII, endoIV, endoIII, hMPG, fpg, dS3, β-polymerase, DNA ligase, HAAG, OGG1 and hMGMT and said second DNA repair protein is selected from the group consisting of hAPE, APN-1, NTG-1, NTG-2, SCR-1, SCR-2, exoIII, endoIV, endoIII, hMPG, fpg, dS3, β-polymerase, DNA ligase, HAAG, OGG1 and hMGMT, such that said first DNA repair protein is different from said second DNA repair protein. In yet another embodiments, the fusion protein may, further comprise a third DNA repair protein wherein said third DNA repair protein is a base excision repair protein. In a particularly preferred embodiment, the first protein is hMGMT. In yet another preferred embodiment, the second protein comprises hAPE. In a more preferred embodiment, the first protein is hMGMT and the second protein is hAPE. In certain embodiments, the fusion protein of the present invention has the sequence of SEQ ID NO:2.

In another aspect of the present invention, there is provided an isolated nucleic acid comprising a nucleic acid segment coding for a fusion protein having DNA repair activity comprising a first repair protein fused to second fusion protein. In preferred embodiments, the first repair protein is a direct reversal repair pathway enzyme and the second repair protein is a base excision repair enzyme. In other embodiments, the nucleic acid is selected from the group consisting of genomic DNA, complementary DNA and RNA. In particularly preferred embodiments, the nucleic acid has a sequence as set forth in SEQ ID NO:1. In still further embodiments, the nucleic acid is a complementary DNA and further comprises a promoter operably linked to said nucleic acid segment, or the complement thereof, encoding said fusion protein. In particular embodiments, the promoter may be selected from the group consisting of CMV IE, PGK, SV40, MLP, AdE1, SPC, and β-ACTIN. In certain other embodiments, the nucleic acid is linked to a selectable marker. In yet other embodiments, the nucleic acid may further comprise a polyadenylation signal operably linked to said nucleic acid segment. The nucleic acid may comprise an origin of replication.

In particular embodiments, the nucleic acid may be in a viral vector selected from the group consisting of retrovirus, adenovirus, herpesvirus, vaccinia virus and adeno-associated virus. The nucleic acid may be packaged in a virus particle, in alternate embodiments, the nucleic acid may be packaged in a liposome.

The present invention also provides an expression construct comprising a vector comprising an isolated polynucleotide encoding a fusion protein having DNA repair activity and a promoter operably linked to said isolated polynucleotide, wherein said fusion protein comprises a first DNA repair protein fused to second DNA repair protein. In certain embodiments, the vector is a viral vector. In particular embodiments, the viral vector may be selected from the group consisting of a retroviral vector, an adenoviral vector, a herpesviral vector, adeno-associated viral vector and a cytomegaloviral vector. In more particular embodiments, the viral vector further comprises a polyadenylation signal. In specific embodiments, the fusion protein has an amino acid sequence as set forth in SEQ ID NO:2.

In another aspect, the present invention provides a recombinant host cell comprising a vector having an expression region encoding a fusion protein having DNA repair activity operatively linked to a promoter, wherein said fusion protein comprises a first DNA repair protein fused to second DNA repair protein.

The present invention also provides a method of inhibiting the action of chemotherapy agents in non-target cells comprising contacting said cell with a composition comprising a fusion protein having DNA repair activity. In more particular embodiments, the inhibiting comprises contacting said cell with a vector comprising an expression cassette comprising a gene encoding a fusion protein having DNA repair activity operatively linked to a promoter wherein said protein comprises comprising a first DNA repair protein fused to second DNA repair protein; wherein expression of said fusion protein prevents DNA damage in said cell. In specific embodiments, the protein has an amino acid sequence as set forth in SEQ ID NO:2.

Also provided is a method of facilitating an increase in the dosage of chemotherapy being administered to a subject with a disease comprising the steps of providing a vector comprising an expression cassette comprising a gene construct encoding a fusion protein having DNA repair activity and a promoter active in eukaryotic cells, wherein said gene construct is operably linked to said promoter, wherein said fusion protein comprises a first DNA repair protein fused to second DNA repair protein; contacting said vector with said subject under conditions permitting uptake of said vector by said subject; wherein expression of said protein in said subject allows for increasing the dose of chemotherapy agent above the amount that can be tolerated in the absence of such DNA repair activity to effect treatment of said disease.

Another aspect of the present invention contemplates a pharmaceutical composition comprising a vector construct comprising an expression region encoding a fusion protein having DNA repair activity under the control of a eukaryotic promoter; and a pharmaceutically acceptable carrier, excipient or diluent wherein said fusion protein comprises a first DNA repair protein fused to second DNA repair protein.

The present invention provides a method of protecting bone cells from chemotherapy comprising administering a composition comprising a fusion protein having DNA repair activity in an amount effective to prevent DNA damage of said cells. In certain embodiments, the composition comprises a vector construct comprising an expression region encoding a fusion protein having DNA repair activity under the control of a eukaryotic promoter, wherein said fusion protein comprises a first DNA repair protein fused to second DNA repair protein.

In another embodiment, there is provided a method for preparing a cell culture resistant to DNA damage, comprising the steps of providing a culture of cells; transfecting said cells with a nucleic acid segment gene encoding a fusion protein comprising a first DNA repair protein fused to a second DNA repair protein wherein said nucleic acid segment is operatively linked to a promoter; and selecting cells that produce said fusion protein. In particular embodiments, the cells may be hematopoietic cells, lung cells, brain cells or hepatocytes, including and expressing a DNA sequence encoding a fusion protein of the invention as described above.

A related embodiment of the invention concerns a hematopoietic cellular culture enriched in hematopoietic stem and progenitor cells, wherein cells of the culture express a DNA sequence encoding a fusion protein of the invention as described above. Thus, a preferred embodiment provides a method of providing a cellular graft to a mammal comprising the steps of obtaining a population of hematopoietic cells; transfecting said cell with a gene construct encoding a fusion protein comprising a first DNA repair protein fused to a second DNA repair protein wherein said gene is operatively linked to a promoter; and; administering said transfected cells to a subject in an amount effective to establish a population of haematopoeitic cells in said subject, wherein the risk of DNA damage in said mammal is reduced due to the administration of said cells. In particular aspects, the cells may be administered in combination of chemotherapy agents.

Still another preferred embodiment of the invention relates to a method for preparing a protected hematopoietic cellular culture, comprising providing a culture of hematopoietic cells and transforming cells of the culture with a recombinant vector including a DNA sequence encoding a fusion protein of the invention as described above.

The present invention also provides a cellular grafting method which includes the step of administering to a mammal hematopoietic cells expressing a DNA sequence encoding a fusion protein of the invention as described above.

Still other preferred embodiments of the invention provide transgenic, non-human mammals in which cells include recombinant DNA encoding a DNA repair protein, or encoding a fusion protein including at least two DNA repair proteins.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. The PCR™ product was subcloned into pGEX for sequencing and protein overproduction for biochemical analysis. The chimeric MGMT-APE fragment was then excised and cloned into MSCV2.1 retroviral backbone. The MGMT-d151APE is a chimeric fusion protein with MGMT activity with but no APE activity. FIG. 1B. MGMT-APE and MGMTd151APE constructs. The various domains of the chimeric proteins are shown, including landmark domains of the APE protein. NLS=nuclear localization signal; Redox=domain involved in redox function in APE; Cys 65=cysteine involved in redox activity; Glu-96 Asp-283 and His-309=amino acids presumed to be involved in the active site of APE.

FIG. 3A. Incubations with the GST-hAPE (lanes 2–4) or GST-MGMT-hAPE (lanes 6–8) containing 50 pg, 100 pg, and 200 pg respectively. Lane 1 AP-37 mer; lane 5 hot piperidine treatment of AP 37 mer to generate a β, δ elimination product. FIG. 3B. Loss ofd activity for d151 is not due to the presence of MGMT. Both hAPE and d151APE were overexpressed in $E.\ coli$ as fusions with GST. Incubations with GST-hAPE contained total protein amounts of 50 pg, 100 pg, and 200 pg, respectively, whereas GST-d151APE (lane 6–8) contained 50 ng, 100 ng, and 200 ng respectively. Lane 1, AP-37 mer; lane 5 hot piperdine treatment of AP-37 mer to generate β, δ elimination product.

FIG. 4A The MMS gradient was from 0–4 mM MMS. Lane 1 is wild-type $E.\ coli$ (AB1157); lane 2 GST-APE; lane 3 GST-MGMT-APE; lane 4, GST-d151APE; lane 5 GST-MGMT-d151APE; lane 6 RPC501 (xth⁻, nfo-1⁻) cells alone. The length of cell growth is a measure of resistance to the agent. FIG. 4B. $H_2O_2$ gradient plate assay (0–0.2 mM $H_2O_2$). Lane 1 is wild-type $E.\ coli$; lane 2 GST-MGMT-APE; lane 3, GST-MGMT-d151APE; lane 4 RPC501 (xth⁻, nfo-1⁻) cells alone. The constructs in lanes 2–3 are in RPC501 cells.

FIG. 9C shows the survival of NIH/3T3 transfectants after exposure to bleomycin. The cells were transfected with PGK-APN1 or PGK-APE.

FIG. 20A shows protection of NIH3T3 cells with the E. coli fpg and endo III genes in the MSCV retroviral vector. The fpg-NLS is the fpg gene with the SV40 nuclear localization signal added at the amino end of the protein. FIG. 20B Expression of E.coli fpg is associated with increased resistance to thiotepa; results of three independent studies are shown.

FIG. 21A BER pathway A is a pathway involving DNA glycosylase action of MPG, followed by endonuclease activity of for example APE or APN-1. The product of this reaction is the substrate for a phosphodiesterase (APE or β-polymerase) enzyme which yields an intermediate which forms the substrate for a DNA polymerase and ligase reaction. FIG. 21B BER-B pathway is an alternate pathway for removing and repairing a damaged base (Doetsch and Cunningham, 1990; Wallace, 1988). Removal of the damaged base and incision of the DNA backbone occurs via a single enzyme in contrast to the previously described repair involving separate glycosylase (MPG) and AP endonuclease (APE or APNI).

DESCRIPTION OF ILLUSTRATIVE EMBODIMENTS

Figure 1A:
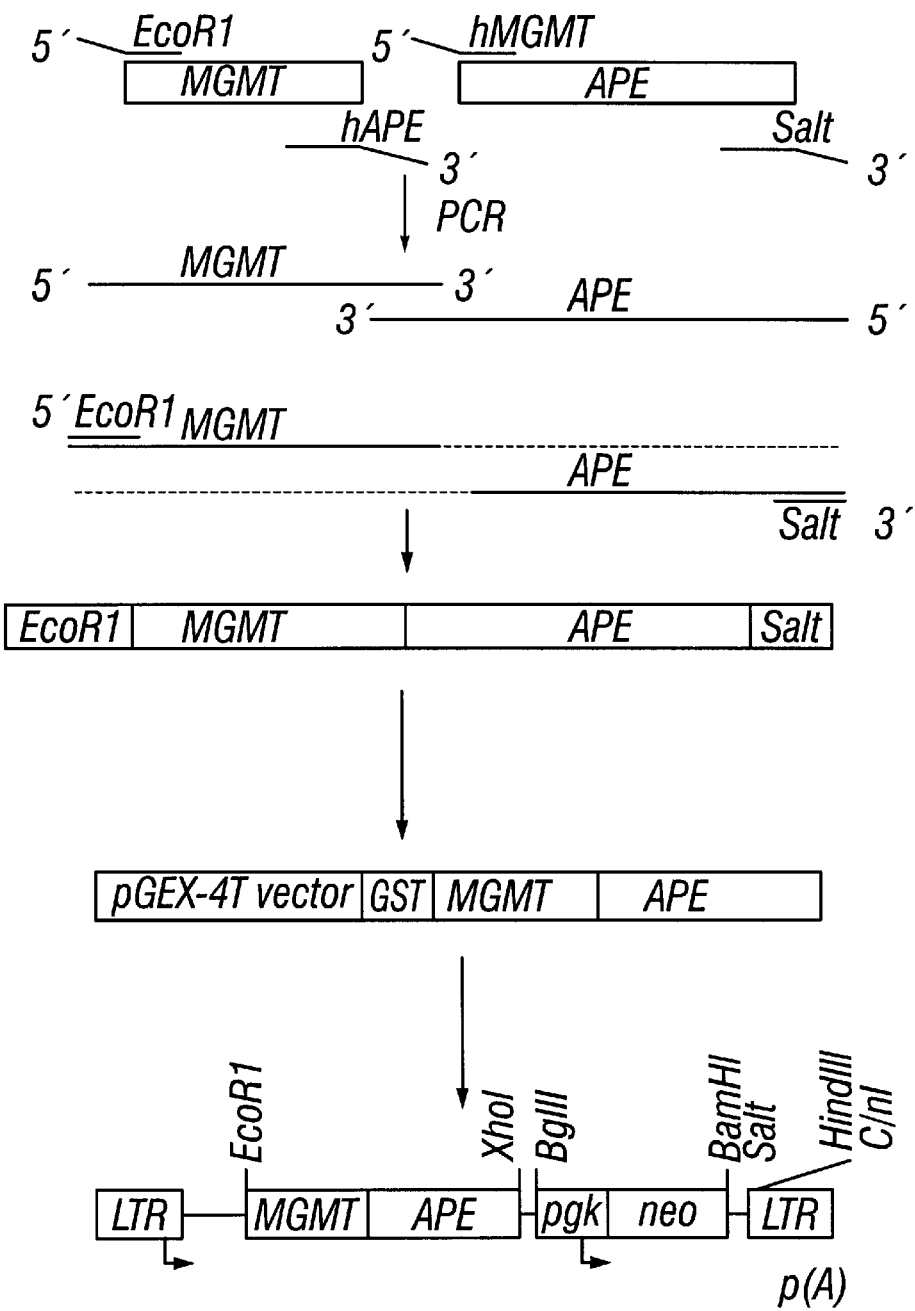
FIG. 1A and FIG. 1B. Construction of the human MGMT-APE fusion construct by the overlapping PCR™ technique.

An unfortunate result associated with certain chemotherapeutic alkylating agents is their toxic effects on non-target tissues. An example of this is the severe bone marrow toxicity induced by 1,3-bis (2-chloroethyl)-1-nitrosourea (BCNU), an agent commonly used to treat lymphomas, breast, lung and gastrointestinal cancers (Carter et al., 1992). The toxicity to bone marrow cells most likely is due to low levels of existing DNA repair activities (Gerson et al., 1986) that would otherwise help to protect cellular DNA from the damaging consequences of BCNU treatment. One strategy to overcome this limited DNA repair capacity is to transduce bone marrow cells with specific genes that encode repair enzymes which act on the DNA lesions produced by BCNU. This recently was accomplished (Maze et al., 1996) with mice bone marrow cells transduced with human methylguanine methyltransferase (hMGMT), an activity that repairs BCNU-generated chloroethyl groups at the $O^6$ position of guanine (Robins et al., 1983; Samson et al., 1986).

Chemotherapeutic alkylating agents are potent mutagens which are capable of forming a number of different adducts by reacting with cellular DNA (Del Rosso et al., 1981; Friedberg et al., 1995). These agents can alkylate all four bases of DNA at the nitrogens or oxygens as well as the sugar phosphates of the DNA backbone. However, the distribution of the adducts at the various sites depends on both the chemical structure of the alkylating agent and the alkyl group itself. One of the sites, $O^6$-methylguanine, as noted above, preferentially pairs with thymine rather than cytosine resulting in a GC to AT transition (Brent and Remack, 1988). $O^4$-methylthymine, also a miscoding base, induces AT to GC transitions (Brent et al., 1988). Another important product of attack on DNA by alkylating agents is $N^3$-methyladenine, which is cytotoxic (Zaharko et al., 1974; Lamar and Palmer, 1984). $N^3$-methyladenine blocks the progress of DNA polymerases during replication (Larson et al., 1985). In addition, N-alkylpurines are indirectly mutagenic because their removal, either in a spontaneous chemical reaction or by the action of DNA glycosylases results in the formation of AP sites. While AP sites normally prevent DNA replication, under special circumstances they can also lead to mutations (Loeb and Preston, 1986). N-alkylpurines may also contribute, simply by accumulating, to other biological effects such as induction of chromosomal aberrations as well as the aging process (Zaharko et al., 1974; Gensler and Bernstein, 1981). DNA lesions created by a variety of alkylating agents are repaired by base excision repair (BER). Other damaged adducts or alterations of DNA that occurs following alkylation involves the ring-opening of DNA bases occurring following alkylation at the $N^7$-position of guanine. For example, N,N',N"-triethylenethiophospharamide (thiotepa) can be hydrolyzed to aziridine which results in the depurination and formation of aminoethyl adducts of guanine and adenine (Gill et al., 1996). $N^7$-aminoethyl guanosine becomes unstable and degrades by imidazole ring opening and depurination. These ring-opened damaged bases are repaired by members of the BER pathway, such as the E. coli fpg, yeast and human OGG1 and Drosophila S3 genes (Mitra et al., 1997; Cunningham, 1996).

Figure 21A:
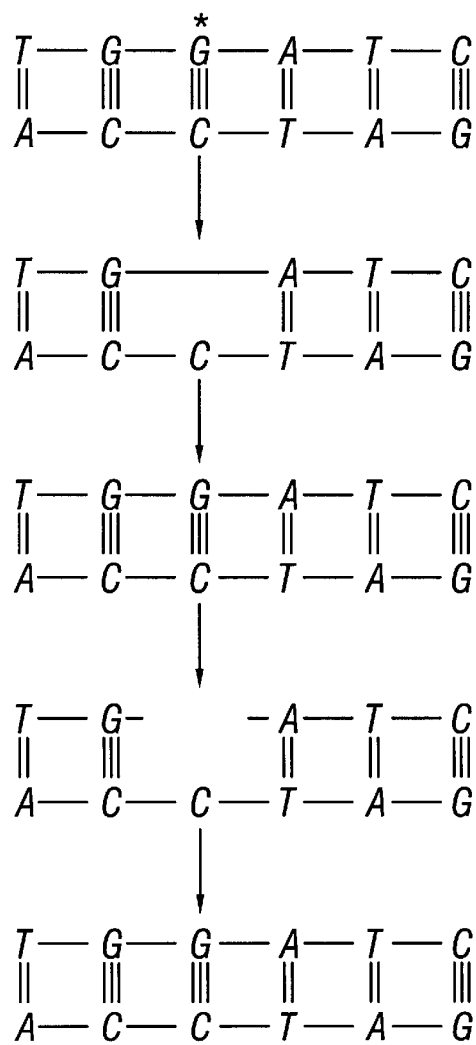
FIG. 21A and FIG. 21B. Pathways of base excision repair (BER).
Figure 21B:
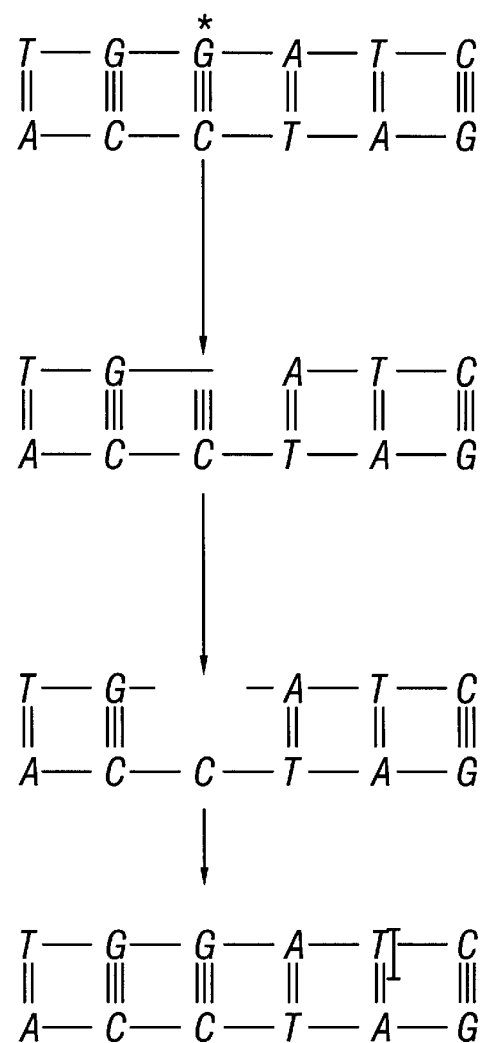

DNA base excision repair (BER) may work through two alternative pathways (FIG. 21A and FIG. 21B). The first involves four enzymes in mammalian cells: DNA glycosylases, such as methylpurine-DNA glycosylase (MPG), apurinic/apyrimidinic (AP) endonucleases (APE or APN-1) (Demple and Harrison, 1994; Doetsch and Cunningham, 1990), DNA β-polymerase (B-Po1) and DNA ligase (FIG. 21A). DNA glycosylases are enzymes that hydrolyze the N-glycosidic bond between the damaged base and the deoxyribose moiety, creating an AP site on the DNA backbone (Wallace, 1988; Sancar and Sancar, 1988). AP sites, whether produced glycosylases or directly by DNA damaging agents (bleomycin) are acted upon by AP endonucleases, which can make an incision either 3' to the AP site (AP lyase) or 5' to the AP site (hydrolytic). The resulting gap in the phosphodiester backbone is filled in by DNA β-polymerase and the ends are ligated by DNA ligase I. The rate-limiting protein in BER pathways may be cell type- and lesion-type specific and no data are currently available with respect to the importance of each component of this pathway in hematopoietic cells.

Previous data has shown that in some cells MPG is not the rate-limiting step in the BER pathway for the repair of alkylation DNA damage (Horton et al., 1995). In vitro studies by Tatsuka et al. have shown that APE is rate-limiting in repair of reactive oxygen species-induced DNA strand breaks. In addition, Tomicic et al. (1997) have recently demonstrated that increased expression of APN-1 protein in mammalian cells by DNA transfection leads to increased resistance to both methyl methanesulfonate (MMS) and $H_2O_2$. APN-1 is the major AP endonuclease involved in repair of oxidative and alkylated bases in yeast (Ramotar et al., 1991).

A second pathway for removing and repairing a damaged base in the BER pathway involves a complex glycosylase associated with AP lyase activity (Doetsch and Cunningham, 1990; Wallace, 1988) (FIG. 21B). Removal of the damaged base and incision of the DNA backbone occurs via a single enzyme in contrast to the previously described repair involving separate glycosylase (MPG) and AP endonuclease (APE or APNI). Examples of combined glycosylase/AP lyases include the E. coli fpg, yeast and human OGG1 and Drosophila S3. The fpg glycosylase/AP lyase recognizes and initiates repair of ring-opened bases such as formamidopyrimidine-Guanine (FaPy-Gua) and methylated formamidopyrimidine ($N^7$-methylformamidopyrimidine; 7-methyl-FaPy-Gua). These lesions are produced by alkylating agents such as thiotepa and by oxidative DNA damaging chemotherapy agents. The human OGG1 genes appear to share functional activities with the E. coli fpg gene in relation to the repair 8oxoG lesions and limited activity on the repair of FaPy-Gua caused by alkylating agents, such as thiotepa. The remainder of the pathway may be similar to the pathway outlined above, except some evidence suggest that the gap-filling DNA polymerase may involve replicative polymerases. Thus, although largely unexplored to date, fpg glycosylase/AP lyase may repair alkylation damage in mammalian cells and may be more efficient in this regard than the mammalian homologues.

Since alkylating agents are known to generate many different types of DNA modifications, added protection to non-target tissues can be achieved by linking hMGMT together with a number of other DNA repair enzymes to form a protein that recognizes a broad spectrum of DNA lesions. As such the present invention links the human AP endonuclease (hAPE) to hMGMT, thereby providing for the repair of not only $O^6$ modifications of guanine, but also an activity directed towards baseless sites and modified 3' termini in DNA as a consequence of BCNU-generated DNA damage. Of course these are exemplary constructs and other enzymes of the BER pathway for example, FPG, OGG1, MPG, HAAG, APN1, SCR, NTG and endoIII may be used in the constructs instead of, or in combination, with hAPE.

The major AP endonuclease in humans (Robson and Hickson, 1991; Demple et al., 1991) has been shown to contain two nonoverlapping domains of activity (Xanthoudakis et al., 1994). One is for the DNA repair activity associated with hAPE, where amino acid sequences at the C-terminus have been concluded to be essential for AP endonuclease activity. Amino acid sequences at the N-terminus, on the other hand, are required for the redox regulation of different transcription factors such as Fos and Jun (Xanthoudakis et al., 1994). This conclusion is supported by the observation that the N-terminal 60 amino acids of hAPE can be deleted without significant loss of AP endonuclease activity (Xanthoudakis et al., 1994).

I. DNA Damage And AP Site Formation

This discussion is directed to the various types of DNA damage that occur, the consequences and cellular mechanisms for dealing with such damage. Some of the most common forms of DNA damage lead to AP site formation. These are: 1) electrophilic agents and ionizing radiation which alter bases and sugars that may be removed by DNA glycosylases (see below) leading to an AP site, 2) UV irradiation; results in cyclobutyl dimers that may be removed leaving AP sites, 3) Free radicals; such as the superoxide radical ($O_2$) and hydroxyl radical ($HO^-$) which are produced by ionizing radiation (Hutchinson, 1985) or hydrogen peroxide ($H_2O_2$) exposure (Imlay and Linn, 1988) and 4) alkylating agents. AP sites arise spontaneously, in which it has been estimated that roughly 20,000 purines and 500 pyrimidines are formed per human cell per day (Lindahl and Nyberg, 1972). The formation of some of these lesions from both endogenous and exogenous sources as they pertain to base excision repair is described below.

A. Endogenous Insults

1. Nonenzymatic DNA Methylation

In addition to the spontaneous forms of DNA damage which can arise under normal physiological conditions, there exist several endogenous mutagenic factors which react with DNA to produce marked structural alterations. One of the best characterized and most important of these factors is S-adenosylmethionine (SAM). SAM normally acts as a efficient methyl group donor in most cellular transmethylation reactions. However, methylation of DNA which yields primarily $N^7$-methylguanine and $N^3$-methyladenine occurs as a minor side reaction of the necessary methyl transfer function of SAM (Barrows and Magee, 1982). Thus, SAM has the same effect as a weak alkylating agent. N7-methylguanine, which does not alter the coding specificity of the base, appears relatively harmless. N3-methyladenine, on the other hand, is a cytotoxic lesion that blocks DNA replication (Karran et al., 1982). SAM induces the formation of the highly mutagenic lesion $O^6$-methylguanine only in trace amounts. Instead, the production of this miscoding base derivative accounts for the very strong mutagenic activity of several other alkylating agents. Recently, in vivo evidence was reported which clearly demonstrates that in *Saccharomyces cerevisiae* endogenous DNA alkylation damage is a source of spontaneous mutation (Xiao and Samson, 1993).

Other cellular compounds represent potential threats to the integrity of genetic material because of their ability to form covalent adducts with DNA. For instance, glucose, glucose-6-phosphate, and possibly other sugars present in a cell have been demonstrated to modify DNA and have been shown to be mutagenic (Bucala et al., 1984; Lorenzi et al, 1986; Lee and Cerami, 1987).

2. DNA Oxidation

DNA damage produced by free radicals probably accounts for the most frequent lesions in cells (Ames, 1983). Ames (1983) estimated that each human cell sustains an average of $10^3$ "oxidative hits" per day. This phenomenon is the result of reactive oxygen species that are generated during normal aerobic metabolism or from exposure to exogenous agents such as ionizing radiation (Hutchinson, 1985). These metabolic by-products include a short list of chemicals such as the superoxide radical, the hydroxyl radical and hydrogen peroxide, which have been demonstrated to induce DNA damage and may contribute to a variety of human disorders, tumor promotion and aging (Halliwell and Gutteridge, 1990; Fischer et al., 1988; Saul and Bonifaz, 1987). The most reactive species, the hydroxy radical, produces a broad spectrum of DNA damage (Teoule, 1987), the predominant forms being modified bases, apurinic/apyrimidinic (abasic or AP) sites and single-strand breaks with 3' termini blocked by nucleotide fragments (Hutchinson, 1985; Giloni et al., 1981; von Sonntag, 1991).

The major mutagenic base lesion generated by hydroxyl radicals is 8-hydroxyguanine. 8-hydroxyguanine base-pairs preferentially with adenine rather than cytosine and, thus, causes transversion mutations after replication. The oxidation of guanine is thought to be one of the major spontaneous events which results in a directly premutagenic lesion. Other well studied DNA adducts generated by free radical attack are the ring-saturated derivatives of a pyrimidine (i.e., thymine and cytosine glycols and pyrimidine hydrates; Halliwell and Aruoma, 1991). These derivatives are non-coding bases and are, therefore, primarily cytotoxic lesions. However, under certain circumstances they can be mutagenic. Recently, DNA damage by oxygen free radicals was definitively shown to cause mutations by modifying nucleotide bases, which results in miscoding when the DNA is copied by DNA polymerase, and by altering the conformation of the DNA template (Feig and Loeb, 1993).

B. Exogenous Insults

Some of the most common environmental insults which can alter the chemical structure of DNA are ultraviolet light from the sun, alkylating agents, ionizing radiation, and a variety of dietary chemicals (Brash, 1988; Saffhill et al., 1985; Hutchinson, 1985; Ames, 1983). These chemical and physical agents react directly with DNA to introduce modifications in base composition.

1. Ionizing Radiation

Ionizing radiation is capable of inducing hundreds of products in DNA (Hutchinson, 1985). These DNA damaging capabilities are a result of both direct and indirect effects of ionizing radiation. The so-called direct effects result from direct interaction of the radiation energy with DNA. The indirect effects are due to the interaction of reactive oxygen species, formed by the radiation, with DNA. In view of the similarities between some endogenous mutagens produced by normal aerobic metabolism and those (such as hydroxyl radicals) produced by radiation, one might expect spontaneous and radiation-induced point mutations to have some mechanisms in common. The hydroxy radical is the major product formed by the action of ionizing radiation on water. Thus, many of the DNA damages identified as products of ionizing radiation are similar to those adducts which result from attack of DNA by reactive oxygen species.

2. Alkylating Agents

Alkylating agents are potent environmental mutagens which are capable of forming a considerable number of different adducts by reacting with cellular DNA (for review see Lindahl et al., 1988). These agents can alkylate all four bases of DNA at the nitrogens or oxygens as well as the sugar phosphates of the DNA backbone. However, the distribution of the adducts at the various sites depends on both the chemical structure of the alkylating agent and the alkyl group itself. Although none of these DNA lesions can be entirely ruled out as a potential source of mutations, there is extensive literature suggesting that adducts at the $O^6$-position of guanine and the $O^4$-position of thymine may be of particular importance in this respect. $O^6$-methylguanine preferentially pairs with thymine rather than cytosine resulting in a GC to AT transition (Loveless, 1969). $O^4$-methylthymine, also a miscoding base, induces AT to GC transitions. Another important product of attack on DNA by alkylating agents is N3-methyladenine, which causes cell-killing (Karran et a/., 1982). N3-methyladenine blocks the progress of DNA polymerases during replication (Larson et al., 1985). However, the principle target of alkylating agents is the N7 position of guanine (Saffhill et al., 1985). Although N7-alkylguanine itself is not a deleterious lesion, it can undergo a rearrangement to yield a ring-opened imidazole form (formamidopyrimidine). Formamidopyrimidine residues have been shown to inhibit DNA polymerase synthesis (Boiteux and Laval, 1983) and several observations suggest that this adduct may play a significant role in processes leading to mutagenesis and/or cell death by alkylating agents. In addition, N-alkylpurines, such as those just mentioned, are indirectly mutagenic because their removal, either in a spontaneous chemical reaction or by the action of DNA glycosylases results in the formation of AP sites. While AP sites normally prevent DNA replication, under special circumstances they can also lead to mutations (Loeb and Preston, 1986). N-alkylpurines may also contribute, simply by accumulating, to other biological effects such as induction of chromosomal aberrations as well as the aging process (Gensler and Berstein, 1981). Finally, some alkylating agents are bifunctional; that is, they have two reactive groups. Each molecule is, therefore, capable of reacting with two sites in DNA, which potentially can result in the formation of an inter- or intra-strand crosslink, which appear to block both DNA replication and transcription (Friedberg, 1985).

3. Dietary Chemicals

The normal diet of an organism contains many potentially mutagenic and carcinogenic agents such as alcohol, nitrosamines, and phorbol esters and, more recently, a number of hormones have been found in diets, such as estrogens. Ames (1983) describes 16 examples of DNA-damaging chemicals found in plants that are part of the human diet. Many of these mutagens and carcinogens exert their effect through the generation of oxygen radicals. In addition, these chemicals are capable of reacting with DNA to generate single-strand breaks, double-strand breaks, and bulky DNA adducts.

4. Ultraviolet Radiation

One of the most common deleterious environmental agents that organisms are exposed to is ultraviolet (UV) light (Friedberg, 1985). Although proteins and cellular membranes are targets of UV irradiation, the major target is DNA, which absorbs short wavelength UV most efficiently (254 nm/UVC). In particular, UV irradiation induces the formation of numerous DNA photoproducts, the most prominent ones being the cyclobutane pyrimidine dimer (CPD) and pyrimidine (6–4) pyrimidine photoproduct (PPP) (Setlow, 1968). Induction frequencies of these two lesions vary between organisms and is sequence dependent. It has been reported that the preferred dipyrimidine order for CPD or PPP formation is TT>TC>CC (Haseltine, 1983).

Both CPDs and PPPs are thought to be non-instructional bulky lesions (Setlow, 1968). However, little is known as to how these UV-induced photoproducts contribute to transformation of a UV-exposed cell into a malignant cancerous cell. Though TT is by far the most frequent putative site for a UV-induced lesion, base-pair changes at these sites were observed to be infrequent. Instead mutations are primarily seen at the C of TC, CT, or CC cyclobutane dimers, and to a lesser extent, at the C of TC and CC (6–4) photoproducts (Brash, 1988). This finding supports the hypothesis that DNA polymerases preferentially insert an A opposite a modified, non-coding nucleotide (The A-rule).

5. Antitumor antibiotics

Finally, antitumor antibiotics such as bleomycin and neocarzinostatin produce both strand breaks and AP sites in DNA (Povirk and Houlgrave, 1988). Repair of bleomycin-treated DNA is accomplished through the action of an AP endonuclease enzyme. On the other hand, neocarzinostatin-treated DNA is resistant to the action of AP endonucleases, perhaps due to the closely opposed strand breaks which may be refractive to the action of repair enzymes (Povirk and Houlgrave, 1988).

C. Consequences of DNA Damage

Adducts in DNA have been shown to block transcription and replication, which can lead to cell death. Alternatively, the erroneous repair (i.e., SOS response, which is a bacterial error-prone repair mechanism) or replication of DNA that contains a lesion can give rise to mutations. In addition, several of the DNA adducts described are highly mutagenic miscoding bases which preferentially pair with the incorrect nucleotide causing transitions or transversions. Such a permanent alteration in the DNA sequence may alter the expression of genes, including those involved in controlling cell proliferation and differentiation. In this way, routes in the multi-step process of cancer can be initiated by DNA damage.

Clearly, the role of DNA repair in the prevention of carcinogenesis is demonstrated by the several well-known human diseases associated with DNA repair defects, which are associated with an increased risk for developing cancers (Bohr et al., 1989). Besides a predisposition to cancer, individuals afflicted with a DNA-repair disorder display a bewildering array of clinical symptoms, including immunodeficiencies, neurological problems, skeletal abnormalities and altered growth.

D. DNA Repair Mechanisms

Cells have evolved the capacity to remove or tolerate lesions in their DNA (Friedberg, 1985). The most direct mechanisms for repairing DNA are those that simply reverse damage and restore DNA to its normal structure in a single step. A more complex mechanism, excision repair, involves incision of the DNA at the lesion site, removal of the damaged or inappropriate base(s), and resynthesis of DNA using the undamaged complementary strand as a template. This system of repair can further be categorized into base and nucleotide excision repair.

Base excision repair involves two major classes of repair enzymes, namely, N-glycosylases and AP endonucleases (Wallace, 1988; Sakumi and Sekiguchi, 1990; Doetsch and Cunningham; 1990). DNA N-glycosylases are enzymes that hydrolyze the N-glycosidic bond between the damaged base and the deoxyribose moiety, leaving behind an AP site on the DNA backbone. AP sites produced by the action of N-glycosylases are acted upon by AP endonucleases, which can make an incision either 3' to the AP site (class I AP lyase) or 5' to the AP site (class II AP endonuclease). All those enzymes shown to contain class I AP lyase activity possess an associated DNA glycosylase activity; however, not all glycosylases are AP lyases. Class II AP endonucleases are the major enzymes responsible for the repair of AP sites in DNA.

DNA glycosylases can be defined as enzymes which recognize specific DNA base modifications and catalyze the hydrolysis of the N-glycosylic bond that links a base to the deoxyribose-phosphate backbone of DNA (for review, see Sancar and Sancar, 1988; Wallace, 1988; Sakumi and Sekiguchi, 1990). This enzymatic activity results in the generation of an AP site. To date, several DNA glycosylases have been identified and are classified into two major families: 1) enzymes that possess only DNA glycosylase activity and 2) enzymes that contain both a DNA glycosylase activity and an associated class I AP lyase activity; that is, enzymes that catalyze a beta-elimination cleavage of the phosphodiester bond 3' to an AP site.

1. Glycosylases

Enzymes which carry out only N-glycosylase activity are uracil-DNA glycosylase (Wist et al., 1978; Krokan and Wittwer, 1981; Anderson and Friedberg, 1980; Wittwer and Krokan, 1985; Domena and Mosbaugh, 1985; Domena et al., 1988; Olsen et al., 1989; Wittwer et al., 1989; Vollberg et al., 1989; Muller and Caradonna, 1991; Weng and Sirover, 1993; Yamamoto and Fujiwara, 1986; Vollberg et al., 1987; Seal et al., 1991), 3-methyladenine-DNA glycosylase, hypoxanthine-DNA glycosylase, and hydroxymethyluracil-DNA glycosylase (Thomas et al., 1982; Everson and Seeberg, 1982; Karran et al., 1982; Bjelland et al., 1993; Nakabeppu et al., 1984a; Clarke et al., 1984; Washington et al., 1988, 1989; Harosh and Sperling, 1988; Dianov and Lindahl, 1994; Myrnes et al., 1982; Karran and Lindahl, 1980). Each of these proteins received its name based on the type of DNA adduct it recognizes and releases. Enzymes that contain both N-glycosylase activity and AP lyase activity are T4 endonuclease V, endonuclease III, and formamidopyrimidine-DNA glycosylase.

2. AP Endonucleases

While many DNA damaging agents may not directly produce AP sites in DNA, the manner in which they physically or chemically modify DNA may be the target for a class of DNA repair enzymes known as DNA glycosylases, whose action ultimately leads to the formation of AP sites in DNA.

For example, the spontaneous, or chemically induced deamination of cytosine residues in DNA leads to the formation of uracil (Lindahl and Nyberg, 1972; Schuster, 1960; Hayatsu, 1976). This potentially mutagenic event (Duncan and Weiss, 1982) is recognized by a uracil-DNA glycosylase, which enzymatically hydrolyzes the sugar-base glycosylic bond, forming an apyrimidinic site (Lindahl, 1974). From studies conducted in E. coli, numerous other DNA glycosylases exist, all of which form a baseless site in DNA as a part of the repair process (see Friedberg, 1985 and references therein).

Structures closely resembling an AP site in DNA are also biologically important. For example, ionizing radiation produces a one nucleotide gap in DNA with modified 3' termini at strand breaks. These termini can be either 3'-phosphates, or 3'-phosphoglycolates (Henner et al., 1983). Since a substantial portion of ionizing-induced DNA damage is produced by hydroxyl free radicals, other model systems have been explored. It was found that E. coli treated with hydrogen peroxide contain 3'-phosphoglycolate residues in their DNA. Importantly, these lesions are identified by an AP endonuclease (Demple, et al., 1986). Urea residues are also produced by oxidative stress, which appears to be target for two different DNA repair activities, one of which is an AP endonuclease enzyme (Kow and Wallace, 1985). Oxidative stress also leads to purines undergoing opening of the imidazole ring to create formadopyrimidine residues.

This lesion is repaired by the mut M locus of E. coli that encodes a N-glycosylase (FPG) that nicks DNA 3' and 5' to the site. It is now generally acknowledged that the primary substrate of FPG is, in fact, 8-hydroxyguanine, which is most likely both mutagenic and carcinogenic if not repaired. Taken together, agents which produce hydroxyl radicals, hydrogen peroxide, as well as superoxide, may all produce AP sites in DNA, or sites that closely resemble an AP site.

The major cellular enzymes initiating the repair process for AP sites, the so-called "class II" AP endonucleases, have been identified and characterized in bacteria, yeast and mammalian systems, including humans cells (for review see Doetsch and Cunningham, 1990). These repair proteins hydrolyze the phosphodiester backbone immediately 5' to an AP site generating a normal 3'-hydroxyl nucleotide which can prime DNA repair synthesis. Moreover, these enzymes have also been shown to contain repair activity for 3'-terminal oxidative lesions (Henner et al., 1983; Demple et al., 1986; Johnson and Demple, 1988a and 1988b; Ramotar et al., 1991b). By hydrolyzing 3'-blocking fragments from oxidized DNA, these enzymes can produce normal 3'-hydroxyl nucleotide termini, permitting DNA repair synthesis. To date, only the AP endonuclease enzymes of microbial systems have been well characterized both biochemically and molecularly. However, large steps have been made recently in cloning eukaryotic AP endonucleases and identifying their cellular function(s).

In E. coli, the major AP endonuclease enzymes are exonuclease III and endonuclease IV. Exonuclease III comprises approximately 90% of the cellular AP endonuclease activity (Rogers and Weiss, 1980) and greater than 95% of the total activity for removal of blocked 3' ends (Demple et al., 1986): while endonuclease IV accounts for much of the residual activity (Ljungquist et al., 1976).

Exonuclease III, encoded by the xth gene (Saporito et al., 1988), was also identified as endonuclease II and endonuclease VI because of its multiple enzymatic activities (Friedberg and Goldthwait, 1969; Kirtikar et al., 1975a, 1975b; 1975c; Gossard and Verly, 1978). In fact, this protein was originally purified as a byproduct of DNA polymerase I (Richardson and Kornberg, 1964). As mentioned, exonuclease III is the major class II AP endonuclease in E. coli and incises on the 5' side of an AP site, leaving a 3' hydroxyl and a 5' phosphate (Kow, 1989). This 3' hydroxyl group is a substrate for DNA polymerase I (Warner et al., 1980) and does not require further processing. In addition to its AP endonuclease activity, exonuclease III demonstrates phosphodiesterase, exonuclease, phosphatase and RNAse H activities (Weiss, 1981). Recently, exonuclease III was shown to have 5' endonuclease activity against urea residues (Kow and Wallace, 1985). Exonuclease III is a 28 kDa protein and has an absolute requirement for magnesium. E. coli xth mutants are slightly sensitive to killing by MMS, which produces AP sites, and near UV, and are extremely sensitive to hydrogen peroxide (Cunningham et al., 1986). Conversely, this mutant strain displays no sensitivity to gamma rays or bleomycin.

Endonuclease IV, encoded by the nfo gene, is the other main class II AP endonuclease of E. coli (Saporito and Cunningham, 1988). Like exonuclease III, endonuclease IV exhibits many activities such as phosphatase, phosphodiesterase, as well as endonuclease activity against DNA containing urea residues (Kow and Wallace, 1987). Atomic absorption analysis reveals that this protein contains several zinc atoms as well as manganese, which appear to be involved in the mechanism of action (Levin et al., 1988, 1991). Nfo mutants have increased sensitivity to the alkylating agents MMS and mitomycin C, as well as the oxidant tert-butyl hydroperoxide (Cunningham et al., 1986). Moreover, these mutants are hypersensitive to bleomycin exposure, but are not sensitive to gamma rays or hydrogen peroxide which implies that endonuclease III and endonuclease IV have different biological roles. Two other minor apurinic activities also have been detected in E. coli, these being endonuclease V (Gates and Linn, 1977; Demple and Linn, 1982b) and endonuclease VII (Bonura et al., 1982).

S. cerevisiae contains a single major AP endonuclease/3'-repair diesterase encoded by the APN1 gene (Popoff et al., 1990). Apn1 protein has many biochemical properties in common with endonuclease IV (Johnson and Demple, 1988a, 1988b) and comparison of the predicted amino acid sequences of these two enzymes indicated that they are remarkably homologous. Apn1 accounts for greater than 97% of yeast AP endonuclease and 3'-repair diesterase activities. Mutants in apn1 are hypersensitive to oxidative DNA damage and alkylating agents, reaffirming the importance of this protein in carrying out DNA repair (Ramotar et al., 1991b). Interestingly, when compared to wild-type strains, Apn1-deficient yeast strains were also found to display higher spontaneous mutation rates when grown in either aerobic or anaerobic conditions. This result suggests that there exist several endogenous mutagens, not just reactive oxygen species, capable of generating DNA damage that requires the repair functions of Apn1. In addition, the 41 kDa Apn1 protein can function in bacteria lacking exonuclease III and endonuclease IV in a manner similar to its proposed functions in yeast (Ramotar et al., 1991a). Earlier studies identified at least five chromatographically distinct apurinic activities in yeast, however, the cloning of these genes and the determination of their relationship to Apn1 awaits further investigation (Armel and Wallace, 1978, 1984; Chang et al., 1987).

Overall, E. coli lacking exonuclease III or yeast deficient for Apn1 demonstrate hypersensitivity to both oxidative and alkylating agents supporting the idea that these enzymes participate in two distinct pathways of DNA repair: removal of 3'-blocking fragments that result from oxidative DNA damage and restoration of alkylation-induced AP sites (Popoff et al., 1990; Ramotar et al., 1991b). These findings clearly indicate that these enzymes play a critical role in protecting cells against agents which cause alterations in DNA composition.

Two AP endonucleases have been partially purified from Drosophila embryos and are resolved by phosphocellulose chromatography (Spiering and Deutsch, 1981). The estimated molecular weights of these two proteins are 66 kDa and 63 kDa, much larger than those enzymes characterized from other organisms. Whether these proteins are encoded by different genes or the same gene and modified post-translationally awaits further investigation. Interestingly, antibody generated to the major HeLa AP endonuclease (Ape) cross-reacts with both these Drosophila proteins (Kane and Linn, 1981), suggesting they are at least antigenically similar. In addition, studies have shown that the 66 kDa protein resides in the nucleus, whereas the 63 kDa protein translocates to the mitochondria. Initial assays of AP activity using partially purified fractions of the 63 kDa and 66 kDa proteins indicate that these enzymes incise AP DNA via class I AP lyase and class III AP endonuclease mechanisms respectively. (Spiering and Deutsch, 1986). Class III AP endonucleases cleave on the 3'-side of an AP site generating a deoxyribose 3'-phosphate and 5'-OH termini. This finding is the first report of a class III type enzyme and needs to be confirmed by additional studies.

Another Drosophila enzyme able to initiate the repair of abasic sites in DNA has been cloned and is termed Rrp1 (Recombination Repair Protein 1, Sander et al., 1991b). This enzyme was originally purified based on its strand transferase activity, indicating a possible involvement in recombination (Lowenhaupt et al., 1989). The carboxy terminus of this protein displays significant homology to exonuclease III (Sander et al., 1991b). Rrp1 has $Mg^{2+}$ dependent AP endonuclease, 3' exonuclease, and strand transfer activities, in addition to a single stranded DNA renaturation activity (Sander et al., 1991a, 1991b). Recent results indicate that the carboxy terminus, and therefore, presumably the activity involving exonucleolytic processing of double-stranded DNA, is necessary for the initiation of the strand transfer reaction (Sander et al., 1993). Recent reports of a multifunctional ribosomal/class II AP endonuclease (SP3) is discussed below.

The inventors previously have shown that Drosophila ribosomal protein S3 (dS3) is a multifunctional protein having DNA repair capabilities acting on apurinic/apyrimidinic (AP) sites in DNA and also acting as a combined DNA glycosylase/AP lyase recognizing 8-oxoguanine lesions in DNA (Yacoub et al., 1996). Using mutants in E. coli, the inventors have been able to demonstrate dS3's ability to correct a strain deficient in 8oxoG repair, namely MutM. This strain is defective in the fpg protein which repairs 8oxoG and formamidopyrimidine (fapy) lesions in the E. coli DNA. The Drosophila S3 gene completely corrects this deficiency following $H_2O_2$ (a potent oxidative DNA damaging agent) exposure. In order to demonstrate that the oxidative DNA damaging effect of MMC is through the formation of 8oxoG or FaPy residues the inventors transformed the fpg deficient strain of E. coli (MutM) with either the dS3 or E. coli fpg (MutM) gene. Survival studies were performed and the inventors have demonstrated that both the E. coli fpg and the dS3 genes can completely rescue the MutM from the toxicity of MMC. As it has not been shown that either FPG or dS3 can repair or act on cross-linked DNA, and since the only defect of DNA repair in this strain is the fpg gene, the inventors conclude that a significant component of MMC's ability to kill cells is due to oxidative DNA damage that can be repaired by either the fpg or dS3 genes. Using the dS3 cDNA, the inventors have also found that dS3 restores the FA-type A cells back to wild-type levels of resistance to MMC, and also hydrogen peroxide ($H_2O_2$). Furthermore, the inventors have recently shown that the dS3 gene can also rescue FA-C cells against both of these same agents, MMC and $H_2O_2$. These findings are exciting and support the inventors assertions that the use of oxidative DNA repair genes, and most likely oxidative detoxifying agents and genes (peroxidase, catalase, glutathione transferase, etc.), will be useful in the protection of FA cells and patients against deleterious effects of chemotherapeutic agents that have an oxidative DNA damaging component.

AP endonucleases have been purified to apparent homogeneity from a variety of mammalian sources including mouse, calf thymus, human placenta, and HeLa cells (Seki et al., 1991a; Haukanes et al., 1989; Ivanov et al., 1988; Henner et al., 1987; Cesar and Verly, 1983; Shaper et al., 1982; Kane and Linn, 1981). The activities have similar molecular weights around 37 kDa and require magnesium. Each of these enzymes appears to be a class II AP endonuclease.

Using a synthetic DNA substrate that contains 3'-PGA esters ($3'—O—PO_3—CH_2—CHO$) as the predominant damages, two major diesterases were identified in HeLa cells (Chen et al., 1991). Interestingly, these activities were found to correspond with the AP endonuclease activities already reported. In fact, one of the enzymes was found to be identical to a previously studied HeLa AP endonuclease (Kane and Linn, 1981) and was cloned (APE, Demple et al., 1991; HAP1, Robson and Hickson, 1991; HAP1, Cheng et al., 1992b). Ape shows significant homology to the AP endonucleases of E. coli (exonuclease III), Drosophila (Rrp1), mouse, and bovine (Seki et al., 1991b; Robson et al., 1991). The APE cDNA maps to position 11.2–0.4 of chromosome 14 in the human genome, a locus not previously identified with any known human disease thought to involve DNA repair (Harrison et al., 1992; Robson et al., 1992). However, in contrast to exonuclease III and endonuclease IV of E. coli and Apn1 of S. cerevisiae, which display approximately equal 3'-repair activity and AP-cleaving activity (Levin et al., 1988; Johnson et al., 1988a, 1988b), the HeLa enzyme, Ape, shows low 3'-repair activity (approximately 1% of the AP-cleaving activity). Furthermore, the APE protein only partially complements repair-deficient E. coli, conferring significant cellular resistance to MMS, an alkylating agent, but little resistance to hydrogen peroxide, an oxidative agent (Demple et al., 1991). This information, in agreement with the biochemical evidence, suggests that the Ape protein may function well in vivo in repairing alkylation-induced AP sites but poorly in removing oxidative 3'-terminal deoxyribose fragments. Instead HeLa cells possess a second distinct enzyme which displays 3'-repair and AP-cleaving activity at more similar levels (Chen et al., 1991). This second human enzyme most likely is responsible, in vivo, for the removal of 3'-blocking fragments generated by reactive oxygen species. Molecular genetic analysis of this second AP endonuclease/3'-repair diesterase from HeLa cells, and thus cloning the gene, would assist in efforts to delineate the biological role(s) of this human DNA repair protein.

Regulation of DNA repair enzymes is an important part in how cells cope with environmental stress and maintain genetic integrity. *E. coli* yeast and HeLa cells express high constitutive levels of exonuclease III, Apn1 and Ape, respectively (Demple et al., 1991). This finding appears to indicate that the repair functions of these enzymes are constantly required in the face of continual cellular production of endogenous mutagens. In addition, expression of these enzymes in high levels would permit rapid repair of substantial amounts of DNA damage resulting from abrupt assaults by DNA-damaging agents, without requiring the synthesis of new proteins. This would explain why the levels of exonuclease III and Apn1 appear unaffected following exposure to various oxidizing agents (Demple and Halbrook, 1983; Chan and Weiss, 1987; Johnson and Demple, 1988a). *E. coli* endonuclease IV, however, which is normally expressed at relatively low levels, is inducible to levels comparable to exonuclease III upon exposure to superoxide generators, such as paraquat (Chan and Weiss, 1987). To date, human genes encoding DNA repair enzymes appear non-inducible and systems such as the adaptive response and SOS response of *E. coli* have not been found.

II. DNA Repair Fusion Proteins

A fusion protein is a specialized kind of insertional variant. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In a particular embodiment the fusion construct of the present invention links hMGMT to hAPE.

The term "fusion protein" as used herein refers to a C-terminal to N-terminal fusion of a first protein and a second protein. The fusion proteins of the present invention include constructs in which the C-terminal portion of the first protein is fused to the N-terminal portion of the second, and also constructs in which the C-terminal portion of the second protein is fused to the N-terminal portion of the first. Preferred fusion proteins of the present invention have sequences represented by the formula:

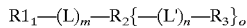

wherein $R_1$, $R_2$ and $R_3$ are DNA repair proteins; L and L' are linker peptide sequences; and m, n and o each, independently, =0 or 1. The fused proteins are linked in such a manner as to produce a single protein which retains the biological activity of each protein. Herein, specific fusion protein constructs are named by listing the domains in the fusion protein in their order of occurrence (with the N terminal domain specified first, followed by the C-terminal domain). Thus, for example, MGMT/APE refers to a fusion protein comprising MGMT followed by APE (i.e., the C-terminus of MGMT is linked to the N-terminus of APE). In addition, amino acid deletions are indicated by the symbol "Δ", followed by the amino acids which are deleted. For example, "Δ1-60hAPE" refers to a hAPE sequence having the first 60 amino acids deleted.

Exemplary DNA repair proteins for use in the present invention include those from the base excision repair (BER) pathway, e.g., AP endonucleases such as human APE (hAPE, Genbank Accession No. M80261) and related bacterial or yeast proteins such as APN-1 (e.g., Genbank Accession No. U33625 and M33667), exonuclease III (ExoIII, xth gene, Genbank Accession No. M22592,) bacterial endonuclease III (EndoIII, nth gene, Genbank Accession No. J02857), huEndoIII (Genbank Accession No. U79718), and endonuclease IV (EndoIV nfo gene Genbank Accession No. M22591). Additional BER proteins suitable for use in the invention include, for example, DNA glycosylases such as, formamidopyrimidine-DNA glycosylase (FPG, Genbank Accession No. X06036), human 3-alkyladenine DNA glycosylase (HAAG, also known as human methylpurine-DNA glycosylase (hMPG, Genbank Accession No. M74905), NTG-1 (Genbank Accession No. P31378 or 171860), SCR-1 (YAL015C), SCR-2 (Genbank Accession No. YOL043C), DNA ligase I (Genbank Accession No. M36067), β-polymerase (Genbank Accession No. M13140 (human)) and 8-oxoguanine DNA glycosylase (OGG1 Genbank Accession No. U44855 (yeast); Y13479 (mouse); Y11731 (human)). Proteins for use in the invention from the direct reversal pathway include human MGMT (Genbank Accession No. M29971) and other similar proteins.

In a preferred embodiment of the present invention, an MGMT-APE fusion protein has been constructed and demonstrated to be functional in mammalian cells. This molecule is capable of protecting the bone marrow and other cells against DNA lesions created by a variety of alkylating agents or other agents which produce AP sites.

In addition to the entire MGMT-APE molecule as shown in SEQ ID NO:2, the present invention also relates to fragments of the polypeptide that may or may not include the C- or N-terminus of the molecule. For example, C-terminal truncations may be generated by genetic engineering of translation stop sites within the coding region (discussed below).

A variety of N-terminal, C-terminal and internal fragments may be created from the wild-type MGMT and APE proteins. Such fragments may be generated by genetic engineering of translation stop sites within the coding region (discussed below). Alternatively, treatment of the wild-type protein with proteolytic enzymes, known as proteases also may result in a wide variety of fragments. Examples of fragments may include contiguous residues of the MGMT protein (SEQ ID NO:10), of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, or more amino acids in length, and contiguous residues of the APE protein (SEQ ID NO:12) of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration). The MGMT fragment may be joined to the APE fragment directly, or alternatively the fragments may be joined through a linker.

A. Structural Features of the Polypeptide

The gene for human APE (SEQ ID NO:11) encodes a 318 amino acid polypeptide (SEQ ID NO:12). The gene for human MGMT (SEQ ID NO:9) encodes a 207 amino acid polypeptide (SEQ ID NO:10).

The present inventors have identified the region of human APE that is responsible for the redox regulation of different transcription factors. The inventors have shown that deletion of the N-terminal 150 amino acids results in the total loss of AP endonuclease activity (see FIG. 1B). However, a construct having a deletion of the N-terminal 60 amino acids retained AP endonuclease activity, as revealed by both in vitro and in vivo tests.

B. Functional Aspects

When the present application refers to the function of the MGMT/APE fusion protein, it is meant that the molecule in question has the to repair DNA using mechanisms of the base excision repair pathway and the mechanisms of the direct DNA reversal pathway as exemplified by hMGMT. Furthermore, it the fusion proteins may have the ability to protect the bone marrow and other non-target cells against DNA lesions created by a variety of alkylating agents or other insults that produce AP sites as a harmful side-effect of chemotherapy.

In alternative embodiments, the fusion proteins of the present invention may be used in the treatment of DNA-repair-defective human diseases e.g., Xeroderma Pigmentosum; (Cleaver, 1990; Bootsma and Hoeijmakers, 1991), Ataxia Telangiectasia, Cockayne's syndrome (Troelstra et al., 1992), Bloom's syndrome (Willis and Lindahl, 1987; Strathdee et al., 1992; Petrini et al., 1991; Barnes et al., 1992), Fanconi's anemia (FA; Strathdee et al., 1992), Parkinson's Disease and other neurodegenerative diseases including amyotrophic lateral sclerosis (Owen et al., 1996; Simonian and Coyle, 1996), Alzheimer's disease (Markesbery, 1997) and other age related disorders (Davies, 1995). Determination of which molecules possess this activity may be achieved using assays familiar to those of skill in the art. For example, transfer of genes encoding the fusion protein, or variants thereof, into cells that are undergoing oxidative DNA damage or to cells that are susceptible to DNA damage from chemotherapeutic agents will serve to protect such cells and prolong their life when compared to cells which have not received such fusion constructs. In certain examples cell viability of fusion construct treated cells in the presence of DNA damaging agents may be determined using trypan blue staining and comparing with that of untreated cells in the presence of the same agents.

C. Polypeptide Variants

The present invention also includes the use of proteins having amino acid sequences similar to those of the native proteins mentioned herein, but into which modifications are naturally provided (e.g., allelic variations in the nucleotide sequence which may result in amino acid changes in the polypeptides) or deliberately engineered. Modifications of interest in the sequences may include the replacement, insertion or deletion of one or more amino acid residues in the coding sequence. For example, the modified protein may contain one or more additional amino acids, at one or both ends of the polypeptide chain; may have an amino acid sequence which differs from that of the naturally-occurring protein; or may be an active fragment of the naturally-occurring protein. The term "substantially identical," is used herein to encompass such potential modification, and specifically herein means that a particular subject sequence, for example, a mutant sequence, varies from the native sequence (e.g., those shown in FIG. 1 and FIG. 2) by one or more substitutions, deletions, or additions, the net effect of which is to retain biological activity of the protein when derived as a APE/MGMT or MGMT/APE fusion protein.

As illustrative modifications, one polar amino acid, such as glycine, may be substituted for another polar amino acid; or one acidic amino acid, such as aspartic acid, may be substituted for another acidic amino acid such as glutamic acid; or a basic amino acid, such as lysine, arginine or histidine may be substituted for another basic amino acid; or a non-polar amino acid, such as alanine, leucine or isoleucine may be substituted for another non-polar amino acid.

Percent similarity may be determined, for example, by comparing sequence information using the GAP computer program, version 6.0, available from the University of Wisconsin Genetics Computer Group (UWGCG). The GAP program utilizes the alignment method of Needleman and Wunsch (1970), as revised by Smith and Waterman (1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), as described by Schwartz and Dayhoff (1979); (2) a penalty of 3.0 for each gap and an additional 0.10 penalty for each symbol in each gap; and (3) no penalty for end gaps.

As illustrative examples, specific mutations which may be undertaken in accordance with the invention include the deletion of some or all of amino acid 1 to about amino acid 60 of the hAPE protein. Such deletions leave a protein possessing AP endonuclease function. Additionally, point mutations may be introduced while leaving the protein with AP endonuclease functionality. Illustrative modifications to hMGMT include, for example, those reported in Crone et al. (1994). Of particular interest among those reported are a substitution of glycine at position 156 with alanine or tryptophan, alone or combined with a substitution of alanine for the proline at position 140 of the native protein. Such substitutions increased the reactivity of the proteins.

Figure 22:
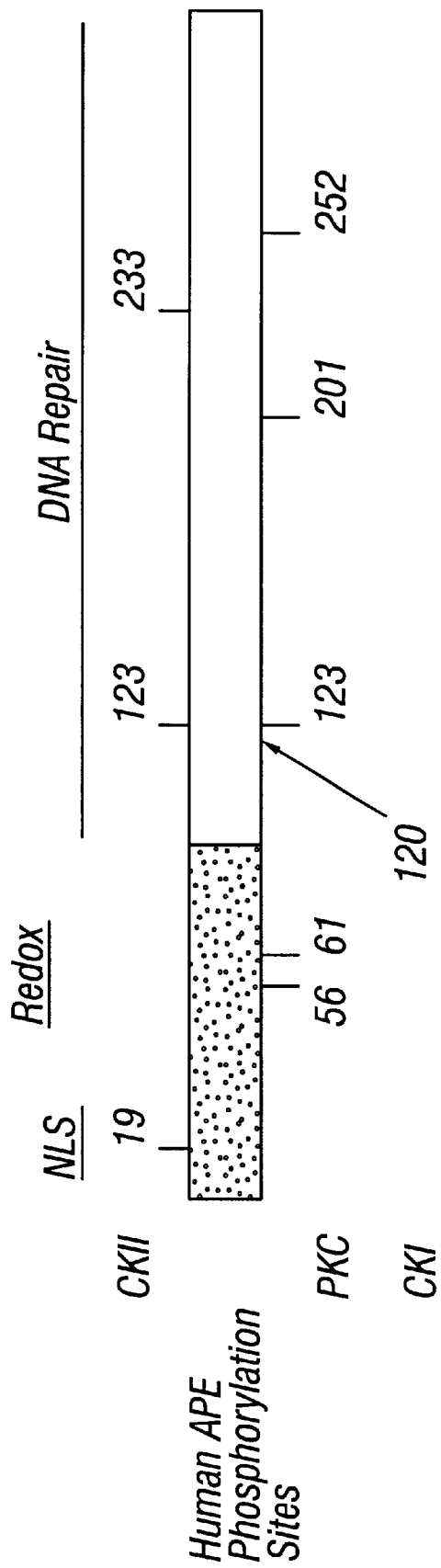
FIG. 22. Human APE phosphorylation sites.

The inventors have found that phosphorylation with Casein Kinase II (CKII) inactivates APE DNA repair activity The phosphorylation sites of hAPE are shown in FIG. 22. Deleting the first 60 amino acids results in an active APE protein for repair, thus ruling out the involvement amino acid 19 in APE DNA repair activity. However, upon CKII phosphorylation, activity lost. Phosphorylation with protein kinase C (PKC) or Casein Kinase I (CKI) does not inactivate the protein for DNA repair. Therefore, the inventors believe that amino acid at 123 is not involved in this inactivation of DNA repair following phosphorylation because PKC phosphorylates at amino acid 123, as does CKII. However, the inventors studies provide evidence that amino acid 233 is the site of phosphorylation that inactivates APE. The inventors confirmed these results using site directed mutagenesis at these sites.

It is contemplated that amino acid sequence variants of the fusion polypeptide can be substitutional, insertional or deletion variants. Deletion variants lack one or more residues of the "native protein" which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of the fusion construct, but with altered and even improved characteristics.

D. Purification of Proteins

It will be desirable to purify the MGMT-APE fusion construct or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of min, or at most an h. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Antigen Compositions

The present invention also provides for the use of the fusion construct proteins or peptides as antigens for the immunization of animals relating to the production of antibodies. It is envisioned that either the fusion protein, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. Nucleic Acids

As disclosed above, the present invention provides in one aspect a DNA sequence encoding a fusion protein comprising at least two DNA repair proteins, and in a preferred form at least one protein from each of the DNA base excision repair pathway (e.g., MPG and AP endonucleases, OGG1, FPG, endoIII, endoIV, exoIII, APN1, NTG-1, NTG-2, SCR-1 and SCR-2) and the direct reversal pathway (e.g., MGMT). It has been discovered that multiple DNA repair proteins can be incorporated into a fusion protein which exhibits repair capacity exceeding that of either protein alone and thereby enhances significantly the resistance of non-target cells to chemotherapeutic agents.

In this regard, as used herein, "DNA sequence" refers to a DNA polymer, in the form of a separate fragment or as a component of a larger DNA construct. Such sequences are preferably provided in the form of an open reading frame uninterrupted by internal nontranslated sequences, or introns, which are typically present in eukaryotic genes. Genomic DNA containing the relevant sequences could also be used. Sequences of non-translated DNA may be present 5' or 3' from the open reading frame, where the same do not interfere with manipulation or expression of the coding regions.

Genes for hMGMT and hAPE have been identified and are known to those of skill in the art. In addition, it should be clear that the present invention is not limited to the specific nucleic acids disclosed herein. As discussed below, an "MGMT gene" or an "APE gene" may contain a variety of different bases and yet still produce corresponding polypeptides that are functionally and in some cases structurally, indistinguishable, from the human genes discussed herein.

Similarly, any reference to a nucleic acid should be read as encompassing a host cell containing that nucleic acid and, in some cases, capable of expressing the product of that nucleic acid. In addition to therapeutic considerations, cells expressing the fusion construct of the present invention may prove useful in the context of screening for agents that induce, repress, inhibit, augment, interfere with, block, abrogate, stimulate or enhance the function of the MGMT-APE fusion polypeptide.

A. Nucleic Acids Encoding MGMT-APE

The human genes for MGMT and APE are disclosed in SEQ ID NO:9 and SEQ ID NO:11, respectively. Nucleic acids according to the present invention may encode an entire MGMT gene linked to an entire APE gene, a domain of MGMT gene linked to the entire APE gene, an entire MGMT gene linked to a domain of the APE gene, or any other fragment of the APE and MGMT sequences set forth herein. In a preferred embodiment, the MGMT-APE DNA sequence has a sequence as set forth in SEQ ID NO:1, in another embodiment, the MGMT-APE DNA sequence has a sequence as set forth in SEQ ID NO:3. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given APE or MGMT from a given species may be represented by natural variants that have slightly different nucleic acid sequences but, nonetheless, encode the same protein (see Table 1 below).

As used in this application, the term "a nucleic acid encoding an MGMT-APE fusion construct" refers to a nucleic acid molecule that has been isolated free of total cellular nucleic acid. In a preferred embodiment, the invention concerns a nucleic acid sequence essentially as set forth in SEQ ID NO:1, in yet another embodiment, the sequences is as set forth in SEQ ID NO:3. The term "as set forth in SEQ ID NO:1" means that the nucleic acid sequence substantially corresponds to a portion of SEQ ID NO: 1. However, the sequences set forth in SEQ ID NO:1 and SEQ ID NO:3 are only exemplary MGMT-APE fusions, indeed the present invention may fuse any contiguous length of MGMT (SEQ ID NO:9) to any contiguous length of APE (SEQ ID NO:11) so long as expression product of the fusion construct retains DNA repair activity. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1 will be sequences that are "as set forth in SEQ ID NO:1." Sequences that are essentially the same as those set forth in SEQ ID NO:1 may also be functionally defined as sequences that are capable of hybridizing to a nucleic acid segment containing the complement of SEQ ID NO:1 under standard conditions.

The DNA segments of the present invention include those encoding biologically functional equivalent APE and MGMT proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

DNA analog sequences are "substantially identical" to the specific DNA sequences disclosed herein if: (a) the DNA analog sequence is derived from substantially the entire coding regions of the native mammalian APE and MGMT genes; or (b) the DNA analog sequence is comparable in length with and capable of hybridization to DNA sequences of (a) under moderately stringent conditions and which encode biologically active APE or MGMT molecules; or (c) DNA sequences which are degenerate as a result of the genetic code to the DNA analog sequences defined in (a) or (b) and which encode biologically active APE or MGMT molecules. Substantially identical analog proteins will be greater than about 80 percent similar to the corresponding sequence of the native protein. Sequences having lesser degrees of similarity but comparable biological activity are considered to be equivalents. In defining nucleic acid sequences, all subject nucleic acid sequences capable of encoding substantially similar amino acid sequences are considered substantially similar to a reference nucleic acid sequence.

C. Antisense Constructs

In some cases, the endogenous APE may not be non-functional. Rather, they may have aberrant functions that cannot be overcome by replacement gene therapy, even where the "wild-type" molecule is expressed in amounts in excess of the mutant polypeptide. Antisense treatments are one way of addressing this situation. Antisense technology also may be used to "knock-out" function of APE in the development of cell lines or transgenic mice for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Vectors for Cloning, Gene Transfer and Expression

In order to achieve expression of the fusion constructs of the present invention, DNA encoding the construct can be conventionally incorporated into viral, plasmid or other vectors and used to transform various mammalian, bacterial or other cell types to achieve expression of the fusion protein in the cells. Illustrative mammalian cells include HeLa, endothelial, fibroblast, germ (e.g., 833K), lung, liver, neural, testis, skin or other cells which may benefit from the engineered protection provided by the present invention.

In one aspect, the invention provides methods for protecting cells, especially hematopoietic cells, against chemotherapy damage, which involve expressing in the cells (preferably overexpressing) a fusion protein of the invention. Thus, in a preferred method of the invention, hematopoietic cells, preferably obtained from the patient to be treated, will be transformed in an ex vivo protocol with a recombinant vector of the invention. The bone marrow of the patient will then be engrafted with the transformed cells, for example by intravascular administration of the cells. In this manner, the cells will demonstrate increased resistance, and enhanced survival, in the presence of the agent employed in the chemotherapy, providing lower levels of cell damage and/or allowing for increased dosing of the chemotherapeutic agent(s).

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| ENHANCER/PROMOTER |
| --- |
| Immunoglobulin Heavy Chain |
| Immunoglobulin Light Chain |
| T-Cell Receptor |
| HLA DQ α and DQ β |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |

TABLE 2-continued

| ENHANCER/PROMOTER |
| --- |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins encoded by independent genes, intracellular or membrane-bound proteins and selectable markers. In this way, expression of several proteins can be simultaneously engineered into a cell with a single construct and a single selectable marker.

(iv) Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papoviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

A particularly preferred viral delivery system is the retroviral system. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Another of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 d after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

(v) Use of genes to transform host cells

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired.

Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, antimetabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further, below.

IV. Methods of Effecting DNA Repair

The involvement of DNA repair systems in preventing carcinogenesis clearly is demonstrated by the high incidence of cancer found associated with several well-recognized DNA-repair-defective human diseases (i.e., Xeroderma Pigmentosum (XP; Cleaver, 1990; Bootsma and Hoeijmakers, 1991), Ataxia Telangiectasia (AT), Cockayne's syndrome (CS; Troelstra et al., 1992), Bloom's syndrome (BS; Willis and Lindahl, 1987; Strathdee et al., 1992; Petrini et al., 1991; Barnes et al., 1992), and Fanconi's anemia (FA; Strathdee et al., 1992). In addition to these diseases, there exist several other syndromes that are DNA damage sensitive and are suspect for a DNA repair deficiency (for review see Hoeijmakers and Bootsma, 1992; Bohr et al., 1989).

Clinical features of XP include extreme hypersensitivity to ultraviolet (UV) irradiation associated with neurological abnormalities and mental impairment. It appears that the repair deficiency of XP is at an early step in the excision repair pathway such as damage recognition or incision (Cleaver, 1990; Bootsma and Hoeijmakers, 1991). There are seven complementation groups of XP and a variant group, indicating at least eight genes in the repair process-some of which have been identified.

CS is characterized by dwarfism, neurological abnormalities, mental retardation, and hypersensitivity to UV-induced DNA damage. This human disease appears to be a deficiency in the preferential DNA repair of actively transcribed genes. Recently, a gene involved in preferential repair of transcribed sequences in eukaryotes, ERCC-6, was isolated and characterized (Troelstra et al., 1992)

Patients suffering from BS display a photosensitivity and are at higher risk for developing hemopoietic cancer and/or immunodeficiency. In addition, BS patients demonstrate a 15-fold increase in the rate of spontaneous sister chromatid exchanges. Evidence has been obtained for altered biochemical properties of partially purified DNA ligase I in several BS cell lines (Willis and Lindahl, 1987). However, no coding mutations have been encountered in the ligase I gene of a number of BS patients (Strathdee et al., 1992; Petrini et al., 1991). Instead two missense mutations occurring in both alleles of the DNA ligase I gene were detected in a human fibroblast strain, 46BR (Barnes et al., 1992). This strain was derived from a patient who displayed symptoms of immunodeficiency, stunted growth, and sun sensitivity. Other laboratories have found Bloom's syndrome cells to have altered uracil-DNA glycosylase activity. Nevertheless, the disorder for Bloom's syndrome has not been convincingly identified.

FA is a disease characterized by skeletal abnormalities, bone marrow hypofunction, mental deficiency, and leukemia. This disease displays a high incidence in spontaneous chromosome damage such as gaps, breaks, and chromosomal translocations. FA is thought to be caused by a defect in the ability to repair DNA interstrand cross-links. A gene conferring wild-type resistance to DNA cross-linking agents upon transfection into cells of FA complementation group C recently has been identified (Strathdee et al., 1992). Oxidative DNA damage and higher than normal levels of 8-oxoguanine have also been found associated with FA, and particularly FA-A.

Clinical symptoms of AT include telangiectasia, cerebellar ataxia, immunodeficiency, and neurological abnormalities. AT is characterized by hypersensitivity to X-irradiation as well as several other DNA-damaging agents and shows an increase in spontaneous chromosome rearrangements. AT cells have recently been found to be defective in their ability to inhibit DNA synthesis after exposure to exogenous mutagens. In fact, three participants (AT genes, p53, and GADD45) were identified which are involved in the signal transduction pathway that controls cell cycle arrest following DNA damage (Kastan et al., 1992). Abnormalities in this pathway have the potential to adversely affect cell survival and genomic integrity following certain types of DNA damage.

The present invention also involves the treatment of these and other malignancies. The types of malignancies that may be treated, according to the present invention, is limited only by the involvement of a BER protein, for example, APE and/or MGMT in DNA repair. By involvement, it is not even a requirement that MGMT-APE be mutated or abnormal—the expression of this fusion protein may actually overcome other lesions within the cell.

A. Genetic Based Therapies

One of the therapeutic embodiments contemplated by the present inventors is the intervention, at the molecular level, in the events involved in the DNA damage Specifically, the present inventors intend to provide, to a cell undergoing DNA damage as a result of any of the exogenous or endogenous insults described above, an expression construct capable of providing, a fusion protein as exemplified by MGMT-APE to that cell. Any nucleic acid encoding a DNA repairing fusion protein as described herein, could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{11}$, $1 \times 10^{12}$ or $1 \times 10^{13}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for various disease types. The section below on routes contains an extensive list of possible routes. For practically any disease, systemic delivery is contemplated. Where discrete disease sites may be identified, a variety of direct, local and regional approaches may be taken. For example, in an individual having a tumor, the tumor may be directly injected with the expression vector encoding the fusion protein in combination with the chemotherapy. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated disorders. In an ex vivo embodiment, cells from the patient are removed and maintained outside the body for at least some period of time. During this period, the cells are transfected with a nucleic acid encoding a fusion protein of the present invention, after which the cells are reintroduced into the patient; in this manner it is possible to confer protection to the cells from the deleterious effects of chemotherapy in, for example, cancer patients.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way MGMT-APE may be utilized according to the present invention.

Since first described in 1984 (Williams et al., 1984), retroviral mediated gene transfer has been shown as an effective means of transduction of murine hematopoietic stem and progenitor cells. In many studies to date, long term reconstituting murine hematopoietic stem cells, assayed in primary and secondary recipients have been transduced using various ex vivo protocols (Moritz and Williams, 1994; Mulligan, 1993). Expression, although variable, has been shown to be stable in vivo in some cases for the lifetime of the experimental animal (Miller, 1992). The success of gene transfer methods in murine systems has not been matched by success in protocols involving large animals species or initial human gene therapy trials (Marshall, 1995). The major limitations evident in gene transfer studies in these larger species is inefficient transduction of long-lived reconstituting hematopoietic stem cells and silencing of the transduced gene sequence in vivo. The slow pace of progress in this area has been contributed to, at least in part, by the lack of an appropriate model for human hematopoietic stem cells, either in vivo or in vitro. In spite of the lack of demonstrable success in human gene therapy trials from a therapeutic standpoint, to date the use of recombinant retroviral vectors has proven safe (Cornetta, 1992).

Several recent advances hold promise for more successful application of gene transfer technology in cancer therapies in the future. Two in vivo models of human stem cell transplants have been successfully developed using human/mouse (Kamel-Reid and Dick, 1988) and human/sheep xenografts (Zanjani et al., 1994; Srour et al., 1993). Both models utilize transplantation of putative human hematopoietic stem cells into immuno-incompetent xenobiotic recipients. Although the relationship between the reconstituting hematopoietic stem cell responsible for long term hematopoiesis in humans and the reconstituting cell identified in these xenograft assays is not established, data in human-SCID/NOD transplants from the inventors laboratory (Larochelle et al., 1996) suggest that a cell more primitive than an hematopoietic progenitor cell can be assayed in this model. The availability of these assays systems may lead to improved gene transfer protocols in the future.

B. Protein Therapy

Another therapy approach is the provision, to a subject, of MGMT-APE polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

C. hAPE and Endogenous $Ca^{2+}$

Another aspect of the invention relates to modulating the level of expression of endogenous hAPE in human cells such as HL60 cells by increasing or decreasing the calcium ion level in the cells. In particular, the expression of hAPE can be upregulated by lowering the level of calcium ion in the cells, e.g., by the addition of a calcium ionophore, and the expression of the HAPE can be downregulated by increasing the level of calcium ion in the cells, for example by adding to the cells a calcium salt such as calcium chloride. Thus, in accordance with the invention, methods are provided for increasing or decreasing hAPE expression in a cell by increasing or decreasing, respectively, the calcium ion level in the cell. For example, upregulation of the endogenous hAPE gene can be used to result in increased resistance of the cells to the chemotherapeutic agents as discussed above.

D. Combined Therapy with Immunotherapy, Traditional Chemo- or Radiotherapy

DNA alkylating agents are an important part of most dose-intensification protocols. In spite of increased use of myeloid growth factor and stem cell support, a dose limiting toxicity of many chemotherapeutic alkylating agents is their toxic effects on non-target tissues such as bone marrow cells. In order to overcome the myelosuppression observed in such therapy, one approach is to increase the level of DNA repair proteins in hematopoietic stem and progenitor cells. Towards this goal the inventors have constructed human fusion proteins that couple MGMT to APE resulting in a fully functional protein for both $O^6$ methylguanine repair and for AP site repair.

Thus, the constructs of the present invention may be combined to yield a more effective chemotherapeutic and radiotherapeutic regimen. The administration of these constructs may also be combined with other gene therapies. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that MGMT-APE therapy could be used in conjunction with chemo- or radiotherapeutic intervention. It also may prove effective to combine MGMT-APE gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with at least one chemotherapy agent at the same time as contacting non-target cells with the MGMT-APE expression construct. These combinations would be provided in a combined amount effective to kill or inhibit proliferation of the target cell but allowing the non-target cells, such as bone marrow cells, to escape the deleterious effects of the chemotherapy. This process may involve contacting the non-target cells with the expression construct and the target cells with the chemotherapeutic agent(s) or factor(s) at the same time.

Alternatively, the APE-MGMT gene therapy treatment may precede or follow the chemotherapy agent treatment by intervals ranging from min to wks. In embodiments where the chemotherapy agent and fusion protein expression construct are applied separately to the organism, one would generally ensure that a significant period of time did not expire between the time of each delivery, such that the agent and expression construct would still be able to exert an advantageously combined effect on the organism. In such instances, it is contemplated that one would contact the organism with both modalities within about 12–24 h of each other and, more preferably, within about 6–12 h of each other, with a delay time of only about 12 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either MGMT-APE or the other agent will be desired. Various combinations may be employed, where MGMT-APE is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing of cancer cells and yet retain the normal growth of the non-cancer cells, both agents are delivered to a organism in a combined amount effective to kill the cancer (target) cell and leave the non-target cell intact.

Thus the compositions of the present invention will be useful in treating patients who are undergoing chemotherapy with agents that induce DNA damage such as, γ-irradiation, X-rays, UV-irradiation, microwaves, electronic emissions, and the like, as well as a variety of chemical compounds, also described as "chemotherapeutic agents,". Such agents include, e.g., adriamycin, 5-fluorouracil (5FU), etoposide (VP-16), camptothecin, cytoxan (cyclophosphamide), thiotepa (thioplex) actinomycin-D, mitomycin C, cisplatin (CDDP) and even hydrogen peroxide. In certain embodiments, the use of BCNU in combination with a MGMT-APE expression construct is particularly preferred as this compound is commonly used to treat brain tumors, lymphomas, breast lung and gastrointestinal cancers and is toxic to bone marrow cells because they possess only low levels of DNA repair activities.

The inventors propose that the regional delivery of MGMT-APE expression constructs to patients receiving chemo- or radiotherapy will be a very efficient method for delivering a therapeutically effective gene to counteract the deleterious effects of the therapy in the non-cancerous cells. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

E. Formulations and Routes for Administration to Patients

Where clinical applications are contemplated, it will be necessary to prepare pharmaceutical compositions— expression vectors, virus stocks, proteins, antibodies and drugs—in a form appropriate for the intended application. Generally, this will entail preparing compositions that are essentially free of pyrogens, as well as other impurities that could be harmful to humans or animals.

The chemotherapy agents can be administered orally, intravenously, intramuscularly, intrapleurally or intraperitoneally at doses based on the body weight and degree of disease progression of the patient, and may be given in one, two or even four daily administrations. Dosages range from about 0.5 mg/kg per day up to tens and even hundreds of mg/kg per day. In addition, optionally, myelosuppressives may be co-administered with the chemotherapeutic agent, or may be administered separately, either before and concurrently with the chemotherapy agent. Dosages of the myelosuppressive agent may vary widely, depending on several factors including the body weight of the patient and on the type and amount of chemotherapy agent administered. Suitable dosages, for example, may be up to about 100 g/kg or more per day, e.g., from about 3 g/kg per day to about 100 g/kg per day, with the precise dosage being determined in accordance with the situation at hand. The dosage of myelosuppressive agent will in general be sufficient to increase the percentage of myeloid cells in the slow-cycling phase so as to achieve myeloprotection, and may be administered intravenously, intramuscularly or intraperitoneally, for example.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. Transgenic Animals

Another aspect of the invention provides transgenic animal models in which essentially all cells of the animal express, and preferably overexpress, a recombinant DNA repair protein such as one of those disclosed above, and/or a fusion of multiple DNA repair proteins as discussed above. Such models will be highly useful, for instance, in the study and screening of chemotherapeutic agents, and in research related to DNA repair processes.

In one embodiment of the invention, transgenic animals are produced which contain a functional transgene encoding a functional MGMT-APE polypeptide or variants thereof. Transgenic animals expressing MGMT-APE transgenes, recombinant cell lines derived from such animals and transgenic embryos may be useful in methods for screening for and identifying agents that induce or repress function of MGMT-APE. Transgenic animals of the present invention also can be used as models for studying indications such as cancers.

In one embodiment of the invention, a MGMT-APE transgene is introduced into a non-human host to produce a transgenic animal expressing a human or murine MGMT-APE gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace or augment the endogenous DNA repair enzymes MGMT-APE by homologous recombination between the transgene and the endogenous gene; or the endogenous gene may be eliminated by deletion as in the preparation of "knock-out" animals. Typically, a MGMT-APE gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress MGMT-APE or express a mutant form of the polypeptide.

As noted above, transgenic animals and cell lines derived from such animals may find use in certain testing studies. In this regard, transgenic animals and cell lines capable of expressing an MGMT-APE or other fusion polypeptide of the present invention may be exposed to substances such as the typical chemotherapeutic agents disclosed above to determine whether the expression of the MGMT-APE fusion protein confers protective properties against such agents.

VI. Examples

The following examples are included to demonstrate preferred embodiments of the invention. It should be appreciated by those of skill in the art that the techniques disclosed in the examples which follow represent techniques discovered by the inventors to function well within the practice of the invention, and thus can be considered to constitute preferred modes for of practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Materials. Enzymes and chemicals were purchased from Amersham (Arlington Heights, Ill.), GIBCO BRL (Gaithersburg, Md.), New England BioLabs (Beverly, Mass.), Pharmacia (Piscataway, N.J.), Promega (Madison, Wis.), Boehringer-Mannheim (Indianapolis, Ind.) and Sigma (St. Louis, Mo.). Radioisotopic [$\alpha$-32P]dCTP (3000 Ci/mmol) and [$\gamma$-$^{32}$P]ATP (3000 Ci/mmol) were purchased from NEN (Wilmington, Del.), [$^3$H]UTP (15 Ci/mmol) was purchased from Amersham.

Molecular Biology and Biochemistry Techniques. DNA sequencing was performed in the Macromolecular facility in the Department of Biochemistry and Molecular Biology using an Applied Biosystems Automated Sequencing System and fluorescent labeling. DNA isolation, RNA isolation, Northern and Western blot analysis, SDS-PAGE, and GST-fusion protein production and purification were performed as has been previously described (Wilson et al., 1994b; Wilson et al., 1995; Yacoub et al., 1996).

$O^6$-methylguanine DNA methyltransferase activity using the 18-mer oligonucleotide assay was performed as described (Maze et al., 1996; Wilson et al., 1994b; Wilson et al., 1995; Yacoub et al., 1996), while AP assays were performed using the inventors' standard procedure (Yacoub et al., 1996). Briefly, the abasic assay utilized a 37 bp 5' $^{32}$P-end-labeled duplex DNA fragment (AP-37-mer) was used as previously described (Yacoub et al., 1996) and reaction mixtures (10 $\mu$l) containing 1 pmol of 5' end-labeled AP-37-mer, 50 mM HEPES, pH 7.5, 50 mM KCl, 1 $\mu$g/ml BSA, 10 mM $MgCl_2$, 0.05% Triton X-100 and the protein of interest. The DNA reaction products were separated on a 20% polyacrylamide gel containing 7M urea. Dried gels were subjected to autoradiography for visualization and densitometric analysis using Sigma Scan software package (Jandel Scientific). Cell culture and cell protection assays for *E. coli* or HeLa cells has been described (Maze et al., 1996; Yacoub et al., 1996).

Construction of the MGMT-APE or MGMT-dl151APE chimeric molecules in pGEX and MSCV vectors. APE and APN-1 cDNAs were generated and the MGMT-APE fusion gene was constructed using the overlapping PCR™ technique previously used in the present inventors' lab (Morgan et al., 1993; Ho et al., 1989) (see FIG. 1A and sequences of fusions, attached hereto). Briefly, the human MGMT (5' primer 5'-CCG GAA TTC ATG GAC AAG GAT TGT-3'

(SEQ ID NO:13)and 3' primer 5'-CTT TTT CCC ACG CTT CGG GTT TCG GCC AGC AGG CGG-3'(SEQ ID NO:14)) and human APE (5' primer 5'-CCG CCT GCT GGC CGA AAC CCG AAG CGT GGG AAA AAG-3' (SEQ ID NO:15) and 3' primer 5'-GGC CGT CGA CAT CAC AGT GCT AGG-3' (SEQ ID NO:16) cDNA sequences were separately amplified. The 5' primer of the MGMT included EcoRI sequences for subsequent cloning into pGEX and the 3' MGMT primer contained an additional 18 nucleotides of the 5' end of the APE coding region. The 5' primer for the APE PCR™ included 18 nucleotides from the 3' coding region of the MGMT cDNA, with the stop codon removed and the 3' primer included sequences for the restriction enzyme SalI. These PCR™ products (653 bp for hMGMT and 986 bp for hAPE) were purified and combined in a second PCR™ reaction to amplify a 1603 bp human MGMT-APE product by utilizing the MGMT 5' primer with the APE 3' primer. All amplifications were kept under 30 cycles and large amounts of template were used to decrease the possibility of PCR™ nucleotide changes. The PCR™ products were purified and the 1.6 kb human MGMT-APE fragment double digested with EcoRI and SalI, and ligated into the EcoRI/SalI cloning site in pGEX 4T-1. After transformation into competent cells the colonies containing pGEX 4T-1 MGMT-APE were confirmed by PCR™ and restriction digest, and DNA sequencing was used to confirm the integrity of the human MGMT and APE sequence.

The other construct, MGMT-dl151APE, was constructed in a similar manner. The deletion of the first 150 amino acids of the human APE was performed using PCR™ and primers that contained the carboxyl end of MGMT and APE nucleotide sequences starting at amino acid 151 of the APE protein sequence (5' primer starting at amino acid 151 of APE; 5'-CCG CCT GCT GGC CGA AAC CAT GAT CAG GAA GGC CGG-3', SEQ ID NO:4). The amplified products were purified, combined and overlapping PCR™ performed as described above. The 1.2 kb human MGMT-dl151APE purified fragment was double digested with EcoRI and SalI, and ligated into the EcoRI/SalI cloning site in pGEX4T. Positive colonies were confirmed by PCR™ and restriction digestion and sequenced as described above.

Construction of retroviral constructs. The MGMT-APE and MGMT-dl151APE chimeric sequences were removed from the pGEX4T constructs by XhoI and EcoRI gel purified and ligated into the EcoRI/XhoI cloning site of the retroviral vector MSCV2.1 (obtained from Dr. Robert Hawley). HB101 cells were transformed with MSCV2.1 MGMT-APE and MGMT-dl151APE ligation products and positive clones were identified by PCR™ and restriction digestion.

Retroviral producer cells were generated by transfection of 2 μg of purified plasmid DNA (Qiagen, Chatsworth, Calif.) added to the Lipofectin transfection reagent (GIBCO-BRL) into GP+AM12 cells (Markowitz et al., 1988a; Markowitz et al., 1988b) following the protocol obtained from the manufacturer. Clones were selected using 0.75 mg/ml G418 (dry powder; GIBCO-BRL) and individual clones titered on NIH3T3 cells. High titer clones were used to infect HeLa cells in α-MEM medium (GIBCO-BRL) supplemented with 10% FBS (Hyclone, Logan, Utah) and 10 μg/ml polybrene. After infection, HeLa cells were selected for G418 resistance, as above. Individual clones were isolated and examined for expression using Northern and Western blot analysis.

Survival assays. HeLa cells containing each construct were plated into a 6 well plate (Corning Costar, Cambridge, Mass.) and cultured overnight at 37° C. at 5% $CO_2$. The next day, the cells were washed and treated for 1 h with 0–150 μM 1,3-bis(2-chloroethyl)-nitrosourea (BCNU; Drug Synthesis and Chemistry Branch, Developmental Therapeutics Program, Division of Cancer Treatment, NCI, Bethesda, Md.) and 0–2 mM methyl methanesulfonate (MMS; Aldrich, Milwaukee, Wis.). Seven d later the cells' viability was determined using trypan blue stain and compared with untreated cells and cells with vector alone. Studies were performed in triplicate and repeated three times. Statistical analysis was performed using SigmaStat (Jandel Scientific) software package (t-test and ANOVA).

EXAMPLE 2

Chimeric MGMT-APE Construction

The MGMT-APE fusion was constructed using the overlapping PCR™ technique that has been previously used in the inventors' laboratory (Morgan et al., 1993). Briefly, the inventors separately amplified the human MGMT and human APE cDNA sequences (FIG. 1A). The 5' primer of the MGMT included EcoRI sequences for subsequent cloning into pGEX4T and the 3' MGMT primer contained an additional 18 nucleotides of the 5' end of the APE coding region. The 5' primer for the APE PCR™ included 18 nucleotides from the 3' coding region of the MGMT cDNA, with the stop codon removed and the 3' primer included sequences for the restriction enzyme SalI (FIG. 1A). These PCR™ products (653 bp for MGMT and 986 bp for APE) were purified and combined in a second PCR™ reaction to amplify a 1603 bp human MGMT-APE product by utilizing the MGMT 5' primer with the APE 3' primer. All amplifications were kept under 30 cycles and large amounts of template were used to decrease the possibility of PCR™-induced nucleotide changes. The PCR™ products were purified and the 1.6 kb human MGMT-APE fragment double digested with EcoRI and SalI, and ligated into the EcoRI/SalI cloning site in pGEX4T-1. After transformation into competent cells the colonies containing pGEX 4T-1 MGMT-APE were confirmed by PCR™ and restriction digest and DNA sequencing was used to confirm the integrity of the human MGMT and APE sequence.

Figure 1B:
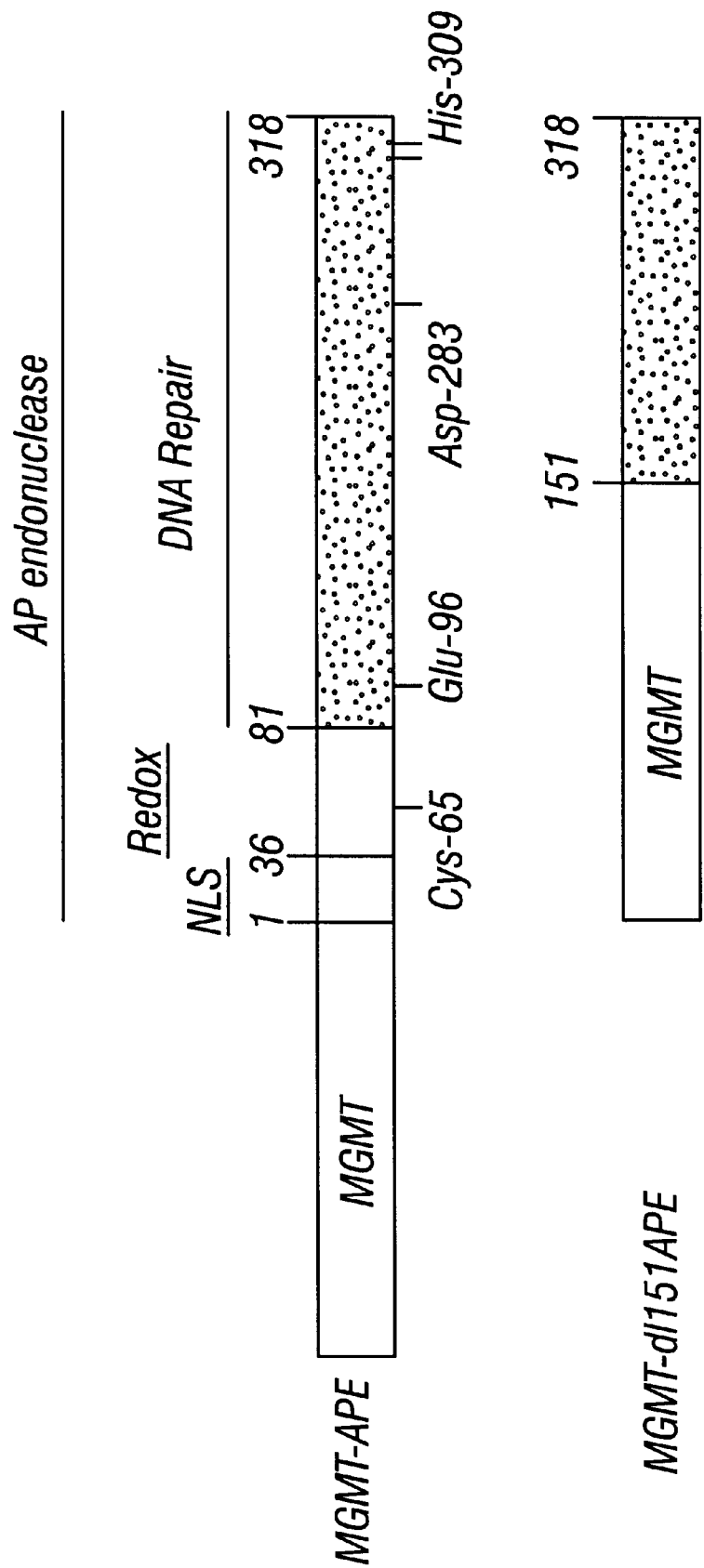

Another construct containing the full-length MGMT coding region, but only amino acids 151–318 of the APE coding region, was made in a similar fashion. This construct was made following the initial reports of AP endonuclease activity residing in the carboxyl region downstream of amino acid 150 (Xanthoudakis et al., 1992) (FIG. 1B). However, subsequent to this report, it is clear only the first 60 amino acids can be deleted without significant loss of AP endonuclease activity (Barzilay et al., 1995b; Barzilay et al., 1995a; Barzilay et al., 1995a); the inventors' results presented below.

EXAMPLE 3

Assays of Function of MGMT-APE Fusion

Figure 2:
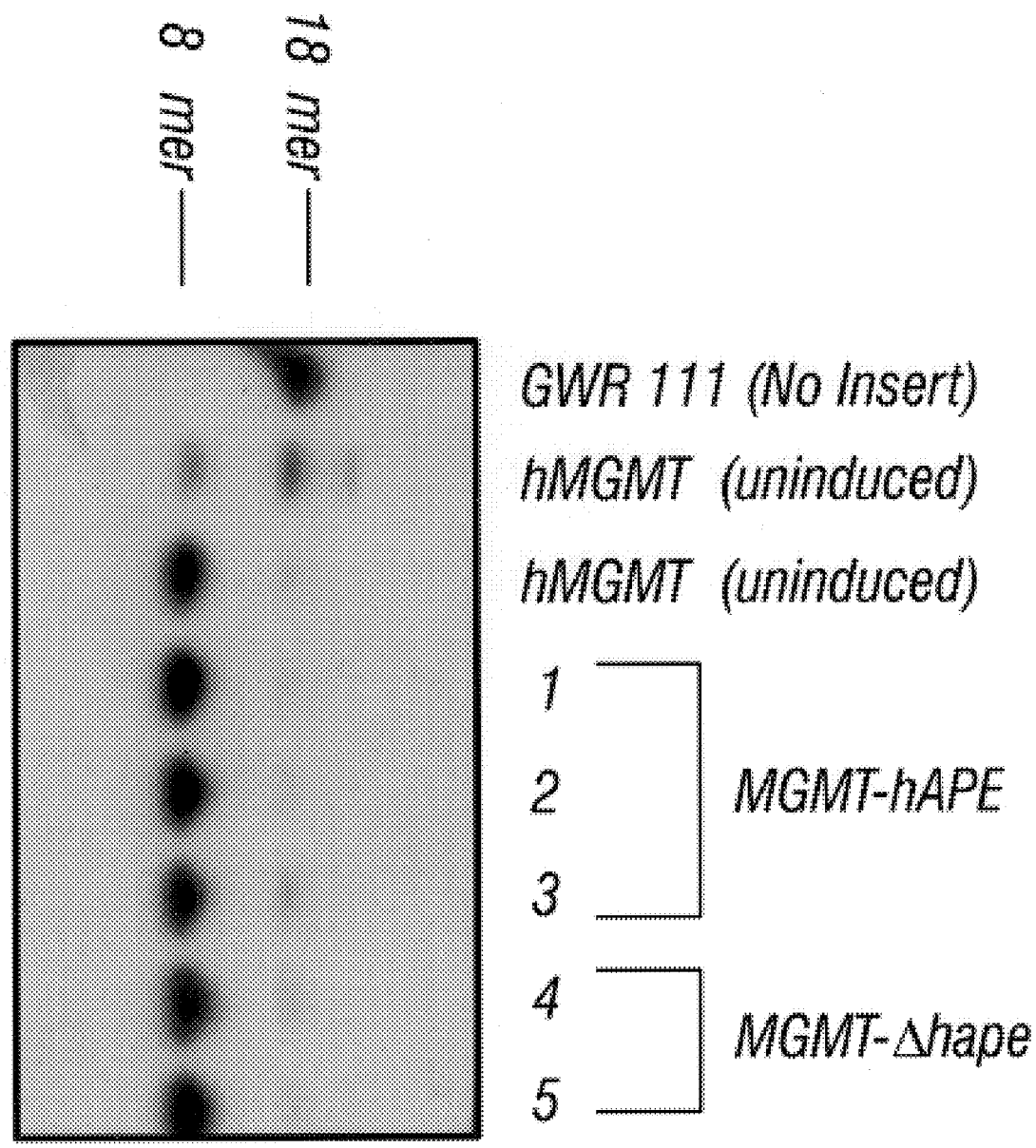
FIG. 2 MGMT activity in chimeric proteins. The human chimeric MGMT-APE and MGMT-d151APE pGEX4T-1 constructs were transfected into $E.\ coli$ ada- ogl (GWR111) cells and expression of the fusion protein induced with IPTG. The 18-mer oligonucleotide assay was employed on the sonicated cell extract (5 μg per assay) to determine the activity of the MGMT portion of the construct.

MGMT activity assay of the chimeric proteins. The full length human chimeric MGMT-APE pGEX4T construct (MGMT-APE) and MGMT with the deleted APE (MGMT-dl151-APE) were transfected into E coli ada⁻ ogt⁺ (GWR111) cells and expression of the glutathione S-transferase (GST) fusion proteins induced with IPTG. The 18-mer oligonucleotide assay was employed on the cell extract to determine the activity of the MGMT portion of the chimeric constructs (Morgan et al., 1993; Wilson et al., 1994a). As shown in FIG. 2, the GWR111 cells are devoid of O$^6$-methylguanine DNA methyltransferase activity, as expected, while all three of the selected full length chimeric clones were as active as the non-chimeric human MGMT clone Two of the selected MGMT-dl151APE clones were also fully active for O$^6$-methylguanine repair (FIG. 2).

Figure 3A:
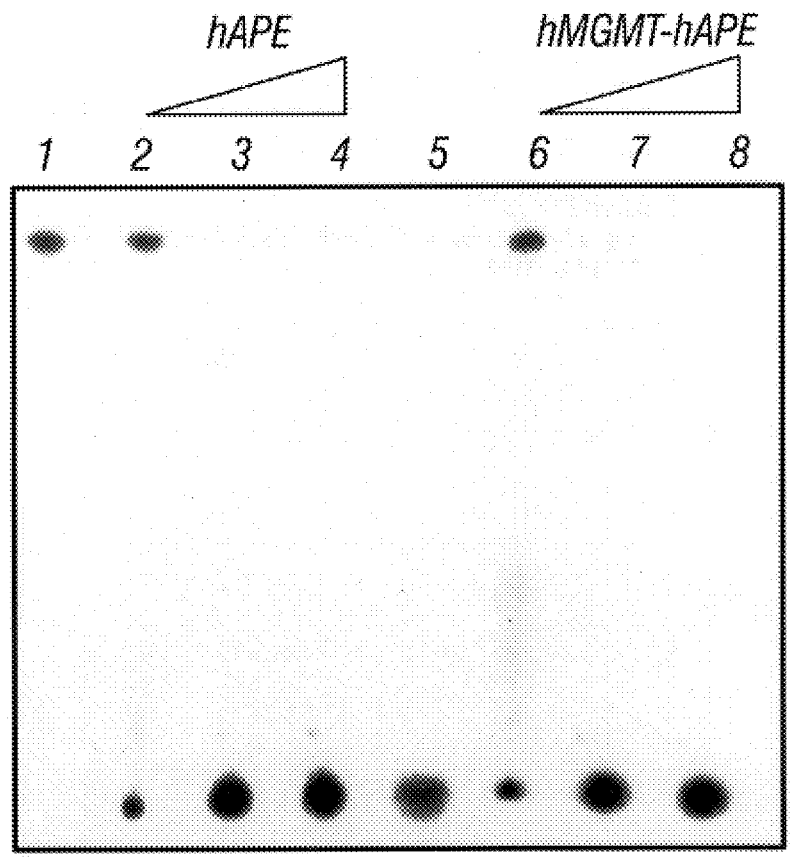
FIG. 3A and FIG. 3B. AP endonuclease activity possessed by the chimeric proteins. Reactions were for 30 min and contained 1 pmol/ AP-37 mer. The DNA cleavage products were separated on a 20% polyacrylamide DNA sequencing gel and analyzed by autoradiography.
Figure 3B:
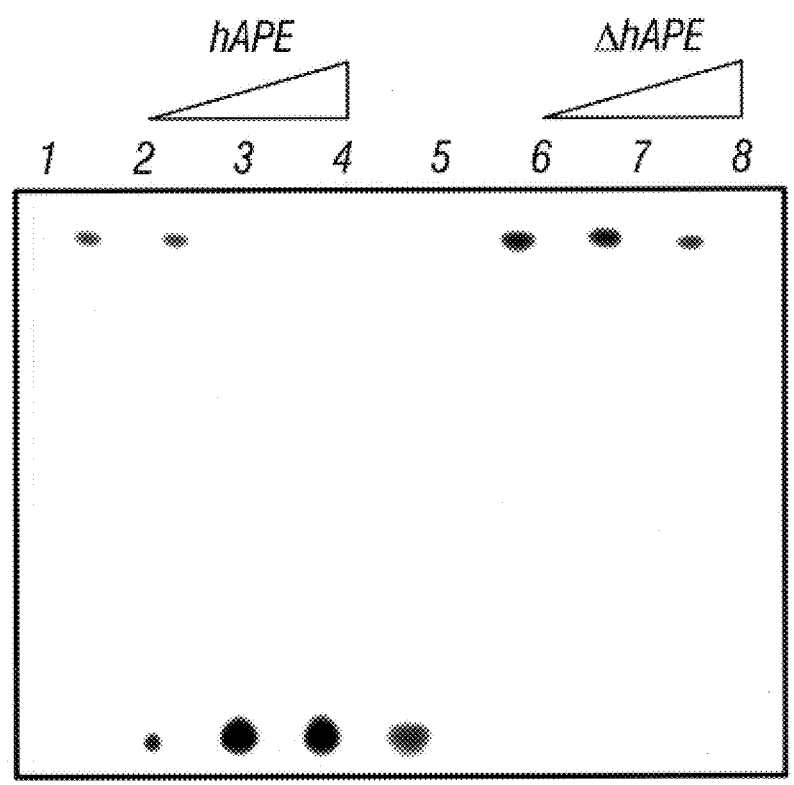

AP endonuclease activity of chimeric clones. The chimeric MGMT-APE and MGMT-dl151APE constructs were transfected into *E. coli* RPCS01 (xth$^-$, nfo-1$^-$) which is deficient for the two major AP endonucleases in *E. coli*, exonuclease III (xth) and endonuclease IV (nfo-1) The fusion protein was overexpressed and soluble supernatant applied to a glutathione-agarose column, washed and the purified MGMT-APE protein eluted with glutathione. This resulted in homogenous preparations of fusion proteins as judged by SDS-PAGE. Concomitantly, APE and dl151APE constructs were prepared in similar fashion as the inventors have previously reported (Yacoub et al., 1996) A 37-mer oligonucleotide with a uracil at position 21 in the $^{32}$P labeled strand was annealed with the complementary unlabeled oligonucleotide and treated with uracil glycosylase to create an AP site in place of the uracil. This assay is similar to the one used for the 8-oxoguanine repair analysis (Yacoub, et al., 1996). As can be seen from FIG. 3A, dilutions of the chimeric MGMT-APE protein (lanes 6–8) were equally as effective on the AP substrate as APE alone (lanes 2–4). The inventors did not detect any APE activity using this assay with the MGMT-dl151APE construct. In order to confirm that the deleted APE was inactive due to the deleted amino acids and not due to the addition of the MGMT moiety to the carboxyl region, the inventors compared non-fusion APE and dl151APE using the AP oligonucleotide assay (FIG. 3B). The inventors did not see any activity with the dl151APE protein (FIG. 3B). Activity in this assay is demonstrated by concentration of the 37-mer (upper band) to an 21-mer (lower band). Subsequently, the MGMT-dl151APE served as a negative control for chimeric AP endonuclease function. In additional studies, the inventors pretreated the MGMT-APE chimeric protein with unlabeled O$^6$-methylguanine oligo substrate that was used in the MGMT assay and then performed the AP assay in order to ascertain whether the stoichometric transfer of the methyl group from the DNA to the MGMT portion of the chimeric protein would hinder AP activity. The inventors found no diminution of APE function in this assay.

EXAMPLE 4

Complementation Studies

Figure 4A:
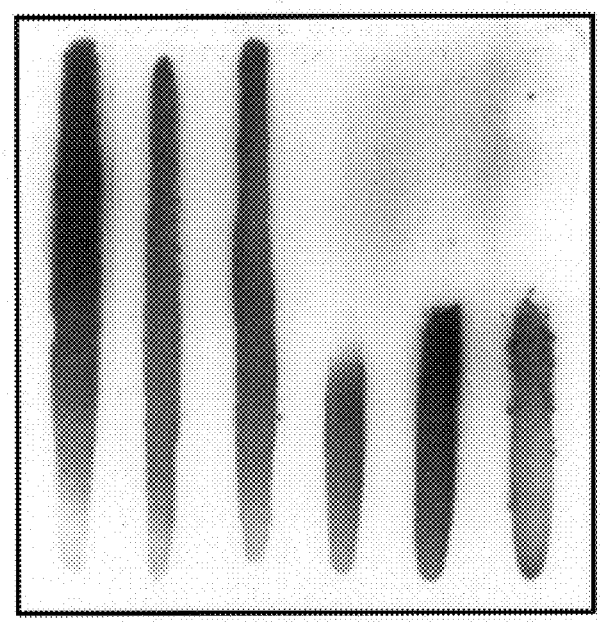
FIG. 4A and FIG. 4B Gradient plate assays to determine in vivo functionality of MGMT-APE fusion protein against MMS (FIG. 4A) or hydrogen peroxide (FIG. 4B).
Figure 4B:

Protection of *E. coli* AP endonuclease deficient mutant cells with MGMT-APE chimera. In order to verify the activity of the chimeric protein in cells and not just in biochemical analyses, two studies were performed using *E. coli* cells that are deficient in AP endonuclease activity. *E. coli* RPC501 (xth$^-$, nfo$^-$) cells with the MGMT-APE and MGMT-dl151APE chimeric constructs in pGEX, as described above, were used on gradient plates with either MMS or H$_2$O$_2$ (Yacoub et al., 1996) The length of the cell growth along the gradient is a measure of the strain's resistance to the agent. Using MMS, the MGMT-APE fully protects the AP endonuclease deficient cells when compared to wild-type levels (FIG. 4A, lane 3), while the MGMT-dl151APE or the dl151APE shows no protection (FIG. 4A, lanes 4 and 5). From the data, it is clear that the chimeric MGMT-APE affords as much protection against MMS as APE alone. APE has previously been shown to protect cells against H$_2$O$_2$ damage (Demple and Harrison, 1994; Demple et al., 1991). Using the gradient plate assay, but with the DNA damaging agent H$_2$O$_2$ (FIG. 4B), the MGMT-APE chimera was shown to protect to nearly wild-type levels. Once again, the MGMT-dl151APE is deficient in its ability to protect from damage requiring AP endonuclease activity.

In the biochemical and *E. coli* protection studies described, the chimeric MGMT-APE protein was attached at the amino end to glutathione-S-transferase (GST), which did not affect either MGMT or APE activity. This suggests that additional repair proteins may be added in lieu of the GST moiety to the inventors' construct in future studies.

EXAMPLE 5

Protection of Mammalian Cells with the MGMT-APE Chimera

The previous Example demonstrated that the chimeric MGMT-APE protein was fully functional for MGMT and APE activity in biochemical and *E. coli* complementation assays, the inventors then proceeded to determine the functionality of the chimera in mammalian cells. In this Example, the MGMT-APE fusion protein was demonstrated to be functional in mammalian cells. The chimeric construct was transfected using lipofectin transfection reagent into GP+Am12 cells, an amphotropic retrovirus packaging cell line. Transient virus harvest was used to infect E86 cells to generate a high titer ecotropic producer. However, GP+Am12 cells were selected under 0.75 mg/ml G418 and individual clones titered. High titer clones were used to infect HeLa cells in -MEM medium supplemented with 10% FBS and 10 g/ml polybrene. After infection, HeLa cells were selected under 0.75 mg/ml G418 for resistance. Clones were analyzed for RNA (Northern) and protein expression (Western) and two were selected for survivability assays in HeLa cells. HeLa cells (15,000) containing each construct were plated into a 6 well plate and cultured overnight at 37 C. at 5% CO$_2$. The next day the cells were washed and treated for 1 h with either 75 or 150 M BCNU (Drug Synthesis and Chemistry Branch, Developmental Therapeutics Program, Division of Cancer Treatment, National Cancer Institute, Bethesda, Md.), 1 or 2 mM MMS, or a mixture of 0.5 mM MMS and 75 M BCNU. Seven to ten d later the cells' viability was determined using trypan blue staining and compared with that of untreated cells.

Figure 5:
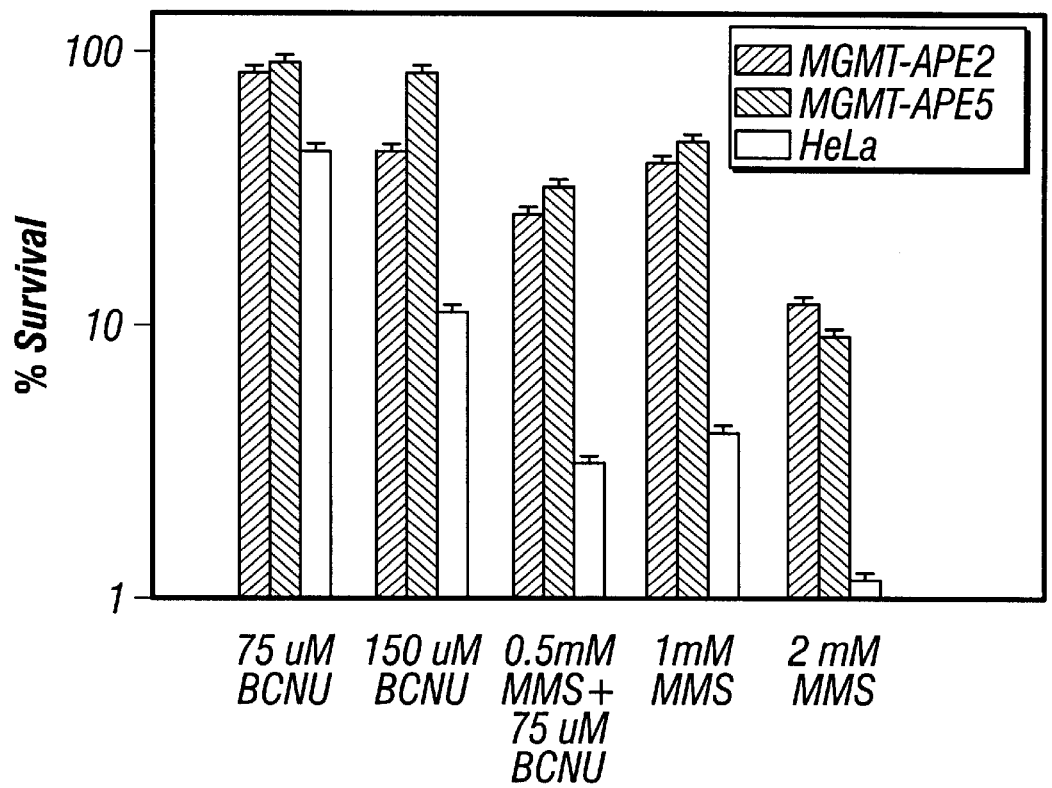
FIG. 5 Protective ability of the MGMT-APE chimera in HeLa cells. Single clones of HeLa cells containing the MGMT-APE chimeric construct were selected for survivability assays in HeLA cells. Tow single clones MGMT-APE 2 and 5) were used in survivability assays. Cells were treated for 1 h with either 75 or 150 μM 1,3, Bis (2-chloroethyl)-nitrosurea (BCNU: Drug Synthesis and Chemistry Branch, Developmental Therapeutics Program, Division of Cancer Treatment, National Cancer Institute, Bethesda, Md.), 1 or 2 mM methyl methane sulfonate (MMS) or a mixture of 0.5 mM MMS and 75 μM BCNU. Studies were performed in triplicate and repeated three time. The differences between the HeLa cells and the chimeric constructs were all at least p<0.05 using the SigmaStat software package.

As seen in FIG. 5, the chimerics have a two-fold (83 and 92% vs. 44%) survival enhancement over the HeLa cells alone at the lower BCNU dose, while at 150 $\mu$M, there is a 4–8 fold enhancement (43 and 86% vs. 11%). For the MMS protection, there was roughly a 10-fold protection level at both the 1 mM (39 and 47% vs. 4%) and 2 mM (12 and 10% vs. 1%). The protection afforded by the chimeric construct against a dual exposure of MMS and BCNU was, again, roughly 10-fold (26 and 31% vs. 3%) (FIG. 5). These results evidence that the chimeric protein should be functional in the protection of bone marrow and other cells against BCNU alone, other alkylating agents (cyclophosphamide, streptozotocin) that produce higher levels of N$^7$-guanine compared to O$^6$-guanine, or other agents which produce AP sites directly, such as bleomycin, and various combinations of BCNU with these other agents.

EXAMPLE 6

Construction and Testing of MGMT/Δ1-60HAPE and MGMT/Δ1-150HAPE

A DNA sequence encoding the full-length MGMT amino acid sequence and all but the first 60 amino acids of the APE amino acid sequence was prepared and tested as described in Example 1 which is fully incorporated as a part of the present application. As demonstrated, the resulting DNA sequence encodes a protein possessing AP endonuclease activity. A DNA sequence encoding the full-length MGMT amino acid sequence and all but the first 150 amino acids of the APE amino acid sequence was prepared and tested as described in Example 1. As demonstrated, the resulting DNA sequence encodes a protein possessing no AP endonuclease activity.

EXAMPLE 7

Construction of Other Chimeric DNAS

The following fusion proteins are prepared by the overlapping PCR™ technique generally as described in Example 1 above: hMPG/hAPE; hMPG/hMGMT/hAPE; hMGMT/APN-I; hAPE/APN-I, or any of the other combinations listed herein. Examples of primers used for the proteins other than hAPE and hMGMT (which are given above) are as follows:

```
hMPG:    5'-ATC GTC ACC CCC GCT TTG-3'     (SEQ ID NO:5)
         5'-GGC CTG TGT GTC CTG CTC-3'     (SEQ ID NO:6)
APN-I:   5'-ATG TGT GCT ATA AAC AAA GCT-3' (SEQ ID NO:7)
         5'-TGA AAT GCT GTT CCG GGA TGC-3' (SEQ ID NO:8).
```

Indeed, the inventors studies have demonstrated that more than APE and MGMT may be added to the fusion protein. This allows for the generation of a fusion protein that contains two or more repair enzymes. Thus, it is contemplated that there are a variety of different combinations of DNA repair protein that may be used in the fusion constructs of the present invention. Table 4 shows three groups of DNA lesion repair proteins. The possible combinations contemplated include the use of one gene from each group; the use of one gene from group 1 and one gene from group 2; the use of one gene from group 1 or group 2 and one gene from group 3; or the use of one gene from groups 1, 2 and 3. Alternatively, a gene from the BER-A pathway (e.g., MPG, APE or APN1, β-polymerase, DNA ligase; FIG. 21A) may be combined with a gene from the BER-B pathway (fpg, dS3, Ogg1, NTG-1, SCR-1, SCR-2, endoIII; FIG. 21B). In yet another alternative, a gene from either or both the BER-A and BER-B pathway may be combined with a gene from the direct reversal pathway (MGMT including mutants thereof). The fusions are tested for activity generally as described in the examples above.

TABLE 4

Proteins that may be used in DNA repair fusion Constructs of the Present Invention

| Group 1: Fapy nad 8oxoG lesions | Group 2: Other oxidative DNA lesions | Group 3: Other oxidative DNA damage: e.g., AP sites |
|---|---|---|
| dS3 | EndoIII (bacterial and human) | MPG or HAAG APE |
| fpg (MutM) | OGG1 (possibly) | APN1 |
| OGG1 | NTG-1 (yeast) | γ-polymerase |
|  | SCR-1 (yeast) | DNA ligase |
|  | SCR-2 (yeast) |  |
| (human MutM homologue) |  |  |

EXAMPLE 8

Cellular Protection Using DNA Repair Constructs

Figure 9A:
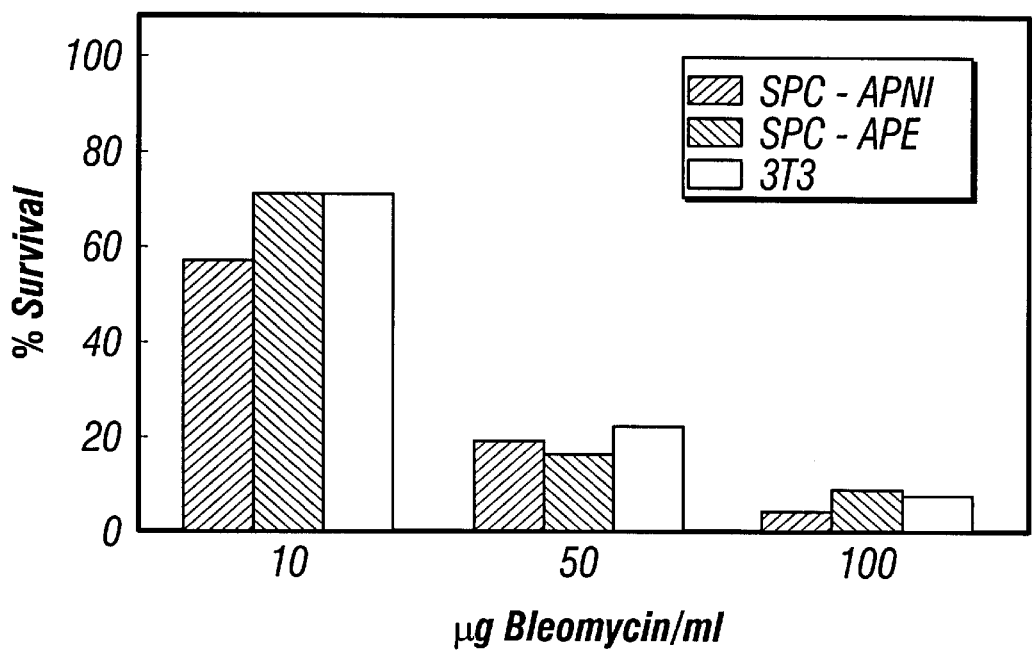
FIG. 9A, FIG. 9B and FIG. 9C. The effect of bleomycin on growth of NIH/3T3 (FIG. 9A) cells and HeLa/SPC cell (FIG. 9B) transfected with DNA repair proteins. The transfected 3T3 cells and the HeLa/SPC cell lines containing the DNA repair constructs (SPC-APE and SPC-APN1) were incubated with media containing bleomycin (0–150 μM) for 1 h, the media was removed, the cells washed and transferred in aliquots of $5 \times 10^4$ cells to new 60 mm plates. Cells were counted after 10 d.
Figure 9B:
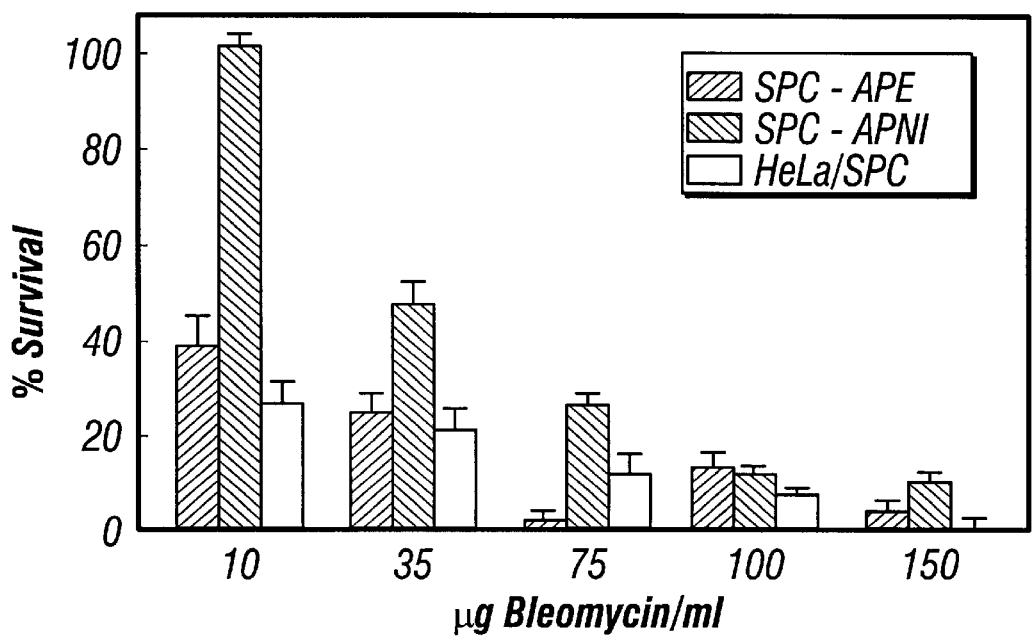

In order to assess whether overexpression of APN1 and APE is associated with protection from bleomycin cytotoxicity, a growth assay was conducted using NIH/3T3 cells and HeLa/SPC cell. The 3T3 cells do not contain the necessary transcription factors for the SPC promoter. Transfection of the plasmids into 3T3 fibroblasts is essentially as described below. Constructs were co-transfected with the neo selectable marker. The transfected 3T3 cells and the HeLa/SPC cell lines containing the DNA repair constructs (SPC-APE and SPC-APN1) were incubated with media containing bleomycin (0–150 $\mu$M) for 1 h, the media was removed, the cells washed and transferred in aliquots of $5 \times 10^4$ cells to new 60 mm plates. Cells were counted after 10 d (FIG. 9A and FIG. 9B).

The 3T3 cells transfected with SPC-APE and SPC-APN1 were not protected from bleomycin toxicity, due to the absence of the SPC transactivating transcription factor. In contrast the HeLA cells harboring the SPC transactivating factor were protected from bleomycin toxicity by both the APE and APN1 DNA repair genes. SPC-APE and SPC-APN1 demonstrated increased resistance to bleomycin at various concentrations of the drug. APN1 afforded better protection against bleomycin toxicity since APN1 is a eukaryotic homologue of the E.coli endonuclease IV APE, while APE in E. coli is actually exonuclease III homologue, and it has previously been shown that endo IV has a greater activity toward bleomycin-induced AP sites compared to exo III.

Figure 6:
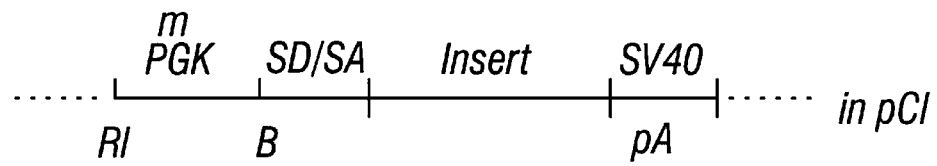
FIG. 6. Expression vector in which the cDNA is expressed by the murine phosphoglycerate kinase promoter (PGK) and contains the SV40 small T intron and poly A tract.

The inventors also confirmed the function of the cloned APN1 and APE cDNAs using an expression vector in which the cDNA is expressed by the murine phosphoglycerate kinase promoter (PGK) and contains the SV40 small T intron and poly A tract, FIG. 6. This plasmid is used to make transgenic mice as outlined below.

Both APN1 and APE cDNAs were subcloned 3' to the PGK promoter via SalI and EcoRI or SalI and HindIII sites, respectively. For transfection into the mouse 3T3 fibroblast cell line, 100 g of each of the constructs was purified and the plasmids were co-transfected into 3T3 fibroblasts utilizing DOTAP and a vector with the neo selectable marker. Positive clones were selected using G418 and cultured into separate wells of a 24 well plate. PCR™, Southern and Northern analysis were performed to detect cell lines carrying the transfected AP endonuclease sequences and expression levels. A number of positive clones were selected and used for protection studies.

Figure 9C:
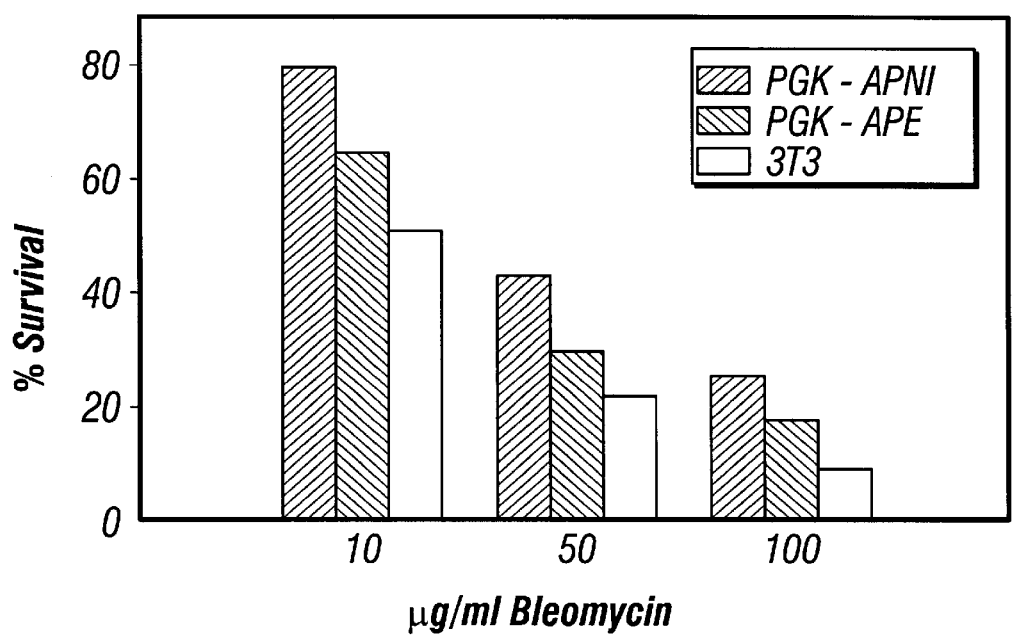

Mouse 3T3 fibroblasts cell lines that expressed the AP endonuclease DNA repair constructs (PGK-APNI and PGK-APE) were grown to confluency on 60 mm tissue culture plates. The normal growth media was replaced with media containing either 0, 10, 50 or 100 g/ml bleomycin. Bleomycin was made up as a 4 mg/ml solution in 0.9% NaCl; the 0 M dose was 0.9% NaCl. After 1 h of treatment, the media was removed, the cells washed twice with PBS and detached from the plates with 0.5 ml 0.25% trypsin-EDTA. 1.5 ml normal growth media was added to each plate and $5 \times 10^4$ cells were aliquoted to new 60 mm plates with 5 ml fresh growth media. Cells were counted after 7–10 d following trypan blue staining. As seen in FIG. 9, both PGK-APN1 and PGK-APE transfected NIH/3T3 cells demonstrate increased resistance to bleomycin at three different concentrations of drug, even though PGK is a relatively weak promoter in these cells.

These same constructs, and constructs containing the other fusions reported in these Examples above, are used to generate transgenic mice generally as described below. In addition, recombinant retroviral vectors are constructed by ligating each cDNA into the polylinker site of MSCV 2.1. E86 producer cell lines of each of these constructs are generated with relatively high titers, for specific illustrative examples: MSCV 2.1-APE: $3 \times 10^5$ cfu/ml; MSCV 2.1-APN1:$1 \times 10^5$ cfu/ml; MSCV 2.1-MGMT-APE: $1 \times 10^5$ cfu/ml; all on NIH/3T3 cells), and in vitro studies on resulting transformed murine bone marrow cells are conducted to ascertain biological activities.

Figure 7:
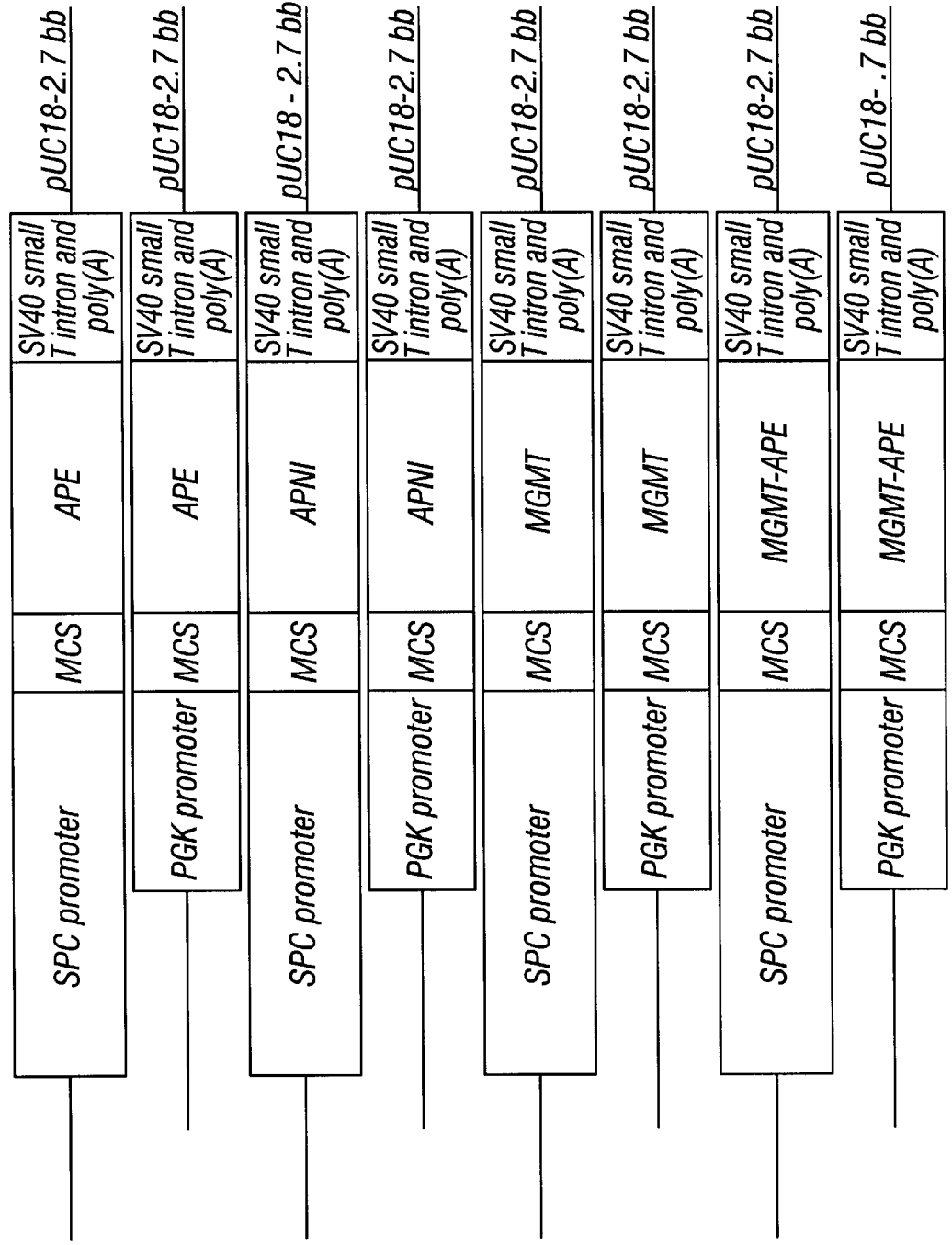
FIG. 7. Modified plasmid, pPGKCI in which the CMV promoter is replaced with the murine PGK promoter.

Conventional pronuclear-injection derived transgenic mice are also generated. Each cDNA described above is inserted into a modified pC1 plasmid (Promega) for pronuclear injection. For example, in the modified plasmid, pPGKCI (FIG. 7), the CMV promoter is replaced with the murine PGK promoter. The functional splicing signals and SV40 poly A sequences contained in the pC1 plasmid are maintained. The CMV promoter and enhancer have been replaced by PGK, since it has previously been demonstrated persistent expression of several introduced cDNAs in multiple tissues of transgenic mice (Yacoub et al., 199633). Plasmids will be injected into pronuclei of C3H/HeJ mice as generally described in Hogan et al. (1986). Transgenic mice derived from these injections are analyzed for the presence and expression of the transgene by Southern blots of tail DNA and RNA and protein (Western) analysis of bone marrow cells.

EXAMPLE 9

In vivo Testing

Bone marrow cells are transduced with recombinant vectors containing DNA sequences as described herein and transplanted into lethally-irradiated syngeneic recipients, such as mice. Animals are treated with BCNU beginning three wk after transplantation and are analyzed for resistance to the treatment. In addition to BCNU treatment, mice transplanted with APE, APN1 and MGMT-APE constructs are treated with bleomycin and STZ, and the result analyzed for enhanced resistance to the agents.

EXAMPLE 10

Study of Natural Expression Pattern for Repair Protein APE in Hematopoietic Cells The function of base excision repair (BER) in hematopoietic cells was investigated by analyzing the expression of APE in CD34+ purified peripheral blood stem/progenitor cells and in differentiated progeny of these cells. Peripheral blood mononuclear cells were obtained by apheresis of volunteer normal adult subjects that had been mobilized for 5 d with subcutaneous injections of recombinant human granulocyte-colony stimulating factor (rhG-CSF). CD34-positive (CD34+) hematopoietic progenitor cells were isolated using a commercially available kit according to the manufacturers suggested protocol (Miltenyi Biotec, Auburn, Calif.). Highly pure (88 6%, mean s.d., n=7) CD34+ cells were obtained with high yields (77 7%, n=7) recovered using this enrichment method.

Figure 8A:
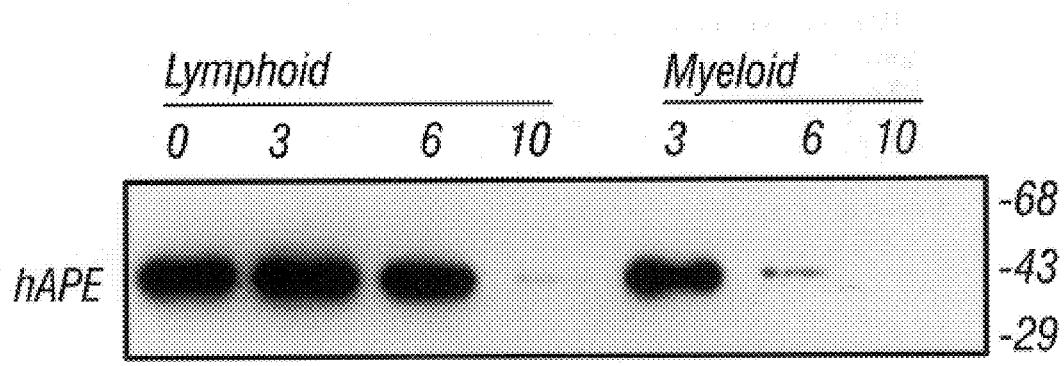
FIG. 8A and FIG. 8B. Determination of APE expression by Northern analysis following RNA isolation and via Western blotting of electrophoresed cell lysates from haematopoietic cells.
Figure 8B:
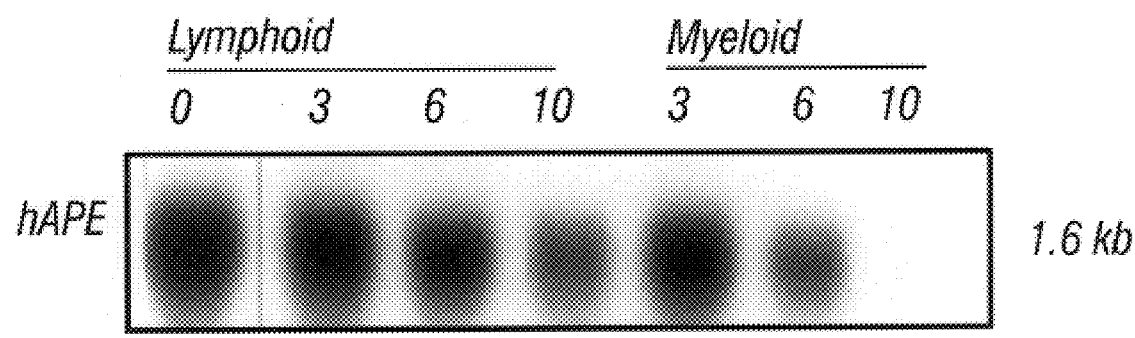

CD34+ cells were grown in vitro at a concentration of $1 \times 10^5$ cells/ml in Iscove's modified Dulbecco's medium (IMDM) supplemented with 10% fetal calf serum (FCS), 1% L-glutamine, and 2% Penicillin-Streptomycin using a modification of the protocol reported by Berliner et al. For myeloid differentiation conditions, the culture medium was supplemented with recombinant human growth factors, interleukin-3 (rhMGMT) 100 ng/ml (Peprotech, Rocky Hill, N.J.), stem cell factor (rhSCF) 100 ng/ml, and 10 ng/ml rhG-CSF (Amgen, Thousand Oaks, Calif.). For lymphoid differentiation conditions, the culture medium was supplemented with 100 ng/ml rhSCF and 250 U/ml rbIL-7 (Peprotech). Cells were fed with fresh medium containing the appropriate cytokines every 72 h. Hematopoietic cells were harvested 3, 6, and 10 d after initiation of the cultures and cells were analyzed for differentiation by morphologic criteria following Wright-Giemsa staining of cytospin smears and cell-surface antigen expression via monoclonal antibody staining and flow cytometric analysis using a FACStar instrument (Becton Dickinson, San Jose, Calif.). A large aliquot of cells was processed for determination of APE expression by Northern analysis following RNA isolation and via Western blotting of electrophoresed cell lysates. During this in vitro culture, significant numbers of myeloid and lymphoid progenitor and precursor cells are being generated. As can be seen in FIG. 8, as the CD34+ cells differentiate down both the myeloid and lymphoid paths, the level of 37 kDa APE protein declines (left panel) and the level of the APE 1.6 kb mRNA declines (right panel). By d 10, no detectable levels of either protein or mRNA are found after differentiation in myeloid growth factors, even though large numbers of progenitor and precursor cells remain in these cultures. Furthermore, the level of APE protein and RNA is significantly different on d 10 in the myeloid cells in comparison to the lymphoid cells. Thus, differentiation of primitive CD34+ human cells and the generation of large numbers of myeloid committed progenitor cells is accompanied by a significant decrease in the level of APE mRNA and the level of protein as measured by Western blot. These data suggest that transduction and expression of the APE cDNA may prevent this down regulation of APE protein during myeloid differentiation.

EXAMPLE 11

Protection from the Deleterious Effects of Oxidative DNA Damaging Agents Using S3, FPG and ENDO III Gene Products The present example provides evidence that other DNA repair genes such as S3, FPG and endo III gene products are also successful in protecting cells from the deleterious effects of oxidative DNA damaging agents.

Biochemical Properties of S3

Figure 10:
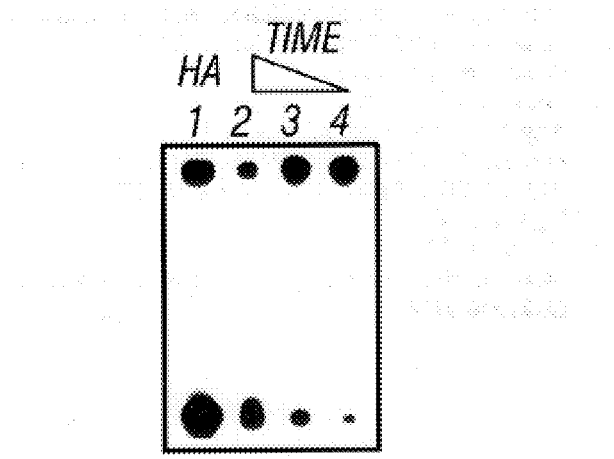
FIG. 10. Time dependence of GST-dS3 mediated cleavage at sites of 8-oxoG. Incubations contained 1 pmol of 8-oxoG-37 mer and 100 pg of GST-dS3. The DNA reaction products were separated on a urea-containing 20% polyacrylamide gel and analyzed by autoradiography. Lane 1, hot piperidine (HA) to gene ate a β, δ-elimination product. Incubations with GST-dS3 were for 10 min. (lane 4), 20 min. (lane 3) arid 30 min. (lane 2)

The inventors recently reported that glutathione S-transferase (GST) fusion constructs of Drosophila ribosomal protein S3 (GST-dS3) contained AP lyase activity (Wilson et al., 1994). Since all known AP lyases identified in prokaryotes and eukaryotes also contain associated DNA glycosylase activity (Doetsch and Cunningham, 1990; Boiteux et al., 1987), the inventors further tested the ability of GST-dS3 to act on a heavily UV-irradiated DNA substrate. It was found that the GST-dS3 protein cleaved irradiated DNA at a guanine photoproduct which was later determined to be 2,6-diamino-4-hydroxy-5-formamidopyrmidine (FapyGua; results obtained from Dr. Paul Doetsch and Laura Augeri, Emory University). An intermediate in the formation of FapyGua is 8-oxoG (Steenken, 1989; Doetsch et al., 1995), which represents, unlike FapyGua, an abundant form of DNA damage caused by oxidative stress (Gajewski et al., 1990). The inventors therefore investigated this form of DNA damage, utilizing a 5' end-labeled DNA duplex oligonucleotide that contained a single 8-oxoG residue (8-oxoG-37 mer). The purified GST-dS3 fusion construct was incubated with 8-oxoG-37 mer, and the products of the reaction subsequently analyzed on a DNA sequencing gel. The purified GST-dS3 protein was found to specifically introduce DNA scissions adjacent to the 8-oxoG residue in reactions where product formation was dependent on both the time of incubation with GST-dS3 (FIG. 10; lanes 2–4), and on an amount of GST-dS3 added (FIG. 10; lanes 1–3). No activity was detected on undamaged DNA. In addition, parallel purification of GST alone showed that the purified non-fusion from wild-type $E.\ coli$ lacked activity on the 8-oxoG-37 mer.

For GST-dS3, the inventors estimate that the turnover number ($k_{cat}$) for the 8-oxoG substrate to be 14 min$^{-1}$. This is in good agreement for calculations made for recombinant fusions of FPG (GST-FPG), which ranged between 10–20 min$^{-1}$ (Calculations obtained from Dr. P. Doetsch and L. Augeri, Emory University.)

Figure 11:
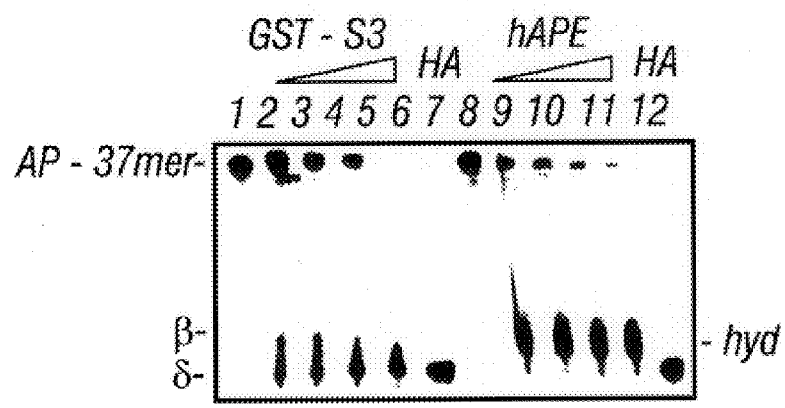
FIG. 11. Activity of GST-dS3 and APE on abasic site-containing DNA. Incubations with GST-dS3 (lanes 2–5) and hAPE (lanes 8–11) contained protein at concentrations of 10 pg (lanes 2 and 8), 25 pg (lanes 3 and 9), 50 pg (lanes 4 and 10) and 100 pg (lanes 5 and 11); Lanes 1 and 7, oligonucleotide alone; Lanes 6 and 12, hot piperidine treatment of the abasic site-containing 37 mer.

The inventors next compared the AP lyase activity of GST-dS3 with other known AP lyases or AP endonucleases from both eukaryotes and prokaryotes. These studies utilized a 5' end labeled DNA fragment containing a single abasic site, in which comparisons were originally drawn between the major AP endonuclease in humans (APE (Demple et al., 1991)) and GST-dS3. The APE enzyme is known to cleave abasic DNA by a hydrolytic mechanism, producing scissions 5' to an AP site (Kane and Linn, 1981). As can be seen in FIG. 11 (lanes 8–11), the purified human enzyme generated cleavage products with an electrophoretic mobility consistent with it acting 5' to an AP site. On the other hand, GST-dS3 produced a product with the same electrophoretic mobility as hot alkali (FIG. 11, lanes 6 and 12), which is known to generate a β,δ elimination reaction (Doetsch and Cunningham, 1990). Comparisons of GST-dS3 with GST-FPG also showed that the reaction products generated by these two proteins are similar and once again consistent with GST-dS3 catalyzing a β,δ-elimination reaction.

Figure 12:
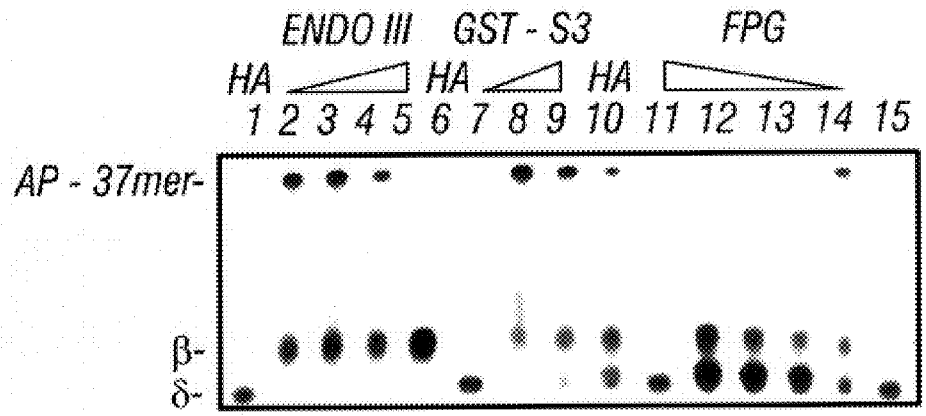
FIG. 12. Mechanism of action of GST-dS3, FPG and endo III on abasic site-containing DNA. Reactions contained 1 pmol of abasic 37 mer, and were incubated for 30 min. at 37° C. with E. coli endo III lanes 2–5) at protein concentrations of 100 pg (lane 2), 150 pg (lane 3), 200 pg (lane 4) and 400 pg (lane 5), or GST-dS3 (lanes 7–9) at 20 pg (lane 7), 40 pg (lane 8) and 80 pg (lane 9) or E. coli FPG (lanes 11–14) at 40 pg (lane 14) 80 pg (lane 13), 120 pg (lane 12) and 160 pg (lane 11); Lane 1, 6, 10 and 15, hot piperidine treatment of the abasic site-containing 37 mer.

The inventors have previously concluded that GST-dS3 processed AP sites via a β elimination reaction (Wilson et al., 1993), but the results presented in FIG. 11 suggest an additional δ elimination as well. Therefore, the inventors undertook a closer examination of the mechanism by which GST-dS3 cleaves AP sites in DNA, comparing it to a known β elimination catalyst, namely $E.\ coli$ endo III (Bailly et al., 1989). This study also included the purified $E.\ coli$ FPG protein, which has previously been shown to catalyze a concerted β,δ-elimination reaction (O'Connor and Laval, 1989). The results presented here are in agreement with previous findings, in which increasing amounts of the FPG protein (FIG. 12, lanes 11–14) resulted in virtually equal quantities of the β elimination product (slower migrating product at an electrophoretic mobility identical to that generated by $E.\ coli$ endonuclease III, lanes 2–5), and the δ elimination product (faster migrating product). In contrast, the δ elimination product generated by GST-dS3 is only revealed at higher protein concentrations (lanes 7–9), suggesting that GST-dS3 is undergoing a second encounter at an AP site to generate the δ elimination product. Thus, in this regard, S3 is clearly different that the previously characterized AP lyases residing in $E.\ coli$.

Complementation of S3 in an $E.\ coli$ MutM Strain

Figure 13:
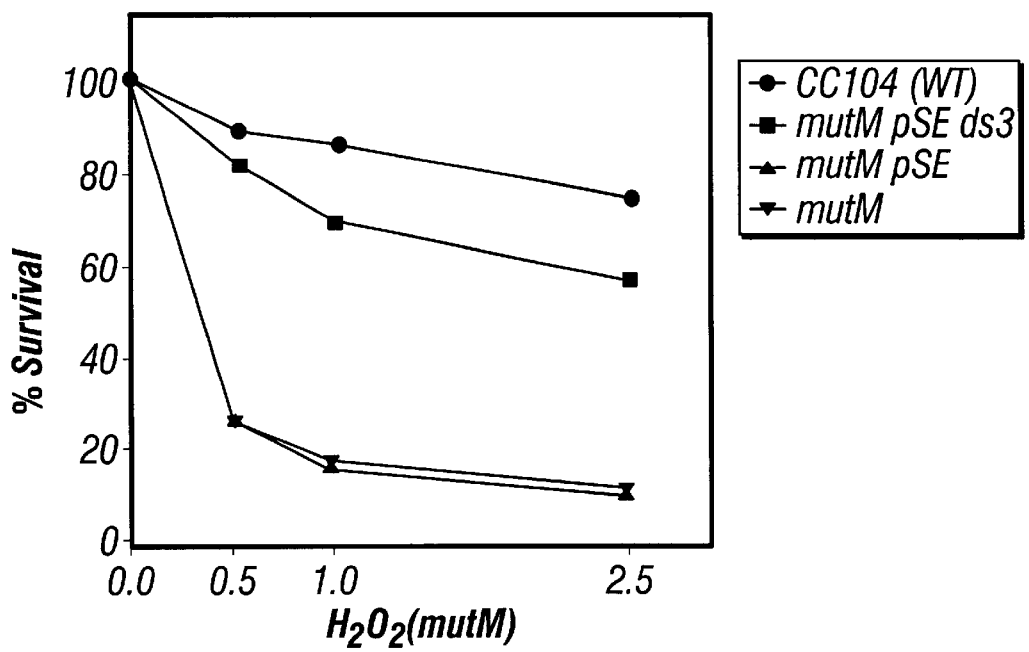
FIG. 13. Survival of mutM exposed to $H_2O_2$ in culture. The symbols are: CC104; ●-●, mutM/pSEoS3; A-A,mutM/pSE; ■-■m, mutM.

Even though the foregoing studies indicate rather robust DNA repair activities associated with the S3 ribosomal-DNA repair protein, it does not address whether these activities represent a significant source of DNA repair in vivo. Therefore, the inventors attempted to exploit the sensitivity of a MutM strain to $H_2O_2$ by complementing the defective gene encoding the FPG protein with S3 and then determine whether MutM harboring S3 remained sensitive to $H_2O_2$. As seen in FIG. 13, apSE plasmid linked to S3, but not the plasmid alone, was able to significantly increase the survival of MutM exposed to $H_2O_2$. Moreover, GST-dS3 was as efficient as $E.\ coli$ FPG in rescuing a MutM strain from sensitivity to $H_2O_2$. Survival for each of the strains containing recombinant plasmids was roughly 80% of the MutM parent CC104, whereas only about 45% of MutM survived after exposure to $H_2O_2$ Beyond its sensitivity to $H_2O_2$, MutM strains also have a high rate of formation of lac$^+$ revertants when tested against a lacZ allele that can only revert to lac$^+$ by a specific G●C to T●A transversion (Cabrera et al., 1988). Table 5 shows that the expression of ribosomal-DNA repair protein S3 reduced the number of lac$^+$ revertants in MutM to the level seen for the parent strain CC104, whereas the vector alone had no effect on the mutation rate of MutM Table 5. Complementation of a mutM strain. Log phase cultures of mutM, mutM containing the control plasmid pSE420 (Invitrogen) or pSE420-S3 and wild-type CC 104 were plated on minimal lactose media. Revertants to Lac$^+$ were counted from 15 independent cultures. The average reversion frequencies and standard deviation are expressed per 10$^8$ cells.

| Strain | Plasmid | Lac$^+$ Revertants |
|---|---|---|
| CC104 (wild-type) | — | 2 ± I |
| MutM | — | 45 ± 8 |
| MutM | pSE420 | 42 ± 8 |
| MutM | pSE420-S3 | 2 ± 1 |

Figure 14:
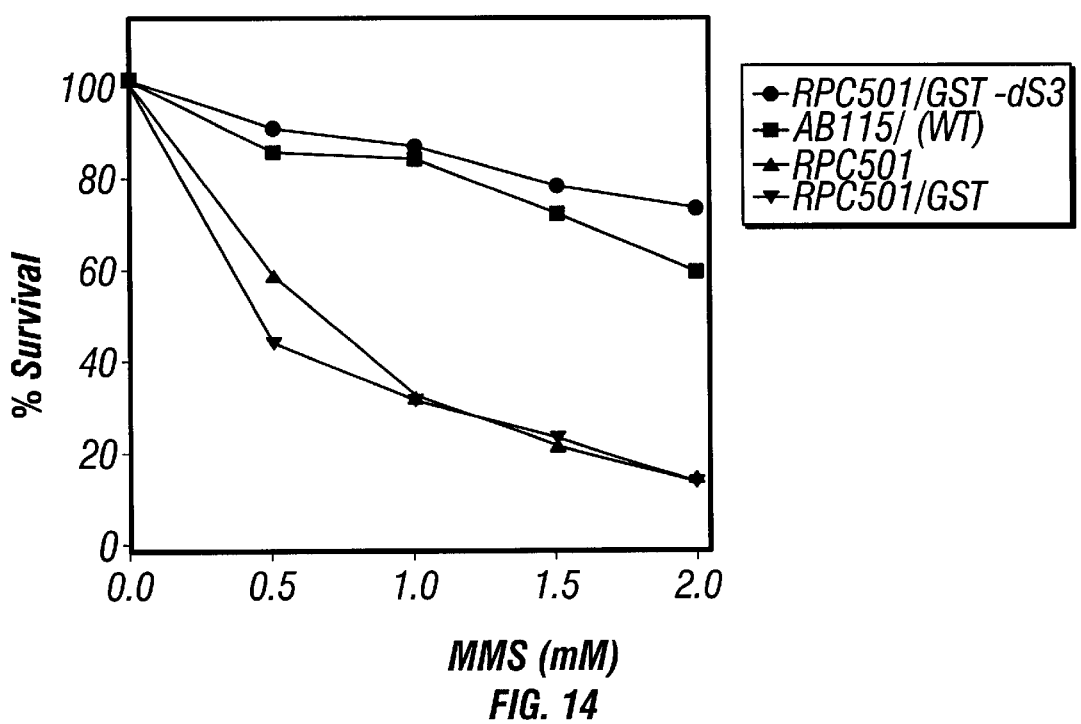
FIG. 14. Survival of RPC501 (xth, nfo) exposed to MMS in culture.

Some controversy exists as to whether AP lyases represent significant DNA repair activities distinct from their N-glycosylase activities in vivo. It was therefore of some interest to determine if the very active AP lyase activity associated with S3 could protect $E\ coli$ mutants, deficient for the majority of AP endonuclease activity present in this organism, from the harmful consequences of a mutagen known to generate AP sites in DNA, namely methyl methanesulfonate (MMS). The bacterial mutant strain chosen for transformation with either GST-dS3 or GST was RPC501 (Cunningham et al., 1986), which is deficient for the AP endonuclease activities associated with exonuclease III (xth), and endonuclease IV (nfo). Notably GST-dS3, but not GST, was able to fully complement the sensitivity of RPC501 to MMS at low concentrations of mutagen (FIG. 14). As concentrations of MMS increased beyond 2 mM, the ability of GST-dS3 to complement RPC501 was not as efficient, but nevertheless still afforded some protection to RPC501 even at concentrations exceeding 5 mM MMS. These results are not unlike those seen with the complementation of FA(A) with dS3 (see FIG. 15)

Figure 15:
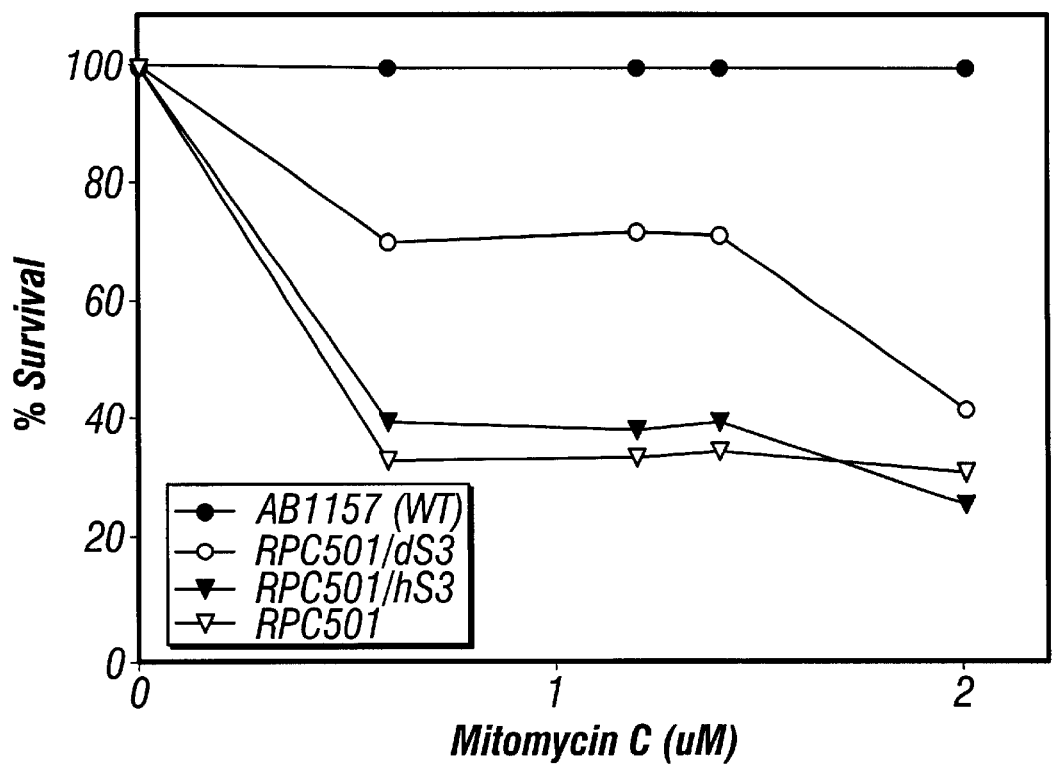
FIG. 15. Complementation of E.coli RPC501 cells with the Drosophila and human S3 genes against MMC.
Figure 16:
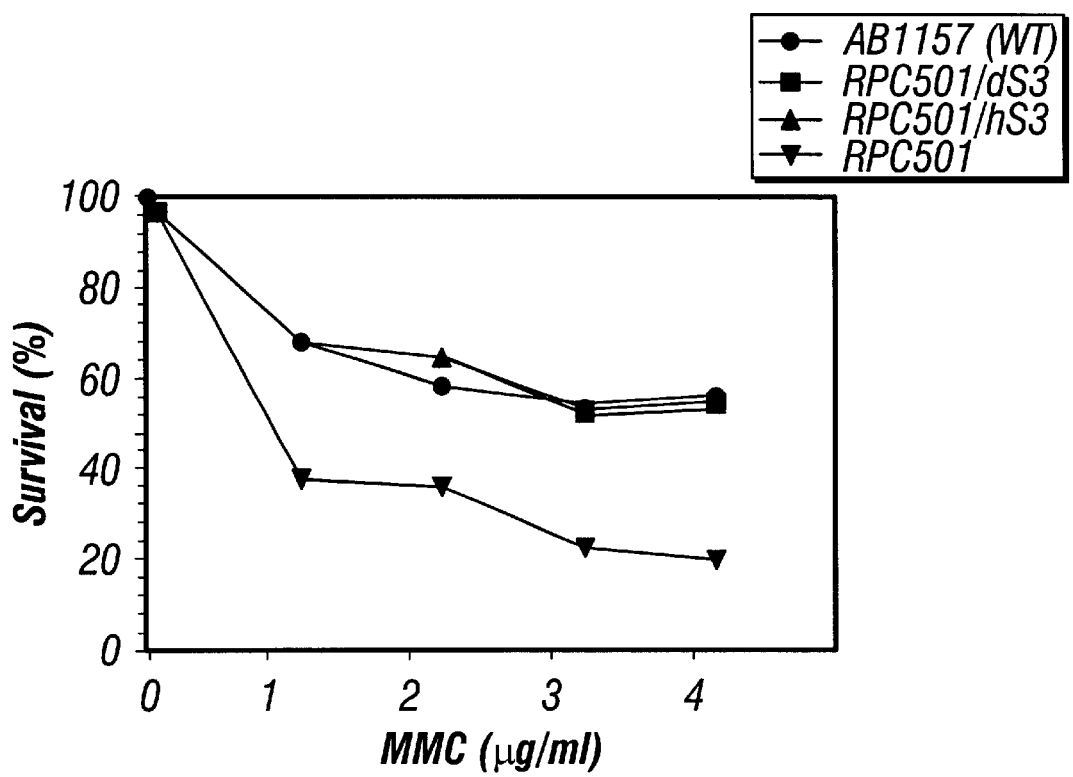
FIG. 16. Protection of E. coli fpg or the dS3 gene against MMC toxicity in the E.coli mutM strain.

Using RPC501 cells that have either the Drosophila or human S3 (hS3) gene in an expression vector (pGEX), the inventors can determine whether a primary component of MMC activity is via oxidative DNA damage or cross-linking. Since the RPCS01 cells are only deficient for AP endonuclease activity, if they are sensitive to MMC, this must be through the lack of repair of an oxidative DNA adduct. Using gradient plate assays, the inventors have determined that RPC501 cells are, in fact, very sensitive to MMC (FIG. 15) and can be rescued only by the dS3 gene, but not the hS3 gene (FIG. 15). Therefore, a component of MMC cell toxicity can be attributed to oxidative DNA damage and confirms the results the inventors have observed in FA(A) cells, whereby the dS3 gene can rescue these cells from MMC (see below). This does not imply that MMC does not cause cross-links in DNA, but does support the notion that a significant component of MMC cell toxicity results from it acting as an oxidative DNA damaging agent. Furthermore, these results show a difference in the activity of the Drosophila and human S3 genes on MMC induced damage. Further investigation into the specificities of the Drosophila and human S3 recognition of DNA damage is warranted. In preliminary studies (FIG. 16), the S3 gene level of protection dropped at the high dose of 200 nM MMC. This could be due to an increase in the number of cross-links or the number of 8-oxoG/fapg adducts being higher than the amount of S3 in these cells available for repair.

Finally, in order to demonstrate that the oxidative DNA damaging effect of MMC is through the formation of 8oxoG or FaPy residues, the inventors transformed the fpg deficient strain of *E.coli*(MutM) with either the dS3 or E. gene in the pGEX expression vector. Survival studies were performed as previously described and the results shown in FIG. 16. As can be seen, both the *E. coli* fpg and the dS3 genes can completely rescue the MutM from the toxicity of MMC. As it has not been shown that either FPG or dS3 can repair or act on cross-linked DNA, and since the only defect of DNA repair in this strain is the fpg gene, the inventors conclude that a significant component of MMC's ability to kill cells is due to oxidative DNA damage that can be repaired by either the fpg or dS3 genes.

Complementation of FA(A) Cells with S3

Figure 17:
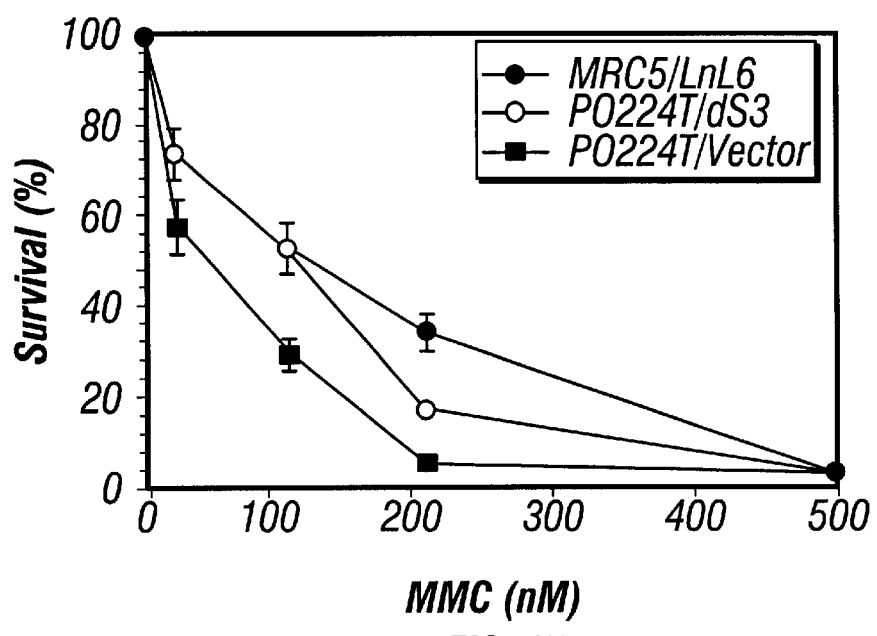
FIG. 17. Complementation of FA(A) cell line PD224. T with the Drosophila S3 gene. MRC5/LnL6 is the control transfected normal cell line, while PD224. T/dS3 is the Drosophila S3 transfected FA(A) cell line.

The FA(A) cell line PD224.T was transduced with either a retrovirus containing the dS3 cDNA (PD224.T/DS3) or a control virus (PD224.T/LnL6) containing only the neo gene. To serve as a control, MRC5 normal human lymphoblast cells were transduced with LnL6 (MRCS/LnL6). Results of three independent studies are shown (FIG. 17). Cells were treated with either 0, 20, 100, 200 or 500 nM MMC for 24 h, then cells were plated onto 10 cm dishes in triplicate at 800 cells per plate. Individual surviving cell colonies were scored after 10 d. Survival percent is the ratio of the number of colonies scored in MMC to the number of colonies without MMC. At the 20 and 100 nM level of MMC, the dS3 gene provided protection equivalent to LNL6 control survival level. These results are comparable to that seen with the dS3 and *E.coli* fpg genes rescuing a MutM strain from sensitivity to $H_2O_2$. As shown in FIG. 13, the *E.coli* complementation level for $H_2O_2$ was 80% of wild-type.

Figure 18:
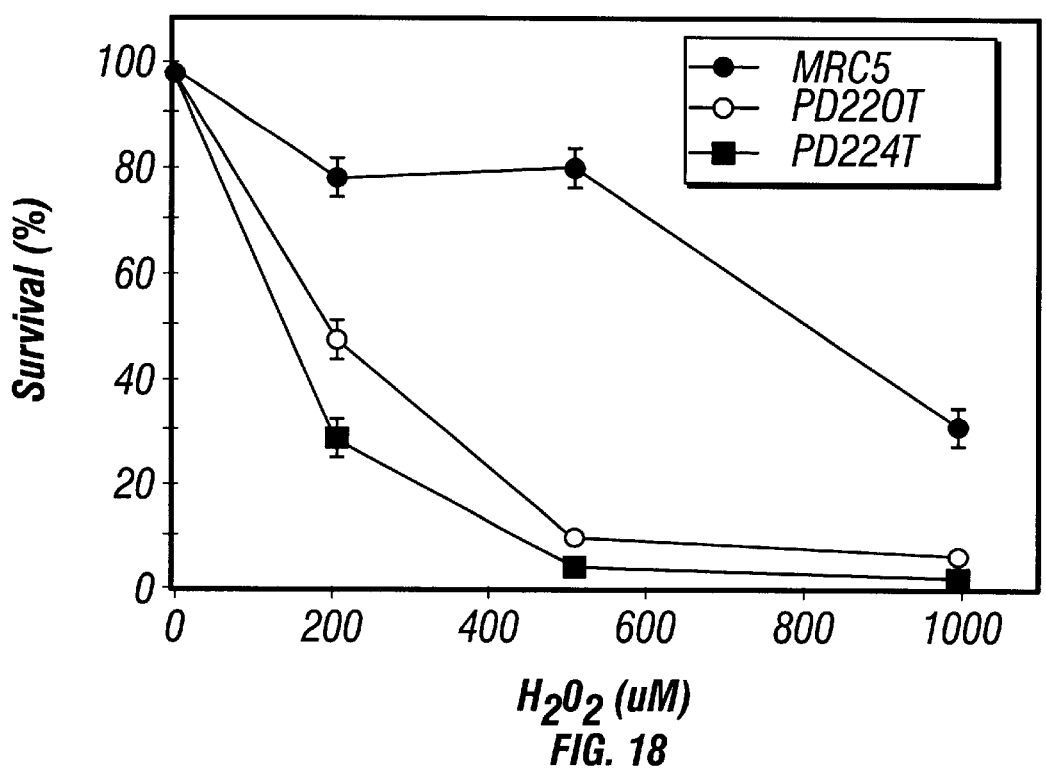
FIG. 18. Sensitivity of FA(A) cells to $H_2O_2$. MRC5 are control cells, PD220T and PD224 T are two FA(A) cell lines.

Since it appears FA(A) cells are sensitive to MMC, not only due to cross-links in the DNA produced by this drug, but also due to oxidative DNA damage, then the inventors hypothesized that FA(A) cells should also be sensitive to $H_2O_2$. Previous studies have also shown a sensitivity of FA cells to $H_2O_2$ (Kupfer and D'Andrea, 1996). The inventors tested the survival of two different FA(A) cell lines, PD224.T and PD220.T following exposure to $H_2O_2$. As shown in FIG. 18, both of the FA(A) cell lines were sensitive to $H_2O_2$ when compared to the control MRC5 cell line. As proposed, the inventors will use retroviral constructs with the dS3, hS3, *E.coli* fpg and endo III genes and the yeast OGG1 gene to see if these other DNA repair genes can also protect FA(A) and the other FA groups against the oxidative DNA damage.

Figure 19:
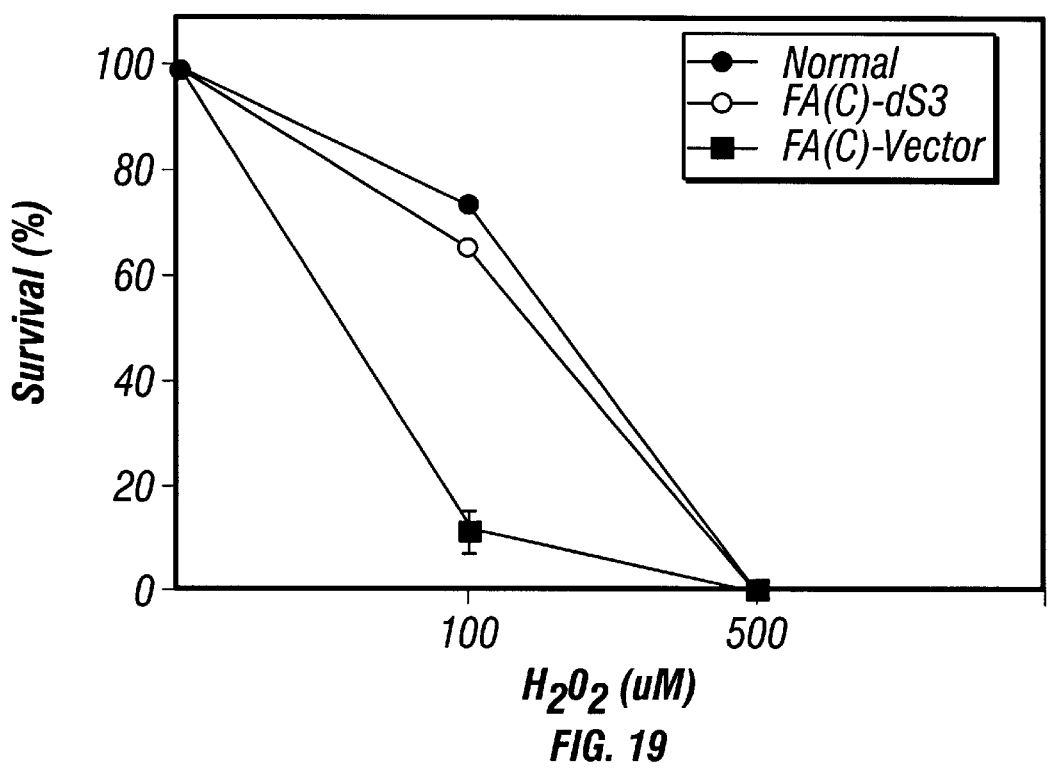
FIG. 19. Protection of FA(C) cells against the oxidative DNA damaging agent $H_2O_2$. Normal (KP BLCL), HSC536 control cells infected with vector alone and HSC536 cells infected with dS3 were exposed to doses of $H_2O_2$ and cell survival determined as previously described.

Further confirmation of the oxidative DNA damage sensitivity of FA cell types is shown in studies with a FA(C) cell line, HSC536. As shown in FIG. 19, FA(C) cells are very sensitive to oxidative DNA damage caused via $H_2O_2$. However, almost complete protection of FA(C) occurs when the dS3 retroviral construct is introduced into these cells. These results are extremely exciting as they support the hypothesis that; 1) more than just the FA(A) cells are sensitive to oxidative DNA damaging agents, i e., this phenotype is a general FA phenomena not restricted to just the FA(A) type, but also, at least, the FA(C) type, and 2) dS3 protects the other complementation types, besides FA(A), against oxidative DNA damage. These results provide evidence that the protection of FA cells against oxidative DNA damaging agents can be accomplished using oxidative DNA damage DNA repair genes and may afford the opportunity to use these genes in a global fashion irrespective of the FA complementation type.

Figure 20A:
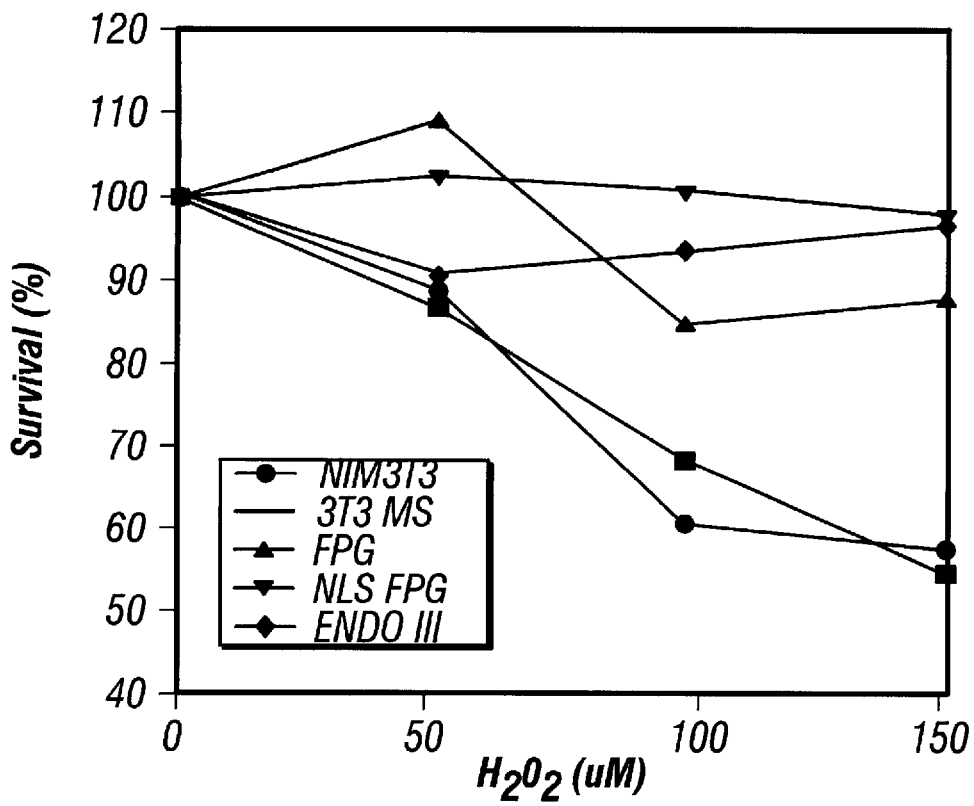
FIG. 20A and FIG. 20B. Protection of NIH3T3 cells.

Since the dS3 gene has functions similar to the *E.coli* fpg gene, and the data presented herein supports the hypothesis that FA is an oxidative DNA damage disease, the inventors have performed studies using the *E.coli* fpg and endo III genes to protect cells against oxidative DNA damaging agents. For studies, the inventors have used NIH3T3 cells and $H_2O_2$ treatments. As can be seen in FIG. 20A, both fpg and endoIII protect the NIH3T3 cells when compared to NIH3T3 cells alone and NIH3T3 cells infected with the empty vector (MSCV/3T3) (FIG. 20A). These results suggest that these *E.coli* genes may be useful in protecting FA cells against oxidative DNA damaging agents. In addition, the inventors have added a nuclear localization signal (NLS) to the FPG protein (FPG-NLS) in an attempt to improve the nuclear concentration of the repair protein.

Figure 20B:
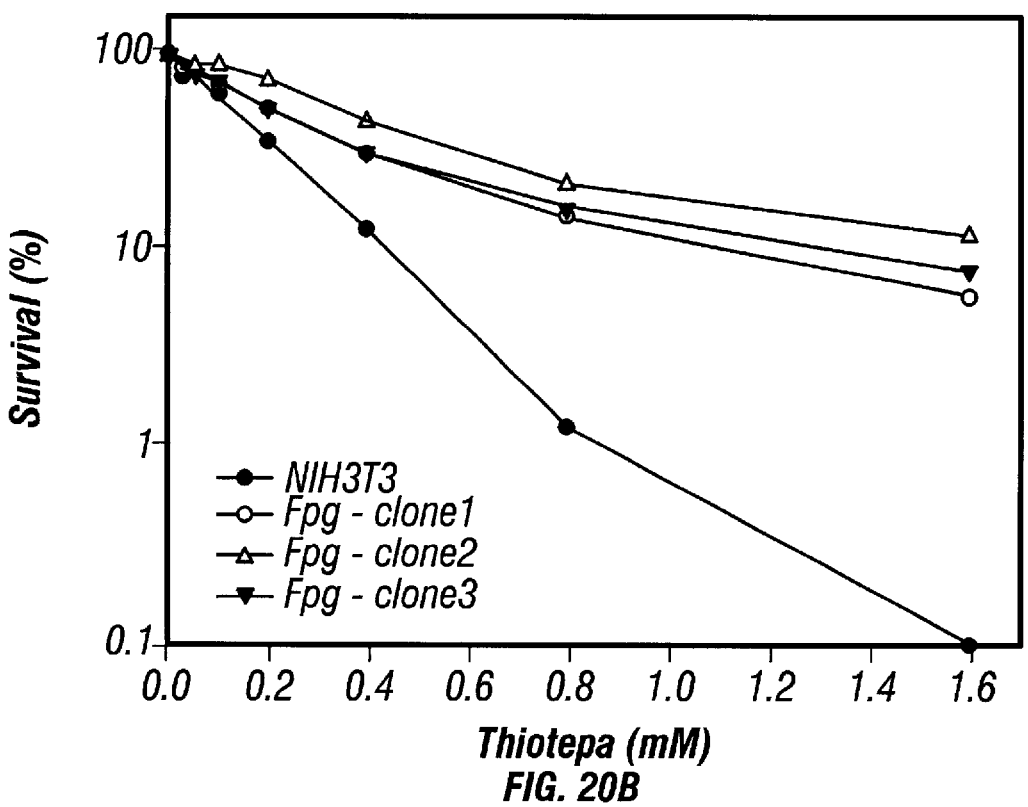

The inventors found that the fpg gene also protects against the cytotoxic effects of thiotepa when expressed in the NIH3T3 cells (FIG. 20B). NIH3T3 cells were infected with either the MSCV-fpg virus or an empty neo virus as a control. Several fpg-expressing positive clones were chosen for the study demonstrating protection against thiotepa, an alkylating chemotherapeutic agent. Over two orders of magnitude of protection are observed for the cells with the fpg gene versus cells with retroviral vector alone.

Thus, from these data, it appears that the FPG construct containing the NLS is superior to FPG alone. Furthermore, these studies suggest that it is possible to equal or increase the protective ability using the FPG protein with an added NLS even though the clone used in these studies expressed FPG mRNA at a 10-fold lower level. This implies that a lower expression level may still afford significant protection when the produced protein is targeted to the nucleus, its site of action, via a NLS.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

References

The following references, to the extent that they provide exemplary procedural or other details supplementary to those set forth herein, are specifically incorporated herein by reference.

Allay et al., *Blood*, 95:3342, 1995.
Ames et al., *Science*, 221(4617):1256–1264, 1983.
Anderson and Friedberg, *Nucleic Acids Res.*, 8(4):875–88, 1980.
Antman et al., *J. Clin. Oncol.*, 10:102, 1992.
Armel and Wallace, *Nucleic Acids Res*, 5(9):3347–56,1978
Armel and Wallace, *J. Bacteriol.*, 160(3):895–902, 1984.
Baichwal and Sugden, In: *Gene Transfer*, Kucherlapati R, ed., New York, Plenum Press, pp. 117–148, 1986.
Bailly et al., *J. Biochemical J.* 262:581–589, 1989.
Barnes et al., *Cell*, 69(3):495–503, 1992.
Barrows and Magee, *Carcinogenesis*, 3(3):p349–51, 1982.
Barzilay et al., *Nat. Struct. Biol.*, 2 (7) p561–8, 1995
Barzilay et al., *Nucleic Acids Res.*, 23 (9) p1544–50, 1995
Benvenisty and Neshif, *Proc. Nat. Acad. Sci. USA*, 83:9551–9555, 1986.
Bjelland et al., *J. Biol. Chem.*, 269:30489–30495.
Bohr et al., *Lab. Invest.*, 61(2):143–61, 1989.
Boiteux and Laval, *Biochem. Biophys. Res. Commun.*, 110 (2):552–558, 1983.
Boiteux, et al., *J. Biol. Chem.*, 265(7)3916–3922, 1990.
Boiteux et al., *Nucl. Acids Res.*, 16:6779, 1988.
Bonura et al., *Biochemistry*, 21(10):2548–56, 1982.
Bootsma and Hoeijmakers, *Ann Genet*, 34(3–4):143–50, 1991.
Brash, *Photochem. Photobiol.*, 48(1):59–66, 1988.
Brent and Remack, *Nucl. Acid Res.*, 16:6779, 1988.
Brent et al., *Biochem.*, 85:1759, 1988.
Brinster et al., *Proc. Nat'l Acad. Sci. USA*, 82: 4438–4442, 1985.
Broun et al., *Annals Intern. Med.*, 117:124, 1992.
Bucala et al., *Proc. Natl. Acad. Sci. USA*, 81(1):105–9, 1984.
Cabrera et al., *J. Bacteriology*, 170:5405–5407, 1988.
Capaldi et al., *Biochem. Biophys. Res. Comm.*, 76:425, 1977
Carter et al., *Adv. Cancer Res.* 16:273–332, 1992.
Cesar and Verly, *J. Biochem*, 129(3):509–517, 1983.
Chan and Weiss, *Proc Nat'l. Acad. Sci. USA*, 84(10):3189–3193, 1987.
Chang, et al., *J. Bacteriol.*, 169(1):180–3, 1987.
Chang et al., *Hepatology*, 14:124A, 1991.
Chen and Okayama, *Mol. Cell Biol.*, 7:2745–2752, 1987.
Chen et al., *Nucleic Acids Res*, 19(21):5907–5914, 1991.
Cheng et al., *Nucl. Acid. Res.*, 20:370, 1992a
Cheng et al., *Nucl. Acid. Res.*, 20:370, 1992b.
Cheung and Heller, *J. Clin. Oncol.*, 9:1050, 1991.
Clarke et al., *Mol Gen. Genet*, 197(3):368–372, 1984.
Cleaver, *Carcinogenesis*, 11(6):p875–82, 1990.
Coffin, In: Fields B N, Knipe D M, ed. Virology. New York: Raven Press, pp. 1437–1500, 1990.
Corey, et al., *Blood*, 75:337, 1990.
Cornetta, *Br. J. Hematol.*, 80:421, 1992.
Couch et al., *Am. Rev. Resp. Dis.*, 88:394–403, 1963.
Coupar et al., *Gene*, 68:1–10, 1988.
Crone, et al., *Cancer Res.*, 54:6221–6227, 1994.
Culver et al., *Science*, 256:1550–1552, 1992.
Cunningham, et al., *J. of Bact.* 168:1120–1127, 1986.
Cunningham, et al., *Bacteriol.*, 168:1120–1127, 1986.
Davies Biochem. Soc. Symp., 61 p1–31, 1995
Del Rosso, et al., *Biochim. Biophys. Acta*, 676:129, 1981.
Demple and Halbrook, *J Nature*, 304 5925:466–468,1983.
Demple and Harrison, *Ann. Rev. Biochem.*, 63:915, 1994.
Demple and Linn, *Nucleic Acids Res*, 10(12):3781–9, 1982.
Demple et al., *J Bacteriol.* 153, 1079–1082, 1983.
Demple et al., *Proc. Natl. Acad. Sci. USA*, 83:7731–7735, 1986.
Demple et al., *Proc. Natl. Acad. Sci. USA*, 88:11450–11454, 1991.
Dianov and Lindahl, *Curr. Biol.*, 4(12):1069–76, 1994.
Doetsch and Cunningham, *Mutat. Res.*, 236:173, 1990.
Doetsch et al., *Biochemistry*, 34:737–742, 1995.
Doetsch, et al., *Mutat. Res.*, 236:173–201, 1990.
Dolan et al., *Proc. Natl. Acad. Sci. USA*, 87:5368, 1990.
Domena and Mosbaugh, *Biochemistry*, 24(25):7320–8, 1985.
Domena et al., *Biochemistry*, 27(18):6742–51, 1988.
Dubensky et al., *Proc. Nat. Acad. Sci. USA*, 81:7529–7533, 1984.
Duncan and Weiss, *J. Bacteriol.*, 151:750–755, 1982.
Erickson et al., *Nature*, 288:727, 1980.
Evensen and Seeberg et al., *Nature*, 296(5859):773–5, 1982.
Fechheimer et al., *Proc. Natl. Acad. Sci. USA*, 84:8463–8467, 1987.
Feig and Loeb, *Biochemistry*, 32(16):4466–73, 1993.
Ferkol et al., *FASEB J.*, 7:1081–1091, 1993.
Fischer et al, *Lipids*, 23(6):592–7, 1988.
Fraley et al., *Proc. Natl. Acad. Sci. USA*, 76:3348–3352, 1979.
Freshner, Second Edition, Oxford/New York, IRL Press, Oxford University Press, 1992.
Friedberg and Goldthwait, *Proc. Natl. Acad. Sci. USA*, 62(3):934–40, 1969.
Friedberg, W. H. Freeman, NY, 1985.
Friedberg et al., *DNA Repair and Mutagenesis*, Washington, D.C., ASM Press, 1995.
Friedmann, *Science*, 244:1275–1281, 1989.
Gajewski et al., *Biochemistry*, 29: 7876–82, 1990.
Gates and Linn, *J Biol. Chem.*, 252(9):2802–7, 1977.
Gensler and Bernstein, *The Quarterly Review of Biology*, 56:279, 1981.
Gerson et al., *Carcinogenesis* 7:745–749, 1986.
Gerson et al., *J. Clin. Invest.*, 76:2106, 1985.
Ghosh-Choudhury et al., *EMBO J.*, 6:1733–1739, 1987.
Ghosh and Bachhawat, "In: Liver diseases, targeted diagnosis and therapy using specific receptors and ligands, Wu G, Wu C ed., New York: Marcel Dekker, pp. 87–104, 1991.
Gill et al., *Cancer Res.* 56:3721–3724, 1996.
Giloni et al., *J. Biol. Chem.*, 256(16) p8608–15, 1981.
Gomez-Foix et al.,*J. Biol. Chem.*, 267:25129–25134, 1992.
Gopal, *Mol. Cell Biol.*, 5:1188–1190, 1985.
Gossard and Verly, *Eur. J. Biochem.*, 82(2):p321–32, 1978.
Graham and Prevec, *Biotechnology*, 20:363–390, 1992.
Graham and Prevec, In: *Methods in Molecular Biology: Gene Transfer and Expression Protocol*, Clifton, E. J. Murray (ed.), N J: Humana Press, 7:109–128, 1991.
Graham and Van Der Eb, *Virology*, 52:456467, 1973.
Graham et al., *J. Gen. Virol.*, 36:59–72, 1977.
Greenbaum, et al., *Cancer Res.*, 54:4442, 1994.
Gribskov and Burgess, *Nuc. Acids Res.*, 14:6745, 1986.
Grunhaus and Horwitz, *Seminar in Virology*, 3:237–252, 1992.
Halliwell and Aruoma, *FEBS Lett.*, 281(1–2):9–19, 1991.
Halliwell and Gutteridge et al., *Methods Enzymol*, 186:1–85, 1990.
Hanania and Deisseroth, *Canc. Gene Ther.*, 1:21, 1994.
Hanenberg, et al., *Nature Medicine*, 2:876, 1996.
Harland and Weintraub,*J. Cell Biol.*, 101:1094–1099, 1985.
Harosh and Sperling, *J. Biol. Chem.*, 263(7)3328–34, 1988.
Harrison et al., *Hum Mol Genet.*, 1(9):p677, 1992.
Harrison et al., *Radiat. Res.*, 132(1):30–39, 1992.

Haseltine, *Cell,* 33(1) p13–7, 1983.
Haukanes et al., *Nucleic Acids Res.,* 17(4):1493–1509, 1989.
Haukanes et al., *Nucleic Acids Res.,* 17(4):1493–1509, 1989a.
Haukanes et al., *Nucleic Acids Res.,* 17(14):5529–5535, 1989b.
Hayatsu, *Prog. Nucl. Adds Res. Mol. Biol.,* 16:75–124, 1976.
Henner et al., *J. Biol. Chem.,* 258 (24):15198–205, 1983.
Henner et al., *Nucleic Acids Res,* 5(14):5529–5544, 1987.
Hermonat and Muzycska, *Proc. Nat. Acad. Sci. USA,* 81:6466–6470, 1984.
Hersdorffer et al., *DNA Cell Biol.,* 9:713–723, 1990.
Herz and Gerard, *Proc. Natl. Acad. Sci. USA* 90:2812–2816, 1993.
Ho et al., *Gene,* 77:51, 1989.
Hoeijmakers and Bootsma, *Nat Genet,* 1(5):313–4, 1992.
Hogan et al., *Manipulating the Mouse Embryo: A Laboratory Manual,* Cold Spring Harbor Laboratory, 1986.
Horton et al., *Nucl. Acids Res.,* 23:3810, 1995.
Horton et al., *Nucleic Acids Research,* 23:3810, 1995.
Horwich et al., *J Virol.,* 64:642–650, 1990.
Hutchinson et al., *J. Virol,* 53 (3) p814–21, 1985
Hutchinson, *Prog. Nucl. Acid. Res. Mol. Biol.,* 32:115–154, 1985.
Ibeanu et al., *Carcinogenesis,* 13:1989, 1992.
Imlay and Linn, "DNA damage and oxygen radical toxicity," *Science,* 240:1302–1309, 1988.
Ivanov et al., *Eur. J. Biochem.,* 172(1):155–9, 1988.
Jelinek et al., *Blood,* 87:1957, 1996.
Johnson and Demple, *J. Biol. Chem.,* 263(34):18017–18022, 1988.
Johnson and Demple, *J. Biol. Chem.,* 263:18009–18016, 1988a.
Johnson and Demple, *J. Biol. Chem.,* 263:18017–18022, 1988b.
Johnson et al., Peptide Turn Mimetics" IN: *Biotechnology And Pharmacy*, Pezzuto et al., eds., Chapman and Hall, New York, 1993.
Jones and Shenk, *Cell,* 13:181–188, 1978.
Kaina et al., *Envir. and Mol. Mutag.,* 22:283, 1993.
Kamel-Reid and Dick, *Science,* 242:1706, 1988.
Kane and Linn, *J. Biol. Chem.,* 256:3405–3414, 1981.
Kaneda et al., *Science,* 243:375–378, 1989.
Karlsson et al., *EMBO J.,* 5:2377–2385, 1986.
Karran and Lindahl, *Biochemistry,* 19(26):6005–11, 1980.
Karran et al., *Nature,* 296(5859):770–773, 1982.
Kastan et al., *Cell,* 71(4):587–97, 1992.
Kato et al., *J. Biol. Chem.,* 266:3361–3364, 1991.
Kirtikar et al., *Biochemistry,* 14(26):5548–53, 1975a
Kirtikar et al., *Biochemistry,* 14(26):5548–53, 1975b
Kirtikar et al., *Biochemistry,* 14(26):5548–53, 1975c
Kirtikar et al., *Biochemistry,* 14(26):5548–53, 1975d
Klein et al., *Nature,* 327:70–73, 1987.
Kow and Wallace, *Biochemistry,* 26(25):8200–6, 1987.
Kow and Wallace, *Proc. Natl. Acad Sci. USA,* 82:8354–8358, 1985.
Kow, *Biochemistry,* 28(8):3280–3287, 1989.
Krokan and Wittwer, *Nucleic Acids Res,* 9(11):2599–613, 1981.
Kupfer and D'Andrea, *Blood,* 88(3):p1019–25, 1996.
Kyte and Doolittle, *J. Mol. Biol.,* 157(1):105–132, 1982.
Lamar and Palmer, *Cell,* 37:181, 1984.
Larochelle et al., *Nat. Med.,* 2 (12) p1329–37, 1996.
Larochelle et al., Submitted, 1996.
Larson et al., *Mutat. Res.,* 236:77, 1985.
Le Gal La Salle et al., *Science,* 259:988–990, 1993.
Lee and Cerami, *Proc. Natl. Acad Sci. USA,* 84:(23) p8311–4, 1987.
Levin et al., *J. Biol. Chem.,* 263:8066–8071, 1988.
Levrero et al., *Gene,* 101:195–202, 1991.
Li et al., *Blood,* 83:3403, 1994.
Lindahl and Nyberg, *Biochem.,* 11:3610–3618, 1972.
Lindahl et al., *Ann. Rev. Biochem.,* 57:133, 1988.
Lindahl, *Proc. Natl. Acad. Sci. USA,* 71:3549–3653, 1974.
Ljungquist, *Virology,* 73:(2)402–12, 1976.
Loeb and Preston, *Ann. Rev. Genet.,* 20:201, 1986.
Lorenzi et al., *J. Clin Invest.,* 77(1):322–5, 1986.
Loveless, *Nature,* 223(202):206–207, 1969.
Lowenhaupt et al., *J. Biol. Chem.,* 264(34):20568–75, 1989.
Ludlum, *Mutation Res.,* 233:117, 1980.
Macejak and Sarnow, *Nature,* 353:90–94, 1991.
Magni et al., *Blood,* 87:1097, 1996.
"Manipulating the Mouse Embryo: A Laboratory Manual," $2^{nd}$ ed., Hogan et al., eds., Cold Spring Harbor Laboratory Press, 1994.
Mann et al., *Cell,* 33:153–159, 1983.
Markesberry, *Free Radic. Biol. Med.,* 23(1):134–147, 1997.
Markowitz et al., *J. Virol.,* 62:1120–1124, 1988.
Markowitz et al., *J. Virol.,* 62:1120–1124, 1988a.
Markowitz et al., *Virology,* 167:400–406, 1988b.
Marshall, *Science,* 269:1050, 1995.
Maze et al., *Cancer Res.,* 54:4947, 1994.
Maze et al., *Proc. Nat'l. Acad. Sci. USA,* 93:206, 1996.
Miller et al., *Science,* 225:993, 1984.
Miller, *Nature,* 357:455, 1992.
Mitra et al., *Lab Invest,* 76(1):99–107, 1997.
*Mol. Microbiol.* (ENGLAND), January 1991, 5 (1) p149–55, ISSN 0950–382X.
Morgan, et al., Bio. and Molecular Bio., Inc. p. 19802, 1993.
Moritz and Williams, In: *Encyclopedia of Cancer* Bertino, ed., San Diego, Academic Press, 1996.
Moritz and Williams, In: *Scientific basis of transfusion medicine*. Anderson, ed., Philadelphis, Churchill Linvingstone, p. 180, 1994.
Moritz et al., *Cancer Res.,* 55:2608, 1995.
Moritz et al., *Blood,* 82:118a, 1993.
Moritz et al., *J. Clin. Invest.,* 93:1451, 1994.
Moritzetal., *Blood,* 88:855, 1996.
Muller and Caradonna, *Biochim Biophys Acta,* 1088(2):197–207,1991.
Mulligan, *Science,* 260:926, 1993.
Myers, EP 0273085
Myrnes et al., *J. Cell Biochem.,* 20(4):381–92, 1982.
Nakabeppu et al., *J. Biol. Chem.,* 259(22):13730–13736, 1984a.
Needleman and Wunsch, *J. Mol. Biol.,* 48:443, 1970.
Nicolas and Rubenstein, In: *Vectors: A survey of molecular cloning vectors and their uses*, Rodriquez and Denhardt (eds.), Stoneham: Butterworth, pp. 493–513, 1988.
Nicolau and Sene, *Biochim. Biophys. Acta,* 721:185–190, 1982.
Nicolau et al., *Methods Enzymol.,* 149:157–176, 1987.
O'Connor and Laval, *Proc. Natl. Acad. Sci. USA.,* 86:5222–5226, 1989.
Olsen et al., *EMBO J.,* 8(10):3121–5, 1989.
Ono, et al., *Devel. Brain Res.,* 86:1, 1995.
Owen et al., *Ann. NY Acad. Sci.,* 786 p217–23, 1996.
Paskind et al., *Virology,* 67:242–248, 1975.
Pegg, *Cancer Res.,* 50:6119, 1990.
Pegg, et al., *Progress in Nucleic Acid Research and Molecular Biology* 51:167, 1995.
Pelletier and Sonenberg, *Nature,* 334:320–325, 1988.
Perales et al., *Proc. Natl. Acad. Sci.* 91:40864090, 1994.
Petrini et al., *Proc. Natl. Acad. Sci.,* 88 (17) p7615–9, 1991.

Popoff, et al., *Proc. Natl. Acad. Sci USA,* 87:4193–4197, 1990.
Potter et al., *Proc. Nat. Acad. Sci. USA,* 81:7161–7165, 1984.
Povirk and Houlgrave, *Biochem.,* 27:3850–3857, 1988.
Racher et al., *Biotechnology Techniques,* 9:169–174, 1995.
Ragot et al., *Nature,* 361:647–650, 1993.
Ramotar, et al., *Mol. Cell Biol.,* 11(9):4537–44, 1991.
Renan, *Radiother. Oncol.,* 19:197–218, 1990.
Rich et al., *Hum. Gene Ther.,* 4:461–476, 1993.
Ridgeway, In: Vectors: A survey of molecular cloning vectors and their uses, Rodriguez R L, Denhardt D T, ed., Stoneham: Butterworth, pp. 467–492, 1988.
Rippe et al., *Mol. Cell Biol.,* 10:689–695, 1990.
Robins, et al., *Nucl. Acids Res.,* 11:7743, 1983.
Robson and Hickson, *Nucl. Acids Res.,* 19:5519–5523, 1991.
Robson, et al., *Nucl. Acids. Res.,* 19:1087–1092, 1991.
Robson, et al., *Nucleic Acids Res,* 20(17):4417–4421, 1992.
Rogers and Weiss, *Methods Enzymol.,* 65(1):201–11, 1980.
Rosenfeld et al., *Cell,* 68:143–155, 1992.
Rosenfeld et al., *Science,* 252:431–434, 1991.
Roux et al., *Proc. Nat'l Acad. Sci. USA,* 86:9079–9083, 1989.
Russell and Miller, *J. Virology,* 70:217, 1996.
Saffhill et al., *Biochim. Biophys. Acta,* 823:111, 1985.
Sakumi and Sekiguchi, *Mutat Res,* 236(2–3):161–72, 1990.
Samson, et al., *Proc. Nat'l. Acad. Sci. USA,* 83:5607, 1986.
Sancar and Sancar, *Ann. Rev. Biochem.,* 57:29, 1988.
Sander, *Pediatr. Pathol.,* 13 (5):621–33, 1993.
Sander et al., *Proc. Natl. Acad. Sci. USA,* 88:6780–6784, 1991a.
Sander et al., *Nucleic Acids Res* 19(16):p4523–9, 1991b.
Saporito and Cunningham, *J. Bacteriol.,* 170:5141–5145, 1988.
Saporito et al., *J. Bacteriol.,* 170:393–383, 1988.
Saul and Bonifaz, *Rev Infect Dis,* 9(1):S100–3, 1987.
Schuster, *Biochem. Biophys. Res. Comm.,* 2:320–323, 1960.
Schwartz and Dayhoff, eds., *Atlas of Protein Sequence and Structure,* National Biomedical Research Foundation, pp. 353–358, 1979.
Schwenn et al., *J. Clin. Oncol.,* 9:133, 1991.
Seal et al., *Biochim. Biophys. Acta,* 1097(4):299–308, 1991b.
Seki, et al., *Biochem. Biophys. Acta* 1079:57–64, 1991.
Seki et al., *J. Biol. Chem.,* 266:20797–20802, 1991a.
Setlow, *Prog Nucleic Acid Res Mol Biol,* 8:257–295, 1968.
Shaper et al., *J. Biol. Chem,* 257(22):13455–8, 1982.
Simonian and Coyle, *Annu. Rev. Pharmacol. Toxicol,* 36 p83–106, 1996.
Smith and Waterman, *Adv. Appl. Math.* 2:482, 1981.
Smith et al., *J. Nat'l. Cancer Inst.,* 83:1460, 1991.
Spiering and Deutsch, *J. Biol. Chem.,* 261:3222–3228, 1986.
Spiering and Deutsch, *Mol. Gen. Genet.* 183, 171–174, 1981.
Srour, et al., *Blood,* 82:3333, 1993.
Steenken, *Free Rad. Res. Comm.,* 6:117–20, 1989.
Stratford-Perricaudet and Perricaudet *In: Human Gene Transfer,* Cohen-Haguenauer and Boiron (eds.), Editions John Libbey Eurotext, France, p. 51–61, 1991.
Stratford-Perricaudet et al., *Hum. Gene. Ther.,* 1:241–256, 1990.
Strathdee et al., *Nature,* 358(6385):434, 1992.
Temin, *In: Gene Transfer,* Kucherlapati (ed.), New York: Plenum Press, pp. 149–188, 1986.
Teoule, *Int. J. Radiat. Biol. Relat. Stud. Phys. Chem. Med,* 51 (4) p573–89, 1987.
Thomas et al., *Biochemistry,* 21(6):1162–9, 1982.
Tomicic et al., *Mutat. Res.,* 383(2):155–65, 1997.
Toorchen and Topel, *Carcinogenesis,* 4:1591, 1983.
Top et al., *J. Infect. Dis.,* 124:155–160, 1971.
Troelstra et al., *Genomics,* 12 (4):745–9, 1992.
Troelstra et al., *Cell,* 71(6):939–53, 1992.
Tur-Kaspa et al., *Mol. Cell Biol.,* 6:716–718, 1986.
U.S. Pat. No. 4,873,191
Varmus et al., *Cell,* 25:23 –36, 1981.
Vollberg, et al., *Carcinogenesis,* 8(11):1725–9, 1987.
Vollberg, et al., *Proc Nat'l. Acad. Sci USA,* 86(22):8693–7, 1989.
von Sonntag, et al., *Basic Life Sci,* 58:287–317; 1991.
Wagner and Hoppe, U.S. Pat. No. 4,873,191
Wagner et al., *Proc. Nat'l. Acad. Sci.,* 87(9):3410–3414, 1990.
Walker et al., *Proc. Nat'l Acad. Sci. USA,* 89:392–396 1992.
Wallace, *Envir. Mol. Mut.,* 12:431, 1988.
Wang et al., *Biochemical Pharmacology,* 51:1221, 1996.
Warner et al., *Proc. Nat'l. Acad. Sci. USA,* 77:4602–4606, 1980.
Washington et al., *Mut. Res.,* 207:165–169, 1988.
Weiss et al., *Intervirology,* 15(4):213–22, 1981.
Weng and Sirover, *Mutat. Res.,* 293(2):133–41, 1993.
Wigler et al., *Cell,* 11:223, 1977.
Wigler et al., *Proc. Nat'l Acad. Sci. USA,* 77:3567, 1980.
Williams et al., *J. Exp. Med.,* 166:210, 1987.
Williams et al., *Nature,* 310:476, 1984.
Willis and Lindahl, *Nature,* 325(6102):355–7, 1987.
Wilson et al., *J. Clin. Oncology,* 12:2301, 1995.
Wilson et al., *J. Biol. Chem.,* 269:25359–25364, 1994b.
Wilson et al., *Nucl. Acds. Res.,* 21:2516, 1993.
Wilson, *J. Biol. Chem.,* 269:25359–25364, 1994a.
Wist et al., 520(2):253–70,1978.
Wittwer and Krokan, *Biochim. Biophys. Acta,* 832(3): p308–18, 1985.
Wittwer et al., *Biochemistry,* 28(2):780–4, 1989.
Wong et al., *Gene,* 10:87–94,1980.
Woods et al., *Blood,* 87:4979, 1996.
Wu and Wu, *J. Biol. Chem.,* 262:4429–4432, 1987.
Wu and Wu, *Adv. Drug Delivery Rev.,* 12:159–167,1993.
Wu and Wu, *Biochemistry,* 27:887–892, 1988.
Xanthoudakis and Curran, *Adv. Exp. Med. Biol.,* 387:69–75, 1996.
Xanthoudakis and Curran, *EMBO J.,* 11(2):653–65, 1992.
Xanthoudakis et al., *EMBO J.,* 11(9):3323–35, 1992.
Xanthoudakis et al., *Proc. Nat'l. Acad. Sci. USA,* 91(1): 23–7, 1994
Xiao and Samson, *Proc Nat'l Acad Sci USA,* 90(6):2117–21, 1993
Yacoub et al., *EMBO J.,* 15(9):2306–12, 1996.
Yamamoto and Fujiwara, *Carcinogenesis,* 7(2):305–10, 1986.
Yang et al., *Proc. Natl. Acad. Sci USA,* 87:9568–9572, 1990.
Zaharko et al., *J. Phar. Exp. Therap.,* 189:585,1974.
Zanjani et al., *J. Clin. Invest.,* 93:1051, 1994.
Zelenin et al., *FEBS Lett.,* 280:94–96, 1991.

What is claimed is:

1. A fusion protein having DNA repair activity comprising a first DNA repair protein fused to a second DNA repair protein.

2. The fusion protein of claim 1, wherein the first repair protein is a direct reversal repair pathway enzyme and the second repair protein is a base excision repair enzyme.

3. The fusion protein of claim 2, wherein said second repair protein is from the base excision repair-A pathway.

4. The fusion protein of claim 2, wherein said second repair protein is from the base excision repair-B pathway.

5. The fusion protein of claim 3, wherein said second repair protein is selected from the group consisting of MPG, HAAG, APE, APN-1, β-polymerase, and DNA ligase.

6. The fusion protein of claim 4, wherein said second repair protein is selected from the group consisting of fpg, dS3, OGG1, EndoIII, Endo IV, exoIII, NTG-1, NTG-2, SCR-1, and SCR-2.

7. The fusion protein of claim 1, wherein said first repair protein is selected from the group consisting of hAPE, APN-1, NTG-1, NTG-2, SCR-1, SCR-2, exoIII, endoIV, endoIII, hMPG, fpg, dS3, β-polymerase, DNA ligase, HAAG, OGG1 and hMGMT and said second DNA repair protein is selected from the group consisting of hAPE, APN-1, NTG-1, NTG-2, SCR-1, SCR-2, exoIII, endoIV, endoIII, hMPG, fpg, dS3, β-polymerase, DNA ligase, HAAG, OGG1 and hMGMT, such that said first DNA repair protein is different from said second DNA repair protein.

8. The fusion protein of claim 3, further comprising a third DNA repair protein wherein said third DNA repair protein is a base excision repair protein.

9. The fusion protein of claim 2, wherein said first protein is hMGMT.

10. The fusion protein of claim 2, wherein said second protein comprises hAPE.

11. The fusion protein of claim 10, having a sequence of SEQ ID NO:2.

* * * * *